(12) United States Patent
Chen et al.

(10) Patent No.: US 9,873,697 B2
(45) Date of Patent: Jan. 23, 2018

(54) HISTONE DEMETHYLASE INHIBITORS

(71) Applicant: CELGENE QUANTICEL RESEARCH, INC., San Diego, CA (US)

(72) Inventors: Young K. Chen, San Marcos, CA (US); Michael Brennan Wallace, San Diego, CA (US)

(73) Assignee: Celgene Quantical Research, Inc., San Diego, CA (US)

( * ) Notice: Subject to any disclaimer, the term of this patent is extended or adjusted under 35 U.S.C. 154(b) by 0 days.

(21) Appl. No.: 15/652,174

(22) Filed: Jul. 17, 2017

(65) Prior Publication Data

US 2017/0313702 A1   Nov. 2, 2017

Related U.S. Application Data

(62) Division of application No. 14/774,329, filed as application No. PCT/US2014/023273 on Mar. 11, 2014, now Pat. No. 9,738,637.

(60) Provisional application No. 61/778,193, filed on Mar. 12, 2013.

(51) Int. Cl.
*C07D 471/04* (2006.01)

(52) U.S. Cl.
CPC .................. *C07D 471/04* (2013.01)

(58) Field of Classification Search
None
See application file for complete search history.

(56) References Cited

U.S. PATENT DOCUMENTS

| 6,232,320 | B1 | 5/2001 | Stewart et al. |
| 7,371,862 | B2 | 5/2008 | Vanotti et al. |
| 8,093,220 | B2 | 1/2012 | Atadja |
| 2007/0098816 | A1 | 5/2007 | Nakanishi et al. |
| 2014/0171432 | A1 | 6/2014 | Kanouni et al. |
| 2016/0108032 | A1 | 4/2016 | Chen et al. |

FOREIGN PATENT DOCUMENTS

| JP | 2012/107001 A | 6/2012 |
| WO | 2007/056281 A2 | 5/2007 |
| WO | 2008/135786 A1 | 11/2008 |
| WO | 2009/129335 A2 | 10/2009 |
| WO | 2013/028999 A1 | 2/2013 |
| WO | 2013/143597 A1 | 10/2013 |
| WO | 2014/164708 A1 | 10/2014 |

OTHER PUBLICATIONS

Berge et al., Pharmaceutical Salts. Journal of Pharmaceutical Sciences 66(1):1-19 (Jan. 1977).
Bundgard et al., Design of Prodrugs, pp. 709, 21-24 (1985).
Cheung et al., Efficient and regioselective synthesis of 2-alkyl-2H-indazoles, J. Org. Chem. 68(1):4093-4095 (May 2003).
Extended European Search Report dated, Jul. 25, 2016, issued in related European Patent Application No. 14778281.7, filed Mar. 11, 2014.
Higuchi et al., Pro-drugs as Novel Delivery Systems. A.C.S. Symposium Series, vol. 14 (1975).
International Preliminary Report on Patentability dated, Sep. 24, 2015, in International Patent Application No. PCT/US2014/23273, filed Mar. 11, 2014.
International Search Report and Written Opinion dated, Jun. 18, 2014, in International Patent Application No. PCT/US2015/049926, filed Mar. 11, 2014.
International Search Report and Written Opinion dated, Dec. 4, 2015, in International Patent Application No. PCT/US2015/049926, filed Sep. 14, 2015.
Lachner et al., "An epigenetic road map for histone lysine methylation," Journal of Cell Science 116:2117-2123 (Jun. 1, 2003).
Lin et al., "Loss of the retinoblastoma binding protein 2 (RBP2) histone demethylase suppresses tumorigenesis in mice lacking RB1 or Men1." PNAS 108(33):13379-13386 (2011).
Margueron et al., "The key to development: interpreting the histone code?" Current Opinion in Genetics & Development 15:163-176 (2005).
McLaughlin et al., Efficient Access to Azaindoles and Indoles. Org. Lett. 8(15):3307-3310 (2006).
Nazare et al., A Flexible, Palladium-Catalyzed Indole and Azaindole Synthesis by Direct Annulation of Chloroanilinles and Chloroaminopyridines with Ketones. Agnew. Chem. Int. Ed. 43(34):4526-4528 (2004).
Sonogashira et al., A convenient synthesis of acetylenes: catalytic substitutions of acetylenic hydrogen with bromoalkenes, iodoarenes and bromopyridines. Tetrahedron Lett. 16(50):4467-4470 (1975).
Stahl et al., Handbook of Pharmaceutical Salts. Verlag Helvetica Chimica Acta, Zurich (2002).

*Primary Examiner* — Heidi Reese
(74) *Attorney, Agent, or Firm* — Wiley Rein LLP

(57) ABSTRACT

The present invention relates generally to compositions and methods for treating cancer and neoplastic disease. Provided herein are substituted pyrrolopyridine derivative compounds and pharmaceutical compositions comprising said compounds. The subject compounds and compositions are useful for inhibition of histone demethylase. Furthermore, the subject compounds and compositions are useful for the treatment of cancer, such as prostate cancer, breast cancer, bladder cancer, lung cancer and/or melanoma and the like.

20 Claims, No Drawings

HISTONE DEMETHYLASE INHIBITORS

RELATED APPLICATIONS

This application is a Division of U.S. patent application Ser. No. 14/774,329, filed Jun. 18, 2015, which is a National Stage Application of PCT/US2014/23273, filed Mar. 11, 2014, which claims the priority benefit of U.S. Provisional Application 61/778,193, filed Mar. 12, 2013, the contents of which are hereby incorporated by reference in their entireties.

BACKGROUND

A need exists in the art for an effective treatment of cancer and neoplastic disease.

BRIEF SUMMARY OF THE INVENTION

Provided herein are substituted pyrrolopyridine derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like. The substituted pyrrolopyridine derivative compounds described herein are based upon a disubstituted pyrrolo[3,2-b]pyridine ring system bearing at the 7-position a carboxylic acid or bioisostere thereof, and a second substituent at the 2-position. The 2-position substituent, in various embodiments, is selected from a wide variety of groups, such as, but not limited to, alkyl, aryl, carbocyclyl, and the like.

One embodiment provides a compound having the structure of Formula (I),

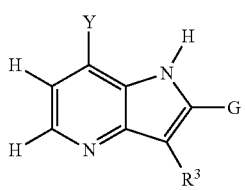

Formula (I)

or a pharmaceutically acceptable salt thereof, wherein,

Y is —$CO_2R^1$, —C(O)N(H)CN, —C(O)N(H)OH, or tetrazolyl, wherein $R^1$ is hydrogen or alkyl;

G is X—$R^2$ or $X^1$-alkyl, wherein

X is a bond, alkylene, alkylene-O—, —C(O)—, —C(O)—NH—, —NH—, —NH—C(O)—, —O—, —S—, or —$SO_2$—;

$R^2$ is selected from carbocyclyl, heterocyclyl, aryl, or heteroaryl;

$X^1$ is a bond, —C(O)—, —C(O)—NH—, —NH—, —NH—C(O), —O—, —S—, or —$SO_2$—; and $R^3$ is hydrogen, halogen, or alkyl.

Another embodiment provides the compound of Formula (I) represented by the structure of Formula (II),

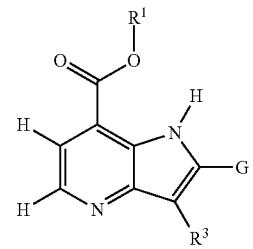

Formula (II)

or a pharmaceutically acceptable salt thereof, wherein, $R^1$ is hydrogen or alkyl;

G is X—$R^2$ or $X^1$-alkyl, wherein

X is a bond, alkylene, alkylene-O—, —C(O)—, —C(O)—NH—, —NH—, —NH—C(O)—, —O—, —S—, or —$SO_2$—;

$R^2$ is selected from carbocyclyl, heterocyclyl, aryl, or heteroaryl;

$X^1$ is a bond, —C(O)—, —C(O)—NH—, —NH—, —NH—C(O)—, —O—, —S—, or —$SO_2$—; and $R^3$ is hydrogen, halogen or alkyl.

One embodiment provides a pharmaceutical composition comprising a pharmaceutically acceptable carrier and a compound of Formula (I) or a pharmaceutically acceptable salt thereof.

One embodiment provides a method for treating cancer in subject comprising administering a composition comprising a compound of Formula (I) or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $-R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $-R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula $-O-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclo-octenyl. Polycyclic carbocyclyl radicals include, for example, adamantyl, norbornyl (i.e., bicyclo-[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $-R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula $-O-R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^bOC(O)R^a$, —$R^bOC(O)OR^a$, —$R^bOC(O)N(R^a)_2$, —$R^bN(R^a)_2$, —$R^bC(O)R^a$, —$R^bC(O)OR^a$, —$R^bC(O)N(R^a)_2$, —$R^bOR^cC(O)N(R^a)_2$, —$R^bN(R^a)C(O)OR^a$, —$R^bN(R^a)C(O)R^a$, —$R^bN(R^a)S(O)_tR^a$ (where t is 1 or 2), —$R^bS(O)_tOR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexa-hydrocycloocta[d]pyrimidinyl, 5,6,7,8,9,10-hexahydrocycloocta[d]pyridazinyl, 5,6,7,8,9,10-hexa-hydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydro-quinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, pheno-thiazinyl, phenoxazinyl, phthalazinyl, pteridinyl, purinyl, pyrrolyl, pyrazolyl, pyrazolo[3,4-d]-pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetra-hydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]-pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^bOC(O)R^a$, —$R^bOC(O)OR^a$, —$R^bOC(O)N(R^a)_2$, —$R^bN(R^a)_2$, —$R^bC(O)R^a$, —$R^bC(O)OR^a$, —$R^bC(O)N(R^a)_2$, —$R^bOR^cC(O)N(R^a)_2$, —$R^bN(R^a)C(O)OR^a$, —$R^bN(R^a)C(O)R^a$, —$R^bN(R^a)S(O)_tR^a$ (where t is 1 or 2), —$R^bS(O)_tOR^a$ (where t is 1 or 2), —$R^bS(O)_tOR^a$ (where t is 1 or 2) and —$R^bS(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

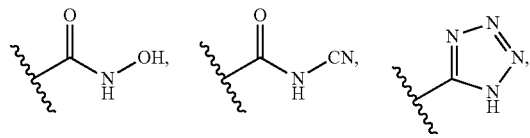

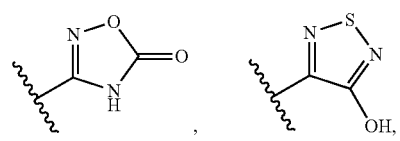

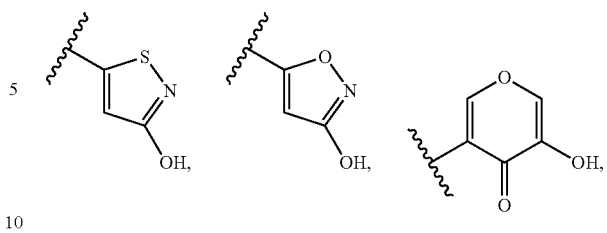

and the like.

The compounds disclosed herein may contain one or more asymmetric centers and may thus give rise to enantiomers, diastereomers, and other stereoisomeric forms that may be defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

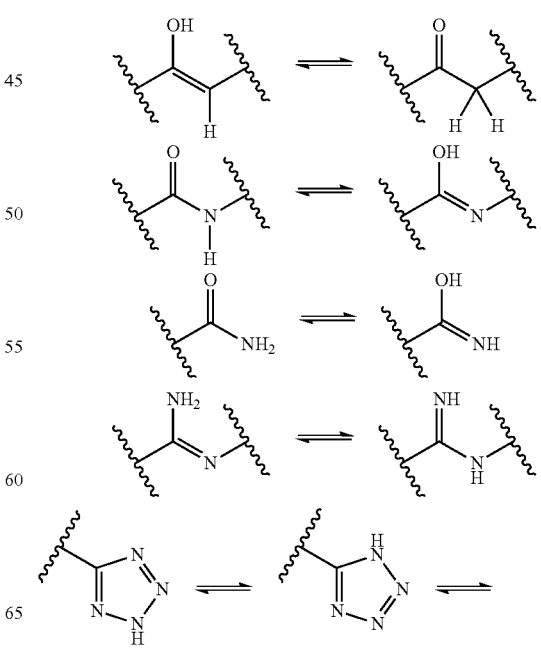

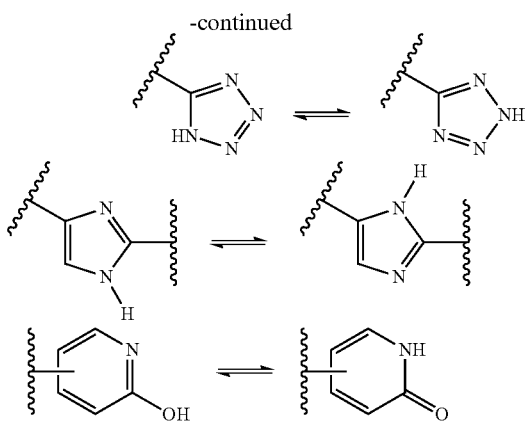

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted pyrrolopyridine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitro-benzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds, and the like.

Substituted Pyrrolopyridine Derivative Compounds

Substituted pyrrolopyridine derivative compounds are described herein that inhibit a histone demethylase enzyme. These compounds, and compositions comprising these compounds, are useful for the treatment of cancer and neoplastic disease. The compounds described herein may, therefore, be useful for treating prostate cancer, breast cancer, bladder cancer, lung cancer and/or melanoma and the like.

One embodiment provides a compound having the structure of Formula (I),

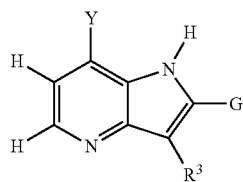

Formula (I)

or a pharmaceutically acceptable salt thereof, wherein,

Y is —CO$_2$R$^1$, —C(O)N(H)CN, —C(O)N(H)OH or tetrazolyl;

R$^1$ is hydrogen or alkyl;

G is X—R$^2$ or X$^1$-alkyl, wherein

X is a bond, alkylene, alkylene-O—, —C(O)—, —C(O)—NH—, —NH—, —NH—C(O)—, —O—, —S—, or —SO$_2$—;

R$^2$ is selected from carbocyclyl, heterocyclyl, aryl, or heteroaryl;

X$^1$ is a bond, —C(O)—, —C(O)—NH—, —NH—, —NH—C(O)—, —O—, —S—, or —SO$_2$—; and

R$^3$ is hydrogen, halogen or alkyl.

Another embodiment provides the compound having the structure of Formula (I), wherein Y is —CO$_2$R$^1$ and R$^1$ is hydrogen. Another embodiment provides the compound having the structure of Formula (I), wherein Y is —CO$_2$R$^1$ and R$^1$ is alkyl. Another embodiment provides the compound having the structure of Formula (I), wherein Y is —C(O)N(H)CN. Another embodiment provides the compound having the structure of Formula (I), wherein Y is —C(O)N(H)OH. Another embodiment provides the compound having the structure of Formula (I), wherein Y is tetrazolyl.

Another embodiment provides the compound having the structure of Formula (I), wherein R$^3$ is hydrogen.

Another embodiment provides the compound having the structure of Formula (I), wherein G is X—R$^2$. Another embodiment provides the compound having the structure of Formula (I), wherein X is a bond and R$^2$ is aryl. Another embodiment provides the compound having the structure of Formula (I), wherein X is alkylene and R$^2$ is aryl. Another embodiment provides the compound having the structure of Formula (I), wherein alkylene is substituted with —OH, alkoxy, alkylamino, or dialkylamino. Another embodiment provides the compound having the structure of Formula (I), wherein X is a C$_1$-C$_3$ alkylene and R$^2$ is aryl. Another embodiment provides the compound having the structure of Formula (I), wherein X is a bond and R$^2$ is carbocyclyl. Another embodiment provides the compound having the structure of Formula (I), wherein R$^2$ is C$_3$-C$_7$ carbocyclyl. Another embodiment provides the compound having the structure of Formula (I), wherein the carbocyclyl is a 1-hydroxy carbocyclyl. Another embodiment provides the compound having the structure of Formula (I), wherein X is a bond and R$^2$ is heteroaryl. Another embodiment provides the compound having the structure of Formula (I), wherein X is a bond and R$^2$ is heterocyclyl. Another embodiment provides the compound having the structure of Formula (I), wherein X is alkylene and R$^2$ is carbocyclyl. Another embodiment provides the compound having the structure of Formula (I), wherein alkylene is substituted with —OH, alkoxy, alkylamino, or dialkylamino. Another embodiment provides the compound having the structure of Formula (I), wherein R$^2$ is C$_3$-C$_7$ carbocyclyl. Another embodiment provides the compound having the structure of Formula (I), wherein X is C$_1$-C$_3$ alkylene and R$^2$ is carbocyclyl. Another embodiment provides the compound having the structure of Formula (I), wherein R$^2$ is C$_3$-C$_7$ carbocyclyl. Another embodiment provides the compound having the structure of Formula (I), wherein X is alkylene and R$^2$ is heteroaryl. Another embodiment provides the compound having the structure of Formula (I), wherein alkylene is substituted with —OH, alkoxy, alkylamino, or dialkylamino. Another embodiment provides the compound having the structure of Formula (I), wherein X is C$_1$-C$_3$ alkylene and R$^2$ is heteroaryl. Another embodiment provides the compound having the structure of Formula (I), wherein X is alkylene and R$^2$ is heterocyclyl. Another embodiment provides the compound having the structure of Formula (I), wherein alkylene is substituted with —OH, alkoxy, alkylamino, or dialkylamino. Another embodiment provides the compound having the structure of Formula (I), wherein X is C$_1$-C$_3$ alkylene and R$^2$ is heterocyclyl. Another embodiment provides the compound having the structure of Formula (I), wherein X is —C(O)— and R$^2$ is aryl. Another embodiment provides the compound having the structure of Formula (I), wherein X is —C(O)— and R$^2$ is heteroaryl. Another embodiment provides the compound having the structure of Formula (I), wherein X is —C(O)— and R$^2$ is carbocyclyl. Another embodiment provides the compound having the structure of Formula (I), wherein R$^2$ is C$_3$-C$_7$ carbocyclyl. Another embodiment provides the compound having the structure of Formula (I), wherein X is —C(O)— and R$^2$ is heterocyclyl. Another embodiment provides the compound having the structure of Formula (I), wherein X is —C(O)—NH— and R$^2$ is aryl. Another embodiment provides the compound having the structure of Formula (I), wherein X is —C(O)—NH— and R$^2$ is heteroaryl. Another embodiment provides the compound having the structure of Formula (I), wherein X is —C(O)—NH— and R$^2$ is carbocyclyl. Another embodiment provides the compound having the structure of Formula (I), wherein R$^2$ is C$_3$-C$_7$ carbocyclyl. Another embodiment provides the compound having the structure of Formula (I), wherein X is —C(O)—NH— and R$^2$ is heterocyclyl. Another embodiment provides the compound having the structure of Formula (I), wherein X is —NH— and R$^2$ is aryl. Another embodiment provides the compound having the structure of Formula (I), wherein X is —NH— and R$^2$ is heteroaryl. Another embodiment provides the compound having the structure of Formula (I), wherein X is —NH— and R$^2$ is carbocyclyl. Another embodiment provides the compound having the structure of Formula (I), wherein R$^2$ is C$_3$-C$_7$ carbocyclyl. Another embodiment provides the compound having the structure of Formula (I), wherein X is —NH— and R² is heterocyclyl. Another embodiment provides the compound having the structure of Formula (I), wherein X is —NH—C(O)— and R² is aryl. Another embodiment provides the compound having the structure of Formula (I), wherein X is —NH—C(O)— and R² is heteroaryl. Another embodiment provides the compound having the structure of Formula (I), wherein X is —NH—C(O)— and R² is carbocyclyl. Another embodiment provides the compound having the structure of Formula (I), wherein R² is $C_3$-$C_7$ carbocyclyl. Another embodiment provides the compound having the structure of Formula (I), wherein X is —NH—C(O)— and R² is heterocyclyl. Another embodiment provides the compound having the structure of Formula (I), wherein X is —O— and R² is aryl. Another embodiment provides the compound having the structure of Formula (I), wherein X is —O— and R² is heteroaryl. Another embodiment provides the compound having the structure of Formula (I), wherein X is —O— and R² is carbocyclyl. Another embodiment provides the compound having the structure of Formula (I), wherein R² is $C_3$-$C_7$ carbocyclyl. Another embodiment provides the compound having the structure of Formula (I), wherein X is —O— and R² is heterocyclyl. Another embodiment provides the compound having the structure of Formula (I), wherein X is —S— and R² is aryl. Another embodiment provides the compound having the structure of Formula (I), wherein X is —S— and R² is heteroaryl. Another embodiment provides the compound having the structure of Formula (I), wherein X is —S— and R² is carbocyclyl. Another embodiment provides the compound having the structure of Formula (I), wherein R² is $C_3$-$C_7$ carbocyclyl. Another embodiment provides the compound having the structure of Formula (I), wherein X is —S— and R² is heterocyclyl. Another embodiment provides the compound having the structure of Formula (I), wherein X is —$SO_2$— and R² is aryl. Another embodiment provides the compound having the structure of Formula (I), wherein X is —$SO_2$— and R² is heteroaryl. Another embodiment provides the compound having the structure of Formula (I), wherein X is —$SO_2$— and R² is carbocyclyl. Another embodiment provides the compound having the structure of Formula (I), wherein R² is $C_3$-$C_7$ carbocyclyl. Another embodiment provides the compound having the structure of Formula (I), wherein X is —$SO_2$— and R² is heterocyclyl.

Another embodiment provides the compound having the structure of Formula (I), wherein G is $X^1$-alkyl. Another embodiment provides the compound having the structure of Formula (I), wherein $X^1$ is a bond. Another embodiment provides the compound having the structure of Formula (I), wherein the alkyl is a $C_1$-$C_4$ alkyl. Another embodiment provides the compound having the structure of Formula (I), wherein the alkyl is a 1-hydroxyalkyl. Another embodiment provides the compound having the structure of Formula (I), wherein the alkyl is a $C_2$-$C_4$ 1-hydroxyalkyl. Another embodiment provides the compound having the structure of Formula (I), wherein $X^1$ is —C(O)—. Another embodiment provides the compound having the structure of Formula (I), wherein the alkyl is a $C_1$-$C_4$ alkyl. Another embodiment provides the compound having the structure of Formula (I), wherein $X^1$ is —C(O)—NH—. Another embodiment provides the compound having the structure of Formula (I), wherein the alkyl is a $C_1$-$C_4$ alkyl. Another embodiment provides the compound having the structure of Formula (I), wherein $X^1$ is —NH—. Another embodiment provides the compound having the structure of Formula (I), wherein the alkyl is a $C_1$-$C_4$ alkyl. Another embodiment provides the compound having the structure of Formula (I), wherein $X^1$ is —NH—C(O)—. Another embodiment provides the compound having the structure of Formula (I), wherein the alkyl is a $C_1$-$C_4$ alkyl. Another embodiment provides the compound having the structure of Formula (I), wherein $X^1$ is —O—. Another embodiment provides the compound having the structure of Formula (I), wherein the alkyl is a $C_1$-$C_4$ alkyl. Another embodiment provides the compound having the structure of Formula (I), wherein $X^1$ is —S—. Another embodiment provides the compound having the structure of Formula (I), wherein the alkyl is a $C_1$-$C_4$ alkyl. Another embodiment provides the compound having the structure of Formula (I), wherein $X^1$ is —$SO_2$—. Another embodiment provides the compound having the structure of Formula (I), wherein the alkyl is a $C_1$-$C_4$ alkyl. Another embodiment provides the compound having the structure of Formula (I), wherein X is alkylene-O—. Another embodiment provides the compound having the structure of Formula (I), wherein X is alkylene-O—, and R² is aryl. Another embodiment provides the compound having the structure of Formula (I), wherein X is alkylene-O—, and R² is heteroaryl. Another embodiment provides the compound having the structure of Formula (I), wherein X is alkylene-O—, and R² is carbocyclyl. Another embodiment provides the compound having the structure of Formula (I), wherein R² is $C_3$-$C_7$ carbocyclyl. Another embodiment provides the compound having the structure of Formula (I), wherein X is alkylene-O—, and R² is heterocyclyl. Another embodiment provides the compound having the structure of Formula (I), wherein the alkylene is a $C_1$-$C_3$ alkylene.

Another embodiment provides the compound of Formula (I) represented by the structure of Formula (II),

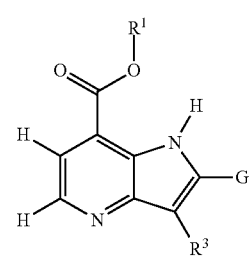

Formula (II)

or a pharmaceutically acceptable salt thereof, wherein
R¹ is hydrogen or alkyl;
G is X—R² or $X^1$-alkyl, wherein
X is a bond, alkylene, alkylene-O—, —C(O)—, —C(O)—NH—, —NH—, —NH—C(O)—, —O—, —S—, or —$SO_2$—;
R² is selected from carbocyclyl, heterocyclyl, aryl, or heteroaryl;
$X^1$ is a bond, —C(O)—, —C(O)—NH—, —NH—, —NH—C(O)—, —O—, —S—, or —$SO_2$—; and
R³ is hydrogen, halogen or alkyl.

Another embodiment provides the compound having the structure of Formula (II), wherein R¹ is hydrogen. Another embodiment provides the compound having the structure of Formula (II), wherein R¹ is alkyl. Another embodiment provides the compound having the structure of Formula (II), wherein G is X—R². Another embodiment provides the compound having the structure of Formula (II), wherein X is a bond and R² is aryl. Another embodiment provides the compound having the structure of Formula (II), wherein X is alkylene and R² is aryl. Another embodiment provides the compound having the structure of Formula (II), wherein alkylene is substituted with —OH, alkoxy, alkylamino, or dialkylamino. Another embodiment provides the compound having the structure of Formula (II), wherein X is a $C_1$-$C_3$ alkylene and $R^2$ is aryl. Another embodiment provides the compound having the structure of Formula (II), wherein X is a bond and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein the carbocyclyl is a 1-hydroxy carbocyclyl. Another embodiment provides the compound having the structure of Formula (II), wherein X is a bond and $R^2$ is heteroaryl. Another embodiment provides the compound having the structure of Formula (II), wherein X is a bond and $R^2$ is heterocyclyl. Another embodiment provides the compound having the structure of Formula (II), wherein X is alkylene and $R^2$ is carbocyclyl. Another embodiment provides the compound having the structure of Formula (II), wherein alkylene is substituted with —OH, alkoxy, alkylamino, or dialkylamino. Another embodiment provides the compound having the structure of Formula (II), wherein $R^2$ is $C_3$-$C_7$ carbocyclyl. Another embodiment provides the compound having the structure of Formula (II), wherein X is $C_1$-$C_3$ alkylene and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is alkylene and $R^2$ is heteroaryl. Another embodiment provides the compound having the structure of Formula (II), wherein alkylene is substituted with —OH, alkoxy, alkylamino, or dialkylamino. Another embodiment provides the compound having the structure of Formula (II), wherein X is $C_1$-$C_3$ alkylene and $R^2$ is heteroaryl. Another embodiment provides the compound having the structure of Formula (II), wherein X is alkylene and $R^2$ is heterocyclyl. Another embodiment provides the compound having the structure of Formula (II), wherein alkylene is substituted with —OH, alkoxy, alkylamino, or dialkylamino. Another embodiment provides the compound having the structure of Formula (II), wherein X is $C_1$-$C_3$ alkylene and $R^2$ is heterocyclyl. Another embodiment provides the compound having the structure of Formula (II), wherein X is —C(O)— and $R^2$ is aryl. Another embodiment provides the compound having the structure of Formula (II), wherein X is —C(O)— and $R^2$ is heteroaryl. Another embodiment provides the compound having the structure of Formula (II), wherein X is —C(O)— and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is —C(O)— and $R^2$ is heterocyclyl. Another embodiment provides the compound having the structure of Formula (II), wherein X is —C(O)—NH— and $R^2$ is aryl. Another embodiment provides the compound having the structure of Formula (II), wherein X is —C(O)—NH— and $R^2$ is heteroaryl. Another embodiment provides the compound having the structure of Formula (II), wherein X is —C(O)—NH— and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is —C(O)—NH— and $R^2$ is heterocyclyl. Another embodiment provides the compound having the structure of Formula (II), wherein X is —NH— and $R^2$ is aryl. Another embodiment provides the compound having the structure of Formula (II), wherein X is —NH— and $R^2$ is heteroaryl. Another embodiment provides the compound having the structure of Formula (II), wherein X is —NH— and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is —NH— and $R^2$ is heterocyclyl. Another embodiment provides the compound having the structure of Formula (II), wherein X is —NH—C(O)— and $R^2$ is aryl. Another embodiment provides the compound having the structure of Formula (II), wherein X is —NH—C(O)— and $R^2$ is heteroaryl. Another embodiment provides the compound having the structure of Formula (II), wherein X is —NH—C(O)— and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is —NH—C(O)— and $R^2$ is heterocyclyl. Another embodiment provides the compound having the structure of Formula (II), wherein X is —O— and $R^2$ is aryl. Another embodiment provides the compound having the structure of Formula (II), wherein X is —O— and $R^2$ is heteroaryl. Another embodiment provides the compound having the structure of Formula (II), wherein X is —O— and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is —O— and $R^2$ is heterocyclyl. Another embodiment provides the compound having the structure of Formula (II), wherein X is —S— and $R^2$ is aryl. Another embodiment provides the compound having the structure of Formula (II), wherein X is —S— and $R^2$ is heteroaryl. Another embodiment provides the compound having the structure of Formula (II), wherein X is —S— and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is —S— and $R^2$ is heterocyclyl. Another embodiment provides the compound having the structure of Formula (II), wherein X is —$SO_2$— and $R^2$ is aryl. Another embodiment provides the compound having the structure of Formula (II), wherein X is —$SO_2$— and $R^2$ is heteroaryl. Another embodiment provides the compound having the structure of Formula (II), wherein X is —$SO_2$— and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is —$SO_2$— and $R^2$ is heterocyclyl.

Another embodiment provides the compound having the structure of Formula (II), wherein G is $X^1$-alkyl. Another embodiment provides the compound having the structure of Formula (II), wherein $X^1$ is a bond. Another embodiment provides the compound having the structure of Formula (II), wherein the alkyl is a $C_1$-$C_4$ alkyl. Another embodiment provides the compound having the structure of Formula (II), wherein the alkyl is a 1-hydroxyalkyl. Another embodiment provides the compound having the structure of Formula (II), wherein the alkyl is a $C_2$-$C_4$ 1-hydroxyalkyl. Another embodiment provides the compound having the structure of Formula (II), wherein $X^1$ is —C(O)—. Another embodiment provides the compound having the structure of Formula (II), wherein the alkyl is a $C_1$-$C_4$ alkyl. Another embodiment provides the compound having the structure of Formula (II), wherein $X^1$ is —C(O)—NH—. Another embodiment provides the compound having the structure of Formula (II), wherein the alkyl is a $C_1$-$C_4$ alkyl. Another embodiment provides the compound having the structure of Formula (II), wherein $X^1$ is —NH—. Another embodiment provides the compound having the structure of Formula (II), wherein the alkyl is a $C_1$-$C_4$ alkyl. Another embodiment provides the compound having the structure of Formula (II), wherein $X^1$ is —NH—C(O)—. Another embodiment provides the compound having the structure of Formula (II), wherein the alkyl is a $C_1$-$C_4$ alkyl. Another embodiment provides the compound having the structure of Formula (II), wherein $X^1$ is —O—. Another embodiment provides the compound having the structure of Formula (II), wherein the alkyl is a $C_1$-$C_4$ alkyl. Another embodiment provides the compound having the structure of Formula (II), wherein $X^1$ is —S—. Another embodiment provides the compound having the structure of Formula (II), wherein the alkyl is a C1-C4 alkyl. Another embodiment provides the compound having the structure of Formula (II), wherein $X^1$ is —SO$_2$—. Another embodiment provides the compound having the structure of Formula (II), wherein the alkyl is a $C_1$-$C_4$ alkyl. Another embodiment provides the compound having the structure of Formula (II), wherein X is alkylene-O—. Another embodiment provides the compound having the structure of Formula (II), wherein X is alkylene-O—, and $R^2$ is aryl. Another embodiment provides the compound having the structure of Formula (II), wherein X is alkylene-O—, and $R^2$ is heteroaryl. Another embodiment provides the compound having the structure of Formula (II), wherein X is alkylene-O—, and $R^2$ is carbocyclyl. Another embodiment provides the compound having the structure of Formula (II), wherein $R^2$ is $C_3$-$C_7$ carbocyclyl. Another embodiment provides the compound having the structure of Formula (II), wherein X is alkylene-O—, and $R^2$ is heterocyclyl. Another embodiment provides the compound having the structure of Formula (II), wherein the alkylene is a $C_1$-$C_3$ alkylene.

One embodiment provides a compound having the structure of Formula (Ia),

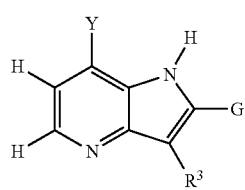

Formula (Ia)

or a pharmaceutically acceptable salt thereof, wherein,
Y is —CO$_2$R$^1$, —C(O)NH—(C$_1$-C$_3$)alkyl, —C(O)N(H)CN, —C(O)N(H)OH or tetrazolyl;
$R^1$ is hydrogen, alkyl, heterocyclylalkyl, or carbocyclylalkyl;
G is X—R$^2$ or X$^1$-alkyl, wherein
 X is a bond, alkylene, alkylene-O—, —C(O)—, —C(O)—NH—, —NH—, —NH—C(O)—, —O—, —S—, or —SO$_2$—;
$R^2$ is selected from carbocyclyl, heterocyclyl, aryl, or heteroaryl;
$X^1$ is a bond, —C(O)—, —C(O)—NH—, —NH—, —NH—C(O)—, —O—, —S—, or —SO$_2$—; and
$R^3$ is hydrogen, halogen or alkyl.

Another embodiment provides the compound having the structure of Formula (Ia), wherein Y is —CO$_2$R$^1$ and R$^1$ is hydrogen. Another embodiment provides the compound having the structure of Formula (Ia), wherein Y is —CO$_2$R$^1$ and R$^1$ is alkyl. Another embodiment provides the compound having the structure of Formula (Ia), wherein Y is —CO$_2$R$^1$ and R$^1$ is heterocyclylalkyl. Another embodiment provides the compound having the structure of Formula (Ia), wherein Y is —CO$_2$R$^1$ and R$^1$ is carbocyclylalkyl. Another embodiment provides the compound having the structure of Formula (Ia), wherein Y is —C(O)NH—(C$_1$-C$_3$)alkyl. Another embodiment provides the compound having the structure of Formula (Ia), wherein Y is —C(O)N(H)CN. Another embodiment provides the compound having the structure of Formula (Ia), wherein Y is —C(O)N(H)OH. Another embodiment provides the compound having the structure of Formula (Ia), wherein Y is tetrazolyl.

Another embodiment provides the compound having the structure of Formula (Ia), wherein $R^3$ is hydrogen.

Another embodiment provides the compound having the structure of Formula (Ia), wherein G is X—R$^2$. Another embodiment provides the compound having the structure of Formula (Ia), wherein X is a bond and $R^2$ is aryl. Another embodiment provides the compound having the structure of Formula (Ia), wherein X is alkylene and $R^2$ is aryl. Another embodiment provides the compound having the structure of Formula (Ia), wherein alkylene is substituted with —OH, alkoxy, alkylamino, or dialkylamino. Another embodiment provides the compound having the structure of Formula (Ia), wherein X is a $C_1$-$C_3$ alkylene and $R^2$ is aryl. Another embodiment provides the compound having the structure of Formula (Ia), wherein X is a bond and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein the carbocyclyl is a 1-hydroxy carbocyclyl. Another embodiment provides the compound having the structure of Formula (Ia), wherein X is a bond and $R^2$ is heteroaryl. Another embodiment provides the compound having the structure of Formula (Ia), wherein X is a bond and $R^2$ is heterocyclyl. Another embodiment provides the compound having the structure of Formula (Ia), wherein X is alkylene and $R^2$ is carbocyclyl. Another embodiment provides the compound having the structure of Formula (Ia), wherein alkylene is substituted with —OH, alkoxy, alkylamino, or dialkylamino. Another embodiment provides the compound having the structure of Formula (Ia), wherein $R^2$ is $C_3$-$C_7$ carbocyclyl. Another embodiment provides the compound having the structure of Formula (Ia), wherein X is $C_1$-$C_3$ alkylene and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is alkylene and $R^2$ is heteroaryl. Another embodiment provides the compound having the structure of Formula (Ia), wherein alkylene is substituted with —OH, alkoxy, alkylamino, or dialkylamino. Another embodiment provides the compound having the structure of Formula (Ia), wherein X is $C_1$-$C_3$ alkylene and $R^2$ is heteroaryl. Another embodiment provides the compound having the structure of Formula (Ia), wherein X is alkylene and $R^2$ is heterocyclyl. Another embodiment provides the compound having the structure of Formula (Ia), wherein alkylene is substituted with —OH, alkoxy, alkylamino, or dialkylamino. Another embodiment provides the compound having the structure of Formula (Ia), wherein X is C1-C3 alkylene and $R^2$ is heterocyclyl. Another embodiment provides the compound having the structure of Formula (Ia), wherein X is —C(O)— and $R^2$ is aryl. Another embodiment provides the compound having the structure of Formula (Ia), wherein X is —C(O)— and $R^2$ is heteroaryl. Another embodiment provides the compound having the structure of Formula (Ia), wherein X is —C(O)— and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is —C(O)— and $R^2$ is heterocyclyl. Another embodiment provides the compound having the structure of Formula (Ia), wherein X is —C(O)—NH— and $R^2$ is aryl. Another embodiment provides the compound having the structure of Formula (Ia), wherein X is —C(O)—NH— and $R^2$ is heteroaryl. Another embodiment provides the compound having the structure of Formula (Ia), wherein X is —C(O)—NH— and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is —C(O)—NH— and $R^2$ is heterocyclyl. Another embodiment provides the compound having the structure of Formula (Ia), wherein X is —NH— and $R^2$ is aryl. Another embodiment provides the compound having the structure of Formula (Ia), wherein X is —NH— and $R^2$ is heteroaryl. Another embodiment provides the compound having the structure of Formula (Ia), wherein X is —NH— and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is —NH— and $R^2$ is heterocyclyl. Another embodiment provides the compound having the structure of Formula (Ia), wherein X is —NH—C(O)— and $R^2$ is aryl. Another embodiment provides the compound having the structure of Formula (Ia), wherein X is —NH—C(O)— and $R^2$ is heteroaryl. Another embodiment provides the compound having the structure of Formula (Ia), wherein X is —NH—C(O)— and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is —NH—C(O)— and $R^2$ is heterocyclyl. Another embodiment provides the compound having the structure of Formula (Ia), wherein X is —O— and $R^2$ is aryl. Another embodiment provides the compound having the structure of Formula (Ia), wherein X is —O— and $R^2$ is heteroaryl. Another embodiment provides the compound having the structure of Formula (Ia), wherein X is —O— and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is —O— and $R^2$ is heterocyclyl. Another embodiment provides the compound having the structure of Formula (Ia), wherein X is —S— and $R^2$ is aryl. Another embodiment provides the compound having the structure of Formula (Ia), wherein X is —S— and $R^2$ is heteroaryl. Another embodiment provides the compound having the structure of Formula (Ia), wherein X is —S— and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is —S— and $R^2$ is heterocyclyl. Another embodiment provides the compound having the structure of Formula (Ia), wherein X is —SO$_2$— and $R^2$ is aryl. Another embodiment provides the compound having the structure of Formula (Ia), wherein X is —SO$_2$— and $R^2$ is heteroaryl. Another embodiment provides the compound having the structure of Formula (Ia), wherein X is —SO$_2$— and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is —SO$_2$— and $R^2$ is heterocyclyl.

Another embodiment provides the compound having the structure of Formula (Ia), wherein G is $X^1$-alkyl. Another embodiment provides the compound having the structure of Formula (Ia), wherein $X^1$ is a bond. Another embodiment provides the compound having the structure of Formula (Ia), wherein the alkyl is a $C_1$-$C_4$ alkyl. Another embodiment provides the compound having the structure of Formula (Ia), wherein the alkyl is a 1-hydroxyalkyl. Another embodiment provides the compound having the structure of Formula (Ia), wherein the alkyl is a $C_2$-$C_4$ 1-hydroxyalkyl. Another embodiment provides the compound having the structure of Formula (Ia), wherein $X^1$ is —C(O)—. Another embodiment provides the compound having the structure of Formula (Ia), wherein the alkyl is a $C_1$-$C_4$ alkyl. Another embodiment provides the compound having the structure of Formula (Ia), wherein $X^1$ is —C(O)—NH—. Another embodiment provides the compound having the structure of Formula (Ia), wherein the alkyl is a $C_1$-$C_4$ alkyl. Another embodiment provides the compound having the structure of Formula (Ia), wherein $X^1$ is —NH—. Another embodiment provides the compound having the structure of Formula (Ia), wherein the alkyl is a $C_1$-$C_4$ alkyl. Another embodiment provides the compound having the structure of Formula (Ia), wherein $X^1$ is —NH—C(O)—. Another embodiment provides the compound having the structure of Formula (Ia), wherein the alkyl is a $C_1$-$C_4$ alkyl. Another embodiment provides the compound having the structure of Formula (Ia), wherein $X^1$ is —O—. Another embodiment provides the compound having the structure of Formula (Ia), wherein the alkyl is a $C_1$-$C_4$ alkyl. Another embodiment provides the compound having the structure of Formula (Ia), wherein $X^1$ is —S—. Another embodiment provides the compound having the structure of Formula (Ia), wherein the alkyl is a $C_1$-$C_4$ alkyl. Another embodiment provides the compound having the structure of Formula (Ia), wherein $X^1$ is —SO$_2$—. Another embodiment provides the compound having the structure of Formula (Ia), wherein the alkyl is a $C_1$-$C_4$ alkyl. Another embodiment provides the compound having the structure of Formula (Ia), wherein X is alkylene-O—. Another embodiment provides the compound having the structure of Formula (Ia), wherein X is alkylene-O—, and $R^2$ is aryl. Another embodiment provides the compound having the structure of Formula (Ia), wherein X is alkylene-O—, and $R^2$ is heteroaryl. Another embodiment provides the compound having the structure of Formula (Ia), wherein X is alkylene-O—, and $R^2$ is carbocyclyl. Another embodiment provides the compound having the structure of Formula (Ia), wherein $R^2$ is $C_3$-$C_7$ carbocyclyl. Another embodiment provides the compound having the structure of Formula (Ia), wherein X is alkylene-O—, and $R^2$ is heterocyclyl. Another embodiment provides the compound having the structure of Formula (Ia), wherein the alkylene is a $C_1$-$C_3$ alkylene.

In some embodiments, the compound of Formula (I), (Ia), or (II) as disclosed herein has the structure provided in Table 1.

TABLE 1

| Chemical Synthesis Example | Structure | Name |
|---|---|---|
| 1 | 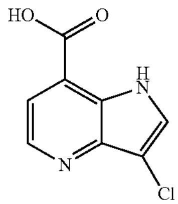 [SMILES: O=C(O)c1ccnc2c(Cl)c[nH]c12] | 3-chloro-1H-pyrrolo[3,2-b]pyridine-7-carboxylic acid |
| 2 | 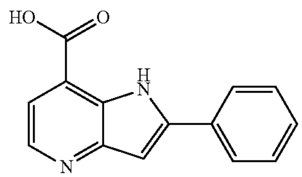 [SMILES: O=C(O)c1ccnc2cc(-c3ccccc3)[nH]c12] | 2-phenyl-1H-pyrrolo[3,2-b]pyridine-7-carboxylic acid |
| 3 | 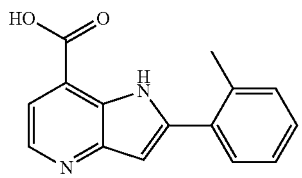 [SMILES: Cc1ccccc1-c1cc2nccc(C(=O)O)c2[nH]1] | 2-(2-methylphenyl)-1H-pyrrolo[3,2-b]pyridine-7-carboxylic acid |
| 6 | 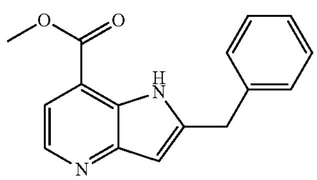 [SMILES: COC(=O)c1ccnc2cc(Cc3ccccc3)[nH]c12] | methyl 2-benzyl-1H-pyrrolo-[3,2-b]pyridine-7-carboxylate |
| 7 | 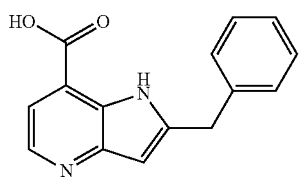 | 2-benzyl-1H-pyrrolo[3,2-b]pyridine-7-carboxylic acid |
| 8 | 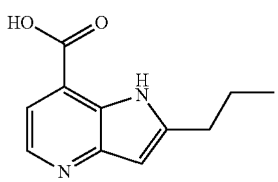 | 2-propyl-1H-pyrrolo[3,2-b]pyridine-7-carboxylic acid |
| 10 | 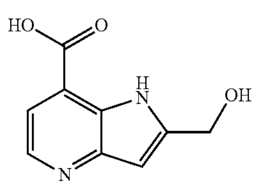 [SMILES: O=C(O)c1ccnc2cc(CO)[nH]c12] | 2-(hydroxymethyl)-1H-pyrrolo[3,2-b]pyridine-7-carboxylic acid |
| 11 | 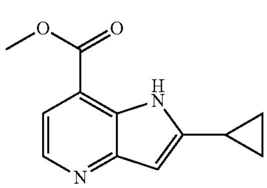 [SMILES: COC(=O)c1ccnc2cc(C3CC3)[nH]c12] | methyl 2-cyclopropyl-1H-pyrrolo[3,2-b]pyridine-7-carboxylate |

TABLE 1-continued

| Chemical Synthesis Example | Structure | Name |
|---|---|---|
| 12 | 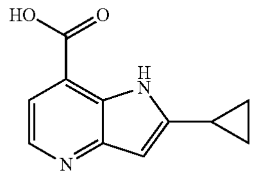 [SMILES: O=C(O)c1ccnc2cc(C3CC3)[nH]c12] | 2-cyclopropyl-1H-pyrrolo-[3,2-b]pyridine-7-carboxylic acid |
| 5 | 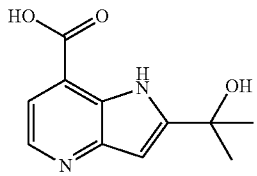 [SMILES: CC(C)(O)c1cc2nccc(C(=O)O)c2[nH]1] | 2-(2-hydroxypropan-2-yl)-1H-pyrrolo[3,2-b]pyridine-7-carboxylic acid |
| 4 | 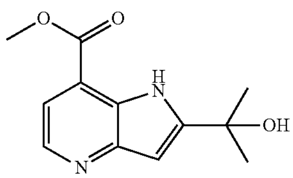 [SMILES: COC(=O)c1ccnc2cc(C(C)(C)O)[nH]c12] | methyl 2-(2-hydroxypropan-2-yl)-1H-pyrrolo[3,2-b]pyridine-7-carboxylate |
| 13 | 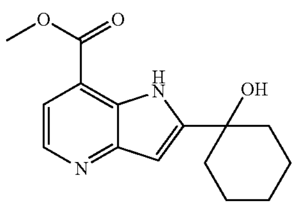 [SMILES: COC(=O)c1ccnc2cc(C3(O)CCCCC3)[nH]c12] | methyl 2-(1-hydroxycyclohexyl)-1H-pyrrolo[3,2-b]pyridine-7-carboxylate |
| 14 | 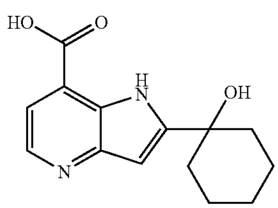 [SMILES: O=C(O)c1ccnc2cc(C3(O)CCCCC3)[nH]c12] | 2-(1-hydroxycyclohexyl)-1H-pyrrolo[3,2-b]pyridine-7-carboxylic acid |
| 15 | 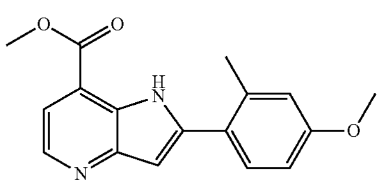 | methyl 2-(4-methoxy-2-methylphenyl)-1H-pyrrolo-[3,2-b]pyridine-7-carboxylate |
| 17 | 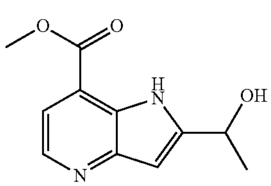 [SMILES: COC(=O)c1ccnc2cc(C(C)O)[nH]c12] | methyl 2-(1-hydroxyethyl)-1H-pyrrolo[3,2-b]pyridine-7-carboxylate |
| 18 | 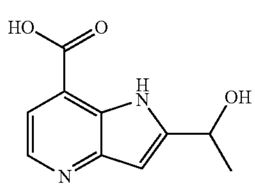 | 2-(1-hydroxyethyl)-1H-pyrrolo[3,2-b]pyridine-7-carboxylic acid |

TABLE 1-continued

| Chemical Synthesis Example | Structure | Name |
|---|---|---|
| 16 | 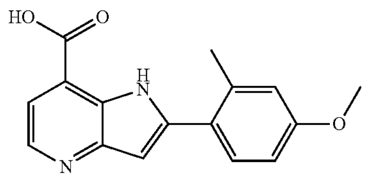 [SMILES: COc1ccc(-c2cc3nccc(C(=O)O)c3[nH]2)c(C)c1] | 2-(4-methoxy-2-methylphenyl)-1H-pyrrolo[3,2-b]pyridine-7-carboxylic acid |
| 20 | | 2-[hydroxy(phenyl)methyl]-1H-pyrrolo[3,2-b]pyridine-7-carboxylic acid |
| 22 | 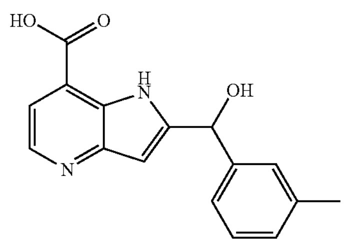 [SMILES: Cc1cccc(C(O)c2cc3nccc(C(=O)O)c3[nH]2)c1] | 2-[hydroxy-(3-methylphenyl)methyl]-1H-pyrrolo[3,2-b]pyridine-7-carboxylic acid |
| 24 | 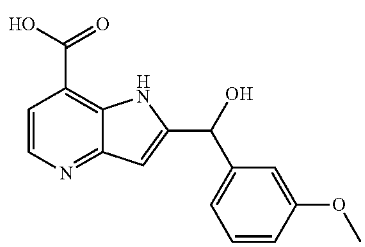 [SMILES: COc1cccc(C(O)c2cc3nccc(C(=O)O)c3[nH]2)c1] | 2-[hydroxy-(3-methoxyphenyl)methyl]-1H-pyrrolo[3,2-b]pyridine-7-carboxylate acid |
| 21 | 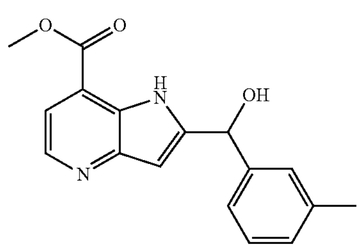 | methyl 2-[hydroxy-(3-methylphenyl)methyl]-1H-pyrrolo[3,2-b]pyridine-7-carboxylate |
| 20 | | methyl 2-[hydroxy(phenyl)methyl]-1H-pyrrolo[3,2-b]pyridine-7-carboxylate |

TABLE 1-continued

| Chemical Synthesis Example | Structure | Name |
|---|---|---|
| 9 | 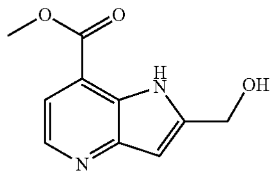 | methyl 2-(hydroxymethyl)-1H-pyrrolo[3,2-b]pyridine-7-carboxylate |
| 23 | 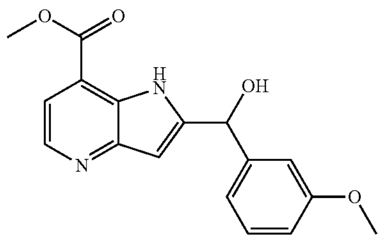 | methyl 2-[hydroxy-(3-methoxyphenyl)methyl]-1H-pyrrolo[3,2-b]pyridine-7-carboxylate |
| 25 | 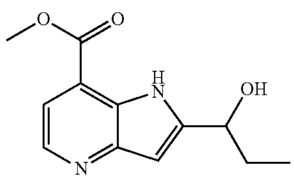 [SMILES: CCC(O)c1cc2nccc(C(=O)OC)c2[nH]1] | methyl 2-(1-hydroxypropyl)-1H-pyrrolo[3,2-b]pyridine-7-carboxylate |
| 27 | 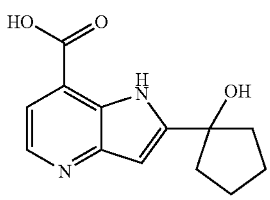 [SMILES: O=C(O)c1ccnc2cc(C3(O)CCCC3)[nH]c12] | 2-(1-hydroxycyclopentyl)-1H-pyrrolo[3,2-b]pyridine-7-carboxylic acid |
| 29 | 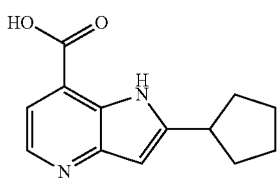 [SMILES: O=C(O)c1ccnc2cc(C3CCCC3)[nH]c12] | 2-cyclopentyl-1H-pyrrolo[3,2-b]pyridine-7-carboxylic acid |
| 28 | 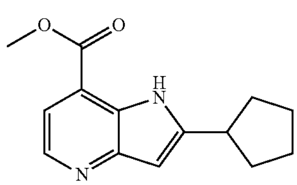 [SMILES: COC(=O)c1ccnc2cc(C3CCCC3)[nH]c12] | methyl 2-cyclopentyl-1H-pyrrolo[3,2-b]pyridine-7-carboxylate |
| 26 | 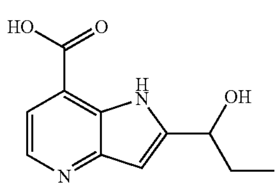 [SMILES: CCC(O)c1cc2nccc(C(=O)O)c2[nH]1] | 2-(1-hydroxypropyl)-1H-pyrrolo[3,2-b]pyridine-7-carboxylic acid |

TABLE 1-continued

| Chemical Synthesis Example | Structure | Name |
|---|---|---|
| 30 | 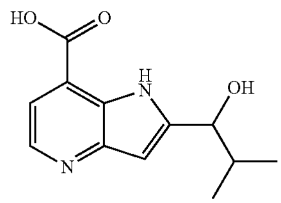 [SMILES: CC(C)C(O)c1cc2nccc(C(=O)O)c2[nH]1] | 2-(1-hydroxy-2-methylpropyl)-1H-pyrrolo[3,2-b]pyridine-7-carboxylic acid |
| 31 | 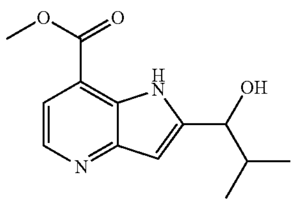 [SMILES: COC(=O)c1ccnc2cc(C(O)C(C)C)[nH]c12] | methyl 2-(1-hydroxy-2-methylpropyl)-1H-pyrrolo-[3,2-b]pyridine-7-carboxylate |
| 33 | 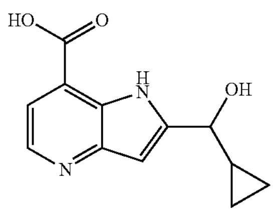 [SMILES: O=C(O)c1ccnc2cc(C(O)C3CC3)[nH]c12] | 2-[cyclopropyl(hydroxy)methyl]-1H-pyrrolo[3,2-b]pyridine-7-carboxylic acid |
| 32 | 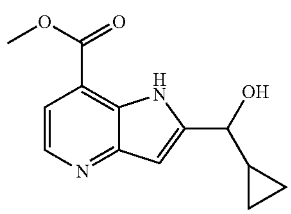 [SMILES: COC(=O)c1ccnc2cc(C(O)C3CC3)[nH]c12] | methyl 2-[cyclopropyl-(hydroxy)methyl]-1H-pyrrolo[3,2-b]pyridine-7-carboxylate |
| 34 | 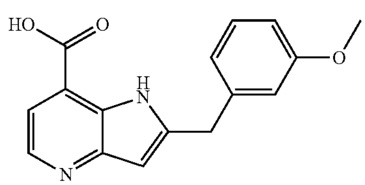 [SMILES: COc1cccc(Cc2cc3nccc(C(=O)O)c3[nH]2)c1] | 2-[(3-methoxyphenyl)methyl]-1H-pyrrolo[3,2-b]pyridine-7-carboxylic acid |
| 35 | 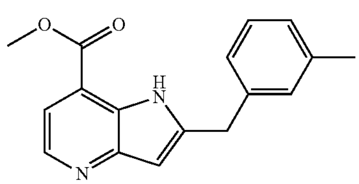 | methyl 2-[(3-methyl-phenyl)methyl]-1H-pyrrolo-[3,2-b]pyridine-7-carboxylate |
| 37 | 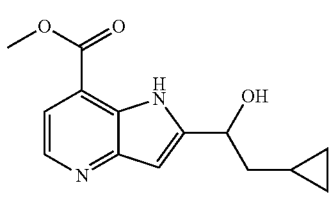 [SMILES: COC(=O)c1ccnc2cc(C(O)CC3CC3)[nH]c12] | methyl 2-(2-cyclopropyl-1-hydroxyethyl)-1H-pyrrolo-[3,2-b]pyridine-7-carboxylate |

TABLE 1-continued

| Chemical Synthesis Example | Structure | Name |
|---|---|---|
| 36 | 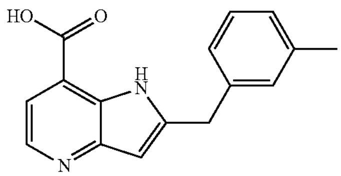 [SMILES: Cc1cccc(Cc2cc3nccc(C(=O)O)c3[nH]2)c1] | 2-[(3-methylphenyl)methyl]-1H-pyrrolo[3,2-b]pyridine-7-carboxylic acid |
| 38 | 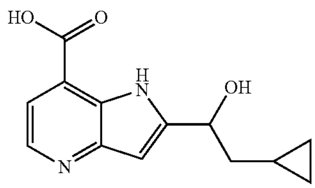 [SMILES: O=C(O)c1ccnc2cc(C(O)CC3CC3)[nH]c12] | 2-(2-cyclopropyl-1-hydroxyethyl)-1H-pyrrolo-[3,2-b]pyridine-7-carboxylic acid |
| 39 | 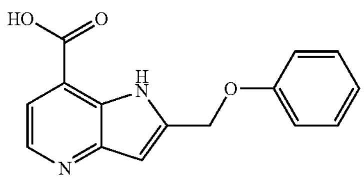 [SMILES: O=C(O)c1ccnc2cc(COc3ccccc3)[nH]c12] | 2-(phenoxymethyl)-1H-pyrrolo[3,2-b]pyridine-7-carboxylic acid |
| 41 | 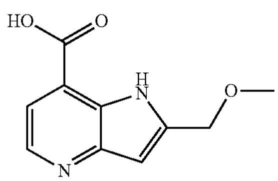 | 2-(methoxymethyl)-1H-pyrrolo[3,2-b]pyridine-7-carboxylic acid |
| 40 | 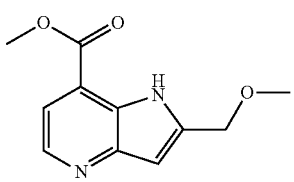 | methyl 2-(methoxymethyl)-1H-pyrrolo[3,2-b]pyridine-7-carboxylate |
| 43 | 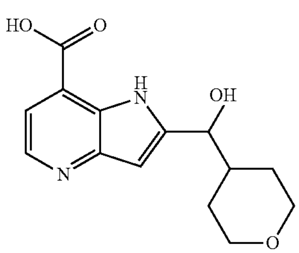 [SMILES: O=C(O)c1ccnc2cc(C(O)C3CCOCC3)[nH]c12] | 2-[hydroxy(oxan-4-yl)methyl]-1H-pyrrolo[3,2-b]pyridine-7-carboxylic acid |
| 42 | 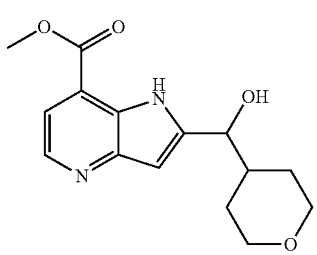 [SMILES: COC(=O)c1ccnc2cc(C(O)C3CCOCC3)[nH]c12] | methyl 2-[hydroxy(oxan-4-yl)-methyl]-1H-pyrrolo[3,2-b]-pyridine-7-carboxylate |

TABLE 1-continued

| Chemical Synthesis Example | Structure | Name |
|---|---|---|
| 44 | 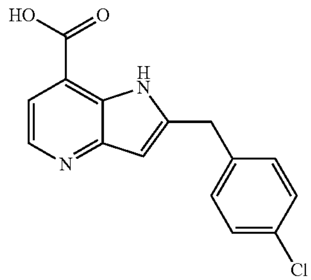 [SMILES: O=C(O)c1ccnc2cc(Cc3ccc(Cl)cc3)[nH]c12] | 2-[(4-chlorophenyl)methyl]-1H-pyrrolo[3,2-b]pyridine-7-carboxylic acid |
| 46 | 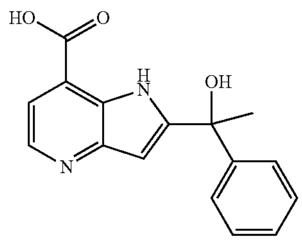 [SMILES: CC(O)(c1ccccc1)c1cc2nccc(C(=O)O)c2[nH]1] | 2-(1-hydroxy-1-phenylethyl)-1H-pyrrolo[3,2-b]pyridine-7-carboxylic acid |
| 45 | 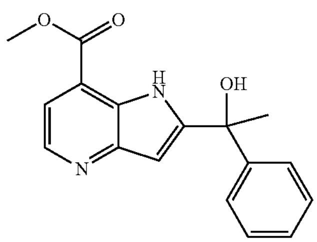 [SMILES: COC(=O)c1ccnc2cc(C(C)(O)c3ccccc3)[nH]c12] | methyl 2-(1-hydroxy-1-phenylethyl)-1H-pyrrolo[3,2-b]pyridine-7-carboxylate |
| 47 | 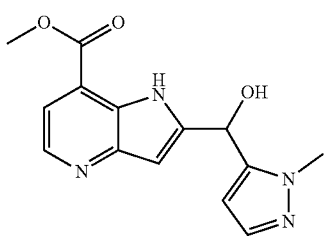 | methyl 2-[hydroxy-(2-methylpyrazol-3-yl)methyl]-1H-pyrrolo[3,2-b]pyridine-7-carboxylate |
| 49 | 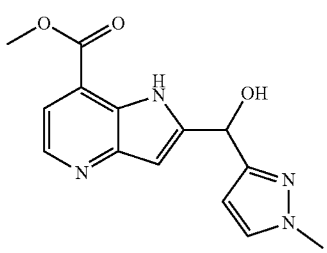 | 2-[hydroxy-(1-methylpyrazol-4-yl)methyl]-1H-pyrrolo[3,2-b]pyridine-7-carboxylate |
| 51 | 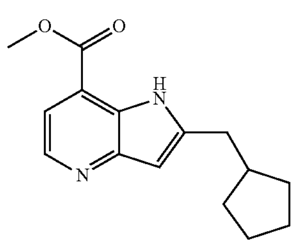 [SMILES: COC(=O)c1ccnc2cc(CC3CCCC3)[nH]c12] | methyl 2-(cyclopentylmethyl)-1H-pyrrolo[3,2-b]pyridine-7-carboxylate |

TABLE 1-continued

| Chemical Synthesis Example | Structure | Name |
|---|---|---|
| 48 | 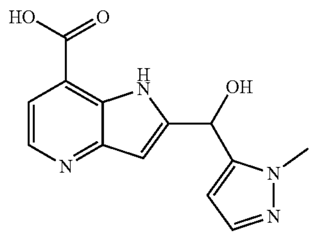 [SMILES: Cn1nccc1C(O)c1cc2nccc(C(=O)O)c2[nH]1] | 2-[hydroxy-(2-methylpyrazol-3-yl)methyl]-1H-pyrrolo[3,2-b]pyridine-7-carboxylic acid |
| 52 | 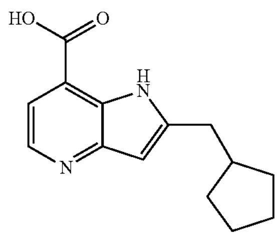 [SMILES: O=C(O)c1ccnc2cc(CC3CCCC3)[nH]c12] | 2-(cyclopentylmethyl)-1H-pyrrolo[3,2-b]pyridine-7-carboxylic acid |
| 53 | 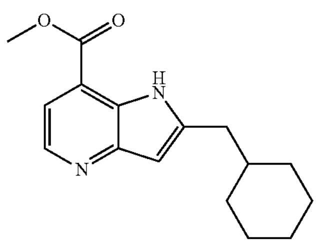 [SMILES: COC(=O)c1ccnc2cc(CC3CCCCC3)[nH]c12] | methyl 2-(cyclohexylmethyl)-1H-pyrrolo[3,2-b]pyridine-7-carboxylate |
| 54 | 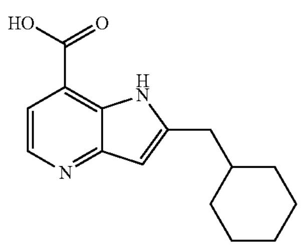 [SMILES: O=C(O)c1ccnc2cc(CC3CCCCC3)[nH]c12] | 2-(cyclohexylmethyl)-1H-pyrrolo[3,2-b]pyridine-7-carboxylic acid |
| 50 | 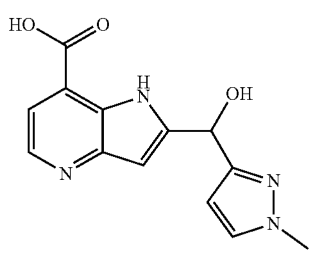 [SMILES: Cn1ccc(C(O)c2cc3nccc(C(=O)O)c3[nH]2)n1] | 2-[hydroxy-(1-methylpyrazol-4-yl)methyl]-1H-pyrrolo[3,2-b]pyridine-7-carboxylic acid |
| 55 | 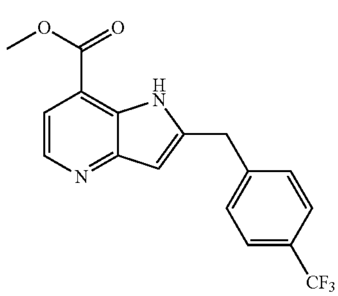 [SMILES: COC(=O)c1ccnc2cc(Cc3ccc(C(F)(F)F)cc3)[nH]c12] | methyl 2-[[4-(trifluoromethyl)phenyl]methyl]-1H-pyrrolo[3,2-b]pyridine-7-carboxylate |

TABLE 1-continued

| Chemical Synthesis Example | Structure | Name |
|---|---|---|
| 56 | 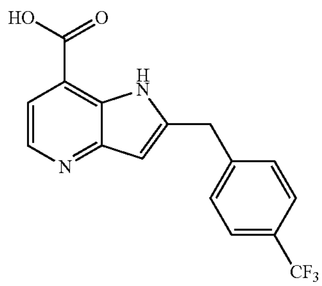 [SMILES: O=C(O)c1ccnc2cc(Cc3ccc(C(F)(F)F)cc3)[nH]c12] | 2-[[4-(trifluoromethyl)phenyl]methyl]-1H-pyrrolo-[3,2-b]-pyridine-7-carboxylic acid |
| 57 | 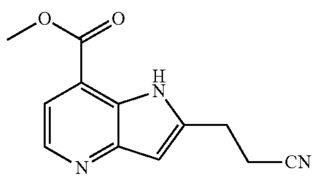 [SMILES: COC(=O)c1ccnc2cc(CCC#N)[nH]c12] | methyl 2-(2-cyanoethyl)-1H-pyrrolo[3,2-b]pyridine-7-carboxylate |
| 58 | 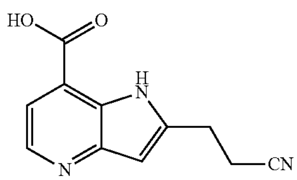 [SMILES: N#CCCc1cc2nccc(C(=O)O)c2[nH]1] | 2-(2-cyanoethyl)-1H-pyrrolo[3,2-b]-pyridine-7-carboxylic acid |
| 59 | 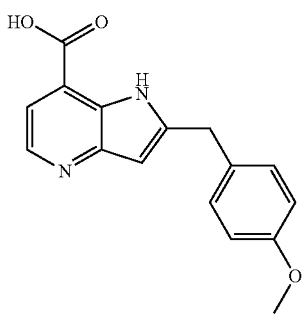 [SMILES: COc1ccc(Cc2cc3nccc(C(=O)O)c3[nH]2)cc1] | 2-[(4-methoxyphenyl)methyl]-1H-pyrrolo[3,2-b]pyridine-7-carboxylic acid |
| 60 | 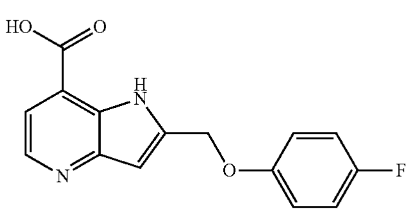 [SMILES: O=C(O)c1ccnc2cc(COc3ccc(F)cc3)[nH]c12] | 2-[(4-fluorophenoxy)methyl]-1H-pyrrolo[3,2-b]pyridine-7-carboxylic acid |
| 61 | 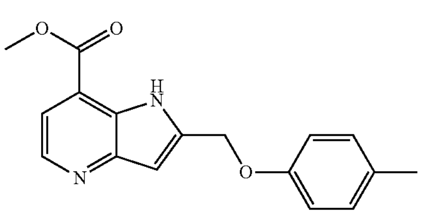 | methyl-2-[(4-methylphenoxy)methyl]-1H-pyrrolo[3,2-b]pyridine-7-carboxylate |

TABLE 1-continued

| Chemical Synthesis Example | Structure | Name |
|---|---|---|
| 62 | 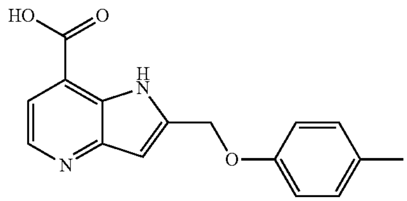 [SMILES: Cc1ccc(OCc2cc3nccc(C(=O)O)c3[nH]2)cc1] | 2-[(4-methylphenoxy)methyl]-1H-pyrrolo[3,2-b]pyridine-7-carboxylic acid |
| 63 | 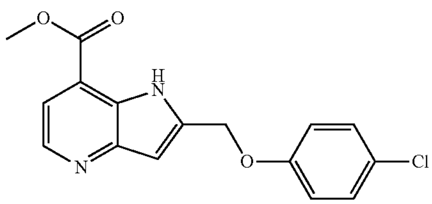 [SMILES: COC(=O)c1ccnc2cc(COc3ccc(Cl)cc3)[nH]c12] | methyl-2-[(4-chlorophenoxy)methyl]-1H-pyrrolo[3,2-b]pyridine-7-carboxylate |
| 64 | 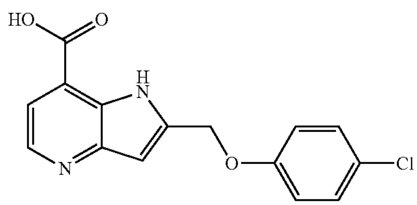 [SMILES: O=C(O)c1ccnc2cc(COc3ccc(Cl)cc3)[nH]c12] | 2-[(4-chlorophenoxy)methyl]-1H-pyrrolo[3,2-b]pyridine-7-carboxylic acid |
| 66 | 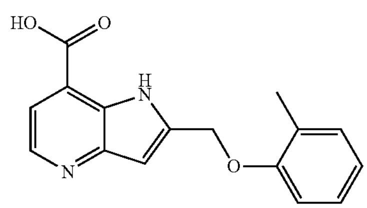 [SMILES: Cc1ccccc1OCc1cc2nccc(C(=O)O)c2[nH]1] | 2-[(2-methylphenoxy)methyl]-1H-pyrrolo[3,2-b]pyridine-7-carboxylic acid |
| 65 | 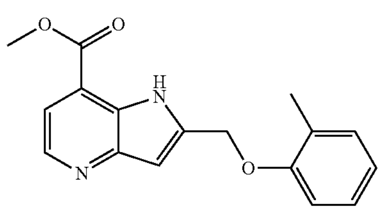 [SMILES: COC(=O)c1ccnc2cc(COc3ccccc3C)[nH]c12] | methyl 2-[(2-methylphenoxy)methyl]-1H-pyrrolo-[3,2-b]pyridine-7-carboxylate |
| 68 | 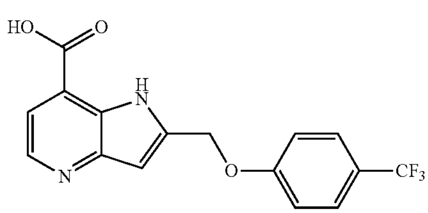 [SMILES: O=C(O)c1ccnc2cc(COc3ccc(C(F)(F)F)cc3)[nH]c12] | 2-[[4-(trifluoromethyl)phenoxy]methyl]-1H-pyrrolo-[3,2-b]pyridine-7-carboxylic acid |
| 67 | 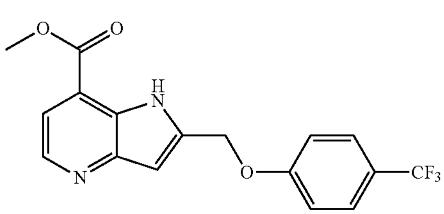 [SMILES: COC(=O)c1ccnc2cc(COc3ccc(C(F)(F)F)cc3)[nH]c12] | methyl 2-[[4-(trifluoromethyl)phenoxy]methyl]-1H-pyrrolo[3,2-b]pyridine-7-carboxylate |

TABLE 1-continued

| Chemical Synthesis Example | Structure | Name |
|---|---|---|
| 70 | 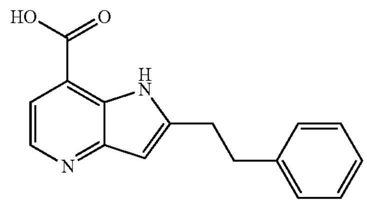 | 2-(2-phenylethyl)-1H-pyrrolo[3,2-b]pyridine-7-carboxylic acid |
| 69 | 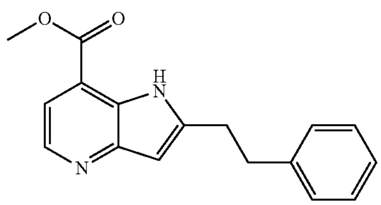 [SMILES: COC(=O)c1ccnc2cc(CCc3ccccc3)[nH]c12] | methyl 2-(2-phenylethyl)-1H-pyrrolo[3,2-b]pyridine-7-carboxylate |
| 72 | 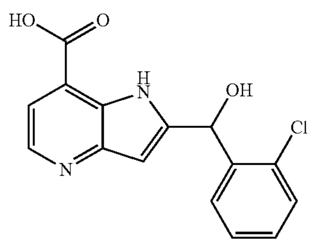 [SMILES: O=C(O)c1ccnc2cc(C(O)c3ccccc3Cl)[nH]c12] | 2-[(2-chlorophenyl)-hydroxy-methyl]-1H-pyrrolo[3,2-b]-pyridine-7-carboxylic acid |
| 71 | 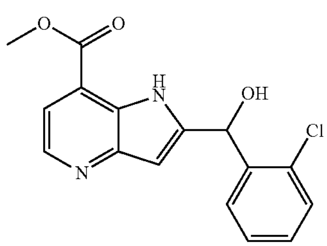 [SMILES: COC(=O)c1ccnc2cc(C(O)c3ccccc3Cl)[nH]c12] | methyl 2-[(2-chlorophenyl)-hydroxymethyl]-1H-pyrrolo[3,2-b]-pyridine-7-carboxylate |
| 73 | 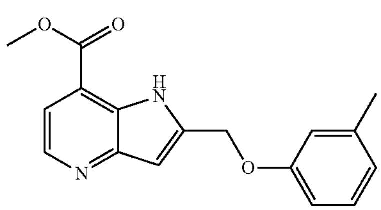 | methyl 2-[(3-methylphenoxy)-methyl]-1H-pyrrolo[3,2-b]-pyridine-7-carboxylate |
| 74 | 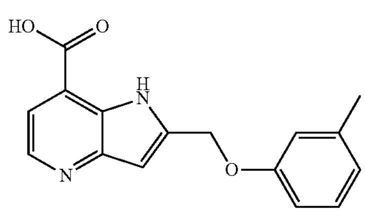 [SMILES: Cc1cccc(OCc2cc3nccc(C(=O)O)c3[nH]2)c1] | 2-[(3-methylphenoxy)methyl]-1H-pyrrolo[3,2-b]pyridine-7-carboxylic acid |
| 75 | 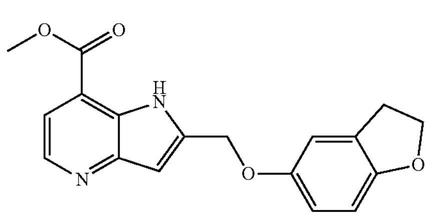 [SMILES: COC(=O)c1ccnc2cc(COc3ccc4c(c3)CCO4)[nH]c12] | methyl 2-(2,3-dihydro-1-benzofuran-5-yloxymethyl)-1H-pyrrolo[3,2-b]pyridine-7-carboxylate |

TABLE 1-continued

| Chemical Synthesis Example | Structure | Name |
|---|---|---|
| 76 | 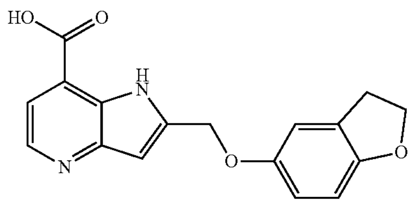 [SMILES: O=C(O)c1ccnc2cc(COc3ccc4c(c3)CCO4)[nH]c12] | 2-(2,3-dihydro-1-benzofuran-5-yloxymethyl)-1H-pyrrolo[3,2-b]-pyridine-7-carboxylic acid |
| 77 | 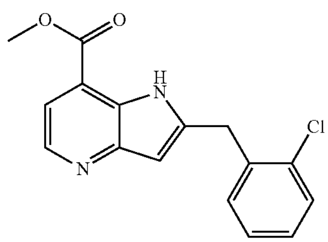 [SMILES: COC(=O)c1ccnc2cc(Cc3ccccc3Cl)[nH]c12] | methyl 2-[(2-chlorophenyl)-methyl]-1H-pyrrolo[3,2-b]-pyridine-7-carboxylate |
| 78 | 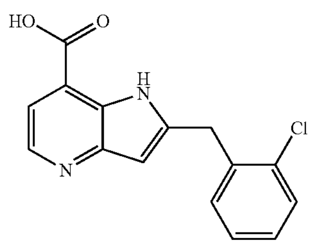 [SMILES: O=C(O)c1ccnc2cc(Cc3ccccc3Cl)[nH]c12] | 2-[(2-chlorophenyl)methyl]-1H-pyrrolo[3,2-b]pyridine-7-carboxylic acid |
| 79 | 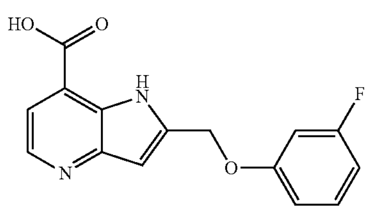 [SMILES: O=C(O)c1ccnc2cc(COc3cccc(F)c3)[nH]c12] | 2-[(3-fluorophenoxy)methyl]-1H-pyrrolo[3,2-b]pyridine-7-carboxylic acid |
| 80 | 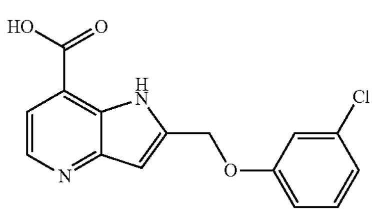 [SMILES: O=C(O)c1ccnc2cc(COc3cccc(Cl)c3)[nH]c12] | 2-[(3-chlorophenoxy)methyl]-1H-pyrrolo[3,2-b]pyridine-7-carboxylic acid |
| 81 | 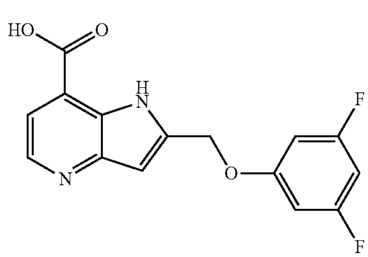 [SMILES: O=C(O)c1ccnc2cc(COc3cc(F)cc(F)c3)[nH]c12] | 2-[(3,5-difluorophenoxy)methyl]-1H-pyrrolo[3,2-b]pyridine-7-carboxylic acid |

TABLE 1-continued

| Chemical Synthesis Example | Structure | Name |
|---|---|---|
| 82 | 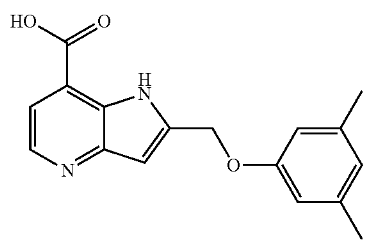 [SMILES: Cc1cc(C)cc(OCc2cc3nccc(C(=O)O)c3[nH]2)c1] | 2-[(3,5-dimethylphenoxy)methyl]-1H-pyrrolo[3,2-b]-pyridine-7-carboxylic acid |
| 83 | 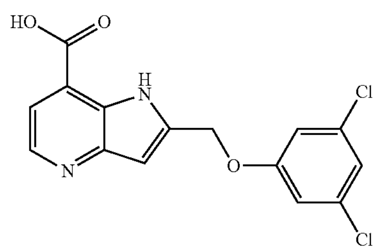 [SMILES: O=C(O)c1ccnc2cc(COc3cc(Cl)cc(Cl)c3)[nH]c12] | 2-[(3,5-dichlorophenoxy)methyl]-1H-pyrrolo[3,2-b]pyridine-7-carboxylic acid |
| 84 | 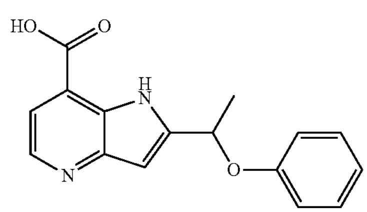 [SMILES: CC(Oc1ccccc1)c1cc2nccc(C(=O)O)c2[nH]1] | 2-(1-phenoxyethyl)-1H-pyrrolo[3,2-b]pyridine-7-carboxylic acid |
| 85 | 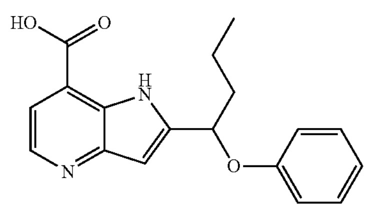 [SMILES: CCCC(Oc1ccccc1)c1cc2nccc(C(=O)O)c2[nH]1] | 2-(1-phenoxybutyl)-1H-pyrrolo[3,2-b]pyridine-7-carboxylic acid |
| 86 | 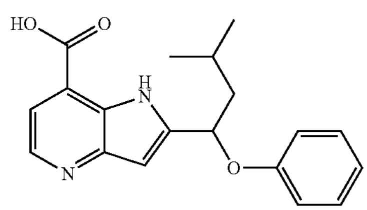 [SMILES: CC(C)CC(Oc1ccccc1)c1cc2nccc(C(=O)O)c2[nH]1] | 2-(3-methyl-1-phenoxybutyl)-1H-pyrrolo[3,2-b]pyridine-7-carboxylic acid |
| 87 | 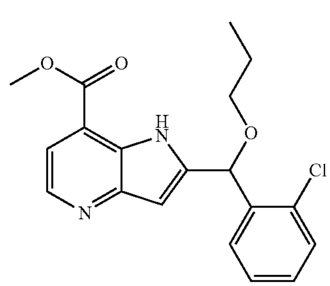 [SMILES: CCCOC(c1cc2nccc(C(=O)OC)c2[nH]1)c1ccccc1Cl] | methyl 2-[(2-chlorophenyl)propoxymethyl]-1H-pyrrolo-[3,2-b]pyridine-7-carboxylate |

TABLE 1-continued

| Chemical Synthesis Example | Structure | Name |
|---|---|---|
| 88 | 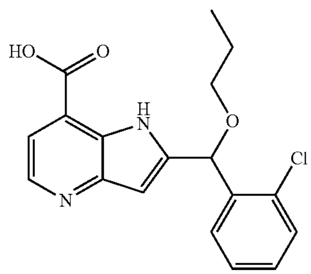 [SMILES: CCCOC(c1cc2nccc(C(=O)O)c2[nH]1)c1ccccc1Cl] | 2-[(2-chlorophenyl)-propoxy-methyl]-1H-pyrrolo[3,2-b]-pyridine-7-carboxylic acid |
| 89 | 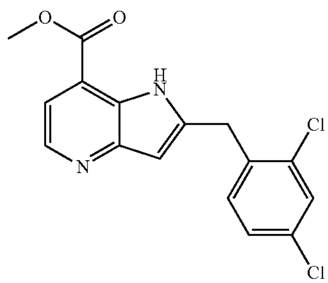 [SMILES: COC(=O)c1ccnc2cc(Cc3ccc(Cl)cc3Cl)[nH]c12] | methyl 2-[(2,4-dichloro-phenyl)methyl]-1H-pyrrolo-[3,2-b]-pyridine-7-carboxylate |
| 90 | 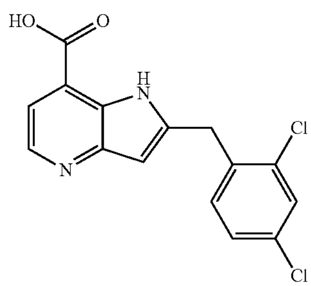 [SMILES: O=C(O)c1ccnc2cc(Cc3ccc(Cl)cc3Cl)[nH]c12] | 2-[(2,4-dichlorophenyl)methyl]-1H-pyrrolo[3,2-b]pyridine-7-carboxylic acid |
| 91 | 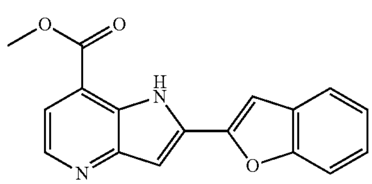 [SMILES: COC(=O)c1ccnc2cc(-c3cc4ccccc4o3)[nH]c12] | methyl 2-(1-benzofuran-2-yl)-1H-pyrrolo[3,2-b]pyridine-7-carboxylate |
| 92 | 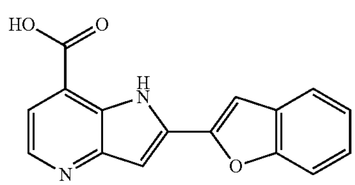 [SMILES: O=C(O)c1ccnc2cc(-c3cc4ccccc4o3)[nH]c12] | 2-(1-benzofuran-2-yl)-1H-pyrrolo[3,2-b]pyridine-7-carboxylic acid |
| 93 | 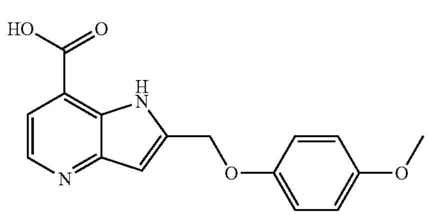 [SMILES: COc1ccc(OCc2cc3nccc(C(=O)O)c3[nH]2)cc1] | 2-[(4-methoxyphenoxy)methyl]-1H-pyrrolo[3,2-b]pyridine-7-carboxylic acid |

TABLE 1-continued

| Chemical Synthesis Example | Structure | Name |
|---|---|---|
| 94 | 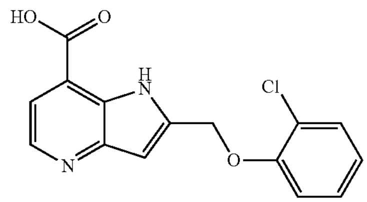 [SMILES: O=C(O)c1ccnc2cc(COc3ccccc3Cl)[nH]c12] | 2-[(2-chlorophenoxy)methyl]-1H-pyrrolo[3,2-b]pyridine-7-carboxylic acid |
| 95 | 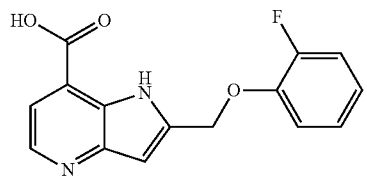 [SMILES: O=C(O)c1ccnc2cc(COc3ccccc3F)[nH]c12] | 2-[(2-fluorophenoxy)methyl]-1H-pyrrolo[3,2-b]pyridine-7-carboxylic acid |
| 96 | 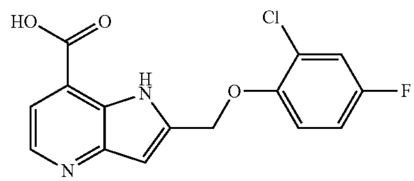 [SMILES: O=C(O)c1ccnc2cc(COc3ccc(F)cc3Cl)[nH]c12] | 2-[(2-chloro-4-fluorophenoxy)methyl]-1H-pyrrolo-[3,2-b]pyridine-7-carboxylic acid |
| 97 | 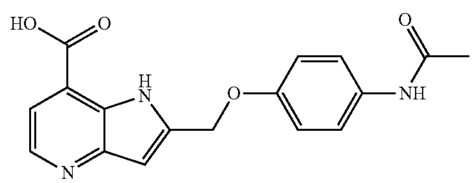 [SMILES: CC(=O)Nc1ccc(OCc2cc3nccc(C(=O)O)c3[nH]2)cc1] | 2-[(4-acetamidophenoxy)methyl]-1H-pyrrolo[3,2-b]pyridine-7-carboxylic acid |
| 98 | 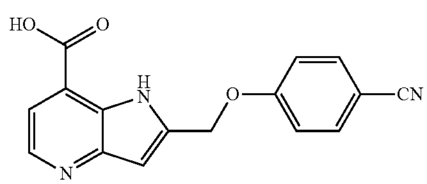 [SMILES: N#Cc1ccc(OCc2cc3nccc(C(=O)O)c3[nH]2)cc1] | 2-[(4-cyanophenoxy)methyl]-1H-pyrrolo[3,2-b]pyridine-7-carboxylic acid |
| 99 | 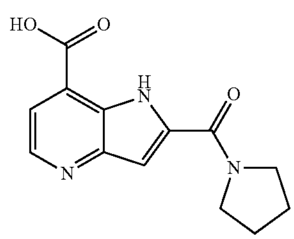 [SMILES: O=C(O)c1ccnc2cc(C(=O)N3CCCC3)[nH]c12] | 2-(pyrrolidin-1-ylcarbonyl)-1H-pyrrolo[3,2-b]pyridine-7-carboxylic acid |
| 100 | 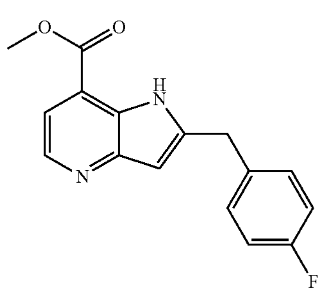 [SMILES: COC(=O)c1ccnc2cc(Cc3ccc(F)cc3)[nH]c12] | methyl 2-[(4-fluorophenyl)methyl]pyrrolo[3,2-b]pyridine-7-carboxylate |

TABLE 1-continued

| Chemical Synthesis Example | Structure | Name |
|---|---|---|
| 101 | 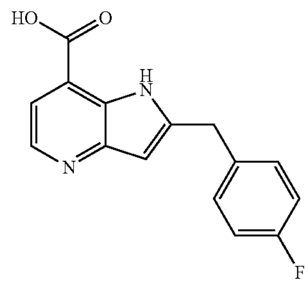 [SMILES: O=C(O)c1ccnc2cc(Cc3ccc(F)cc3)[nH]c12] | 2-[(4-fluorophenyl)methyl]-pyrrolo[3,2-b]pyridine-7-carboxylic acid |
| 102 | 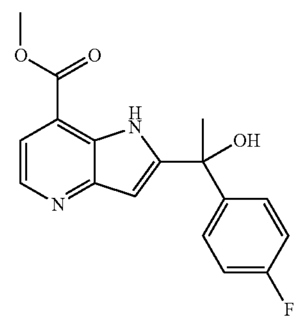 [SMILES: COC(=O)c1ccnc2cc(C(C)(O)c3ccc(F)cc3)[nH]c12] | methyl 2-[1-(4-fluorophenyl)-1-hydroxyethyl]-1H-pyrrolo[3,2-b]-pyridine-7-carboxylate |
| 103 | 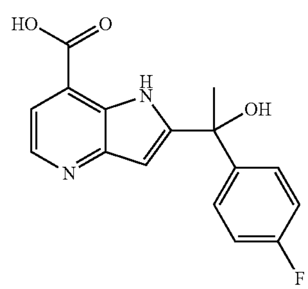 [SMILES: CC(O)(c1ccc(F)cc1)c1cc2nccc(C(=O)O)c2[nH]1] | 2-[1-(4-fluorophenyl)-1-hydroxyethyl]-1H-pyrrolo[3,2-b]-pyridine-7-carboxylic acid |
| 104 | 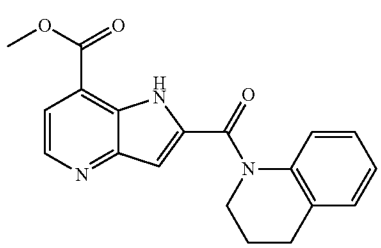 [SMILES: COC(=O)c1ccnc2cc(C(=O)N3CCCc4ccccc43)[nH]c12] | methyl 2-(1,2,3,4-tetrahydro-quinolylcarbonyl)pyrrolo[3,2-b]-pyridine-7-carboxylate |
| 105 | 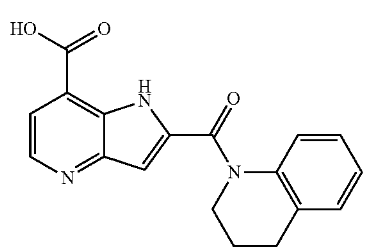 [SMILES: O=C(O)c1ccnc2cc(C(=O)N3CCCc4ccccc43)[nH]c12] | 2-(1,2,3,4-tetrahydroquinolylcarbonyl)-pyrrolo[3,2-b]-pyridine-7-carboxylic acid |

TABLE 1-continued

| Chemical Synthesis Example | Structure | Name |
|---|---|---|
| 106 | 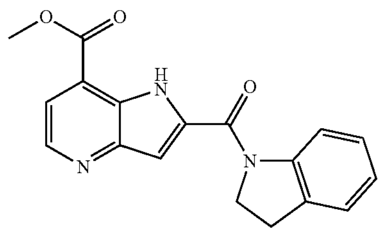 [SMILES: COC(=O)c1ccnc2cc(C(=O)N3CCc4ccccc43)[nH]c12] | methyl 2-(indolinylcarbonyl)-pyrrolo[3,2-b]pyridine-7-carboxylate |
| 107 | 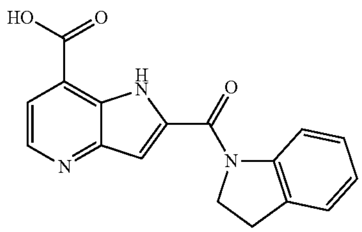 [SMILES: O=C(O)c1ccnc2cc(C(=O)N3CCc4ccccc43)[nH]c12] | 2-(indolinylcarbonyl)pyrrolo[3,2-b]-pyridine-7-carboxylic acid |
| 108 | 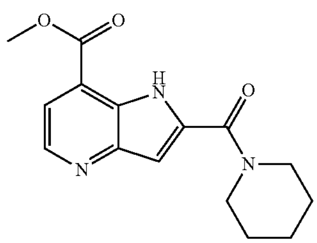 [SMILES: COC(=O)c1ccnc2cc(C(=O)N3CCCCC3)[nH]c12] | methyl 2-(piperidyl-carbonyl)-pyrrolo[3,2-b]pyridine-7-carboxylate |
| 109 | 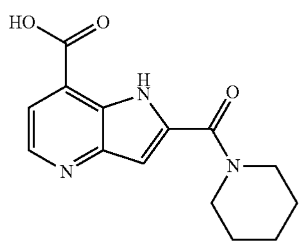 [SMILES: O=C(O)c1ccnc2cc(C(=O)N3CCCCC3)[nH]c12] | 2-(piperidylcarbonyl)pyrrolo[3,2-b]pyridine-7-carboxylic acid |
| 110 | 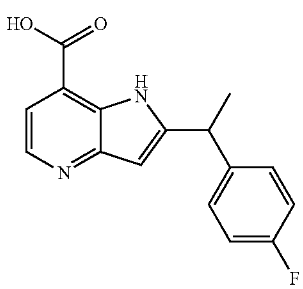 [SMILES: CC(c1ccc(F)cc1)c1cc2nccc(C(=O)O)c2[nH]1] | 2-[1-(4-fluorophenyl)ethyl]-1H-pyrrolo[3,2-b]pyridine-7-carboxylic acid |
| 111 | 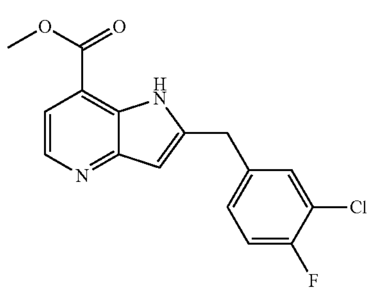 [SMILES: COC(=O)c1ccnc2cc(Cc3ccc(F)c(Cl)c3)[nH]c12] | methyl-2-(3-chloro-4-fluorobenzyl)-1H-pyrrolo[3,2-b]-pyridine-7-carboxylate |

TABLE 1-continued

| Chemical Synthesis Example | Structure | Name |
|---|---|---|
| 112 | 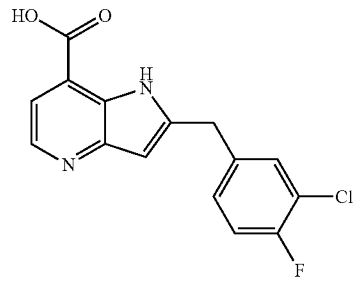 [SMILES: O=C(O)c1ccnc2cc(Cc3ccc(F)c(Cl)c3)[nH]c12] | 2-(3-chloro-4-fluorobenzyl)-1H-pyrrolo[3,2-b]pyridine-7-carboxylic acid |
| 113 | 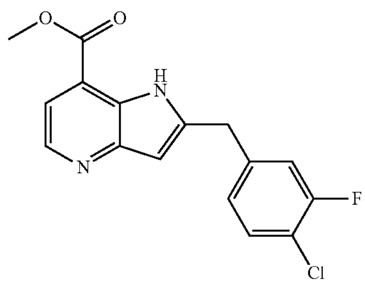 [SMILES: COC(=O)c1ccnc2cc(Cc3ccc(Cl)c(F)c3)[nH]c12] | methyl 2-(4-chloro-3-fluorobenzyl)-1H-pyrrolo[3,2-b]-pyridine-7-carboxylate |
| 114 | 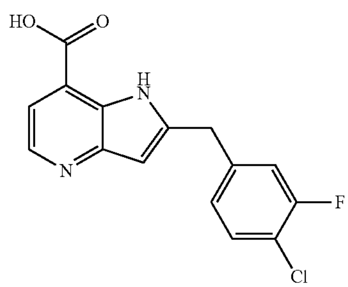 | 2-(4-chloro-3-fluorobenzyl)-1H-pyrrolo[3,2-b]pyridine-7-carboxylic acid |
| 115 | 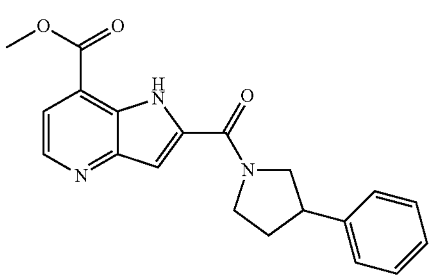 [SMILES: COC(=O)c1ccnc2cc(C(=O)N3CCC(c4ccccc4)C3)[nH]c12] | methyl 2-[(3-phenylpyrrolidinyl)-carbonyl]pyrrolo[3,2-b]pyridine-7-carboxylate |
| 116 | 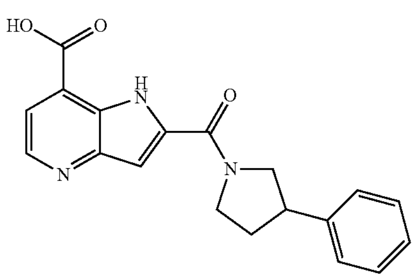 [SMILES: O=C(O)c1ccnc2cc(C(=O)N3CCC(c4ccccc4)C3)[nH]c12] | 2-[(3-phenylpyrrolidinyl)-carbonyl]pyrrolo[3,2-b]pyridine-7-carboxylic acid |

TABLE 1-continued

| Chemical Synthesis Example | Structure | Name |
|---|---|---|
| 117 | 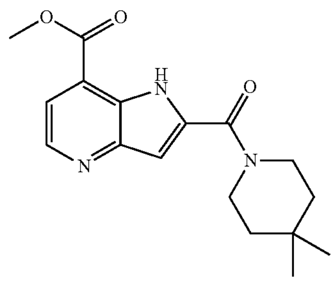 | methyl 2-[(4,4-dimethyl-piperidyl)carbonyl]pyrrolo[3,2-b]-pyridine-7-carboxylate |
| 118 | 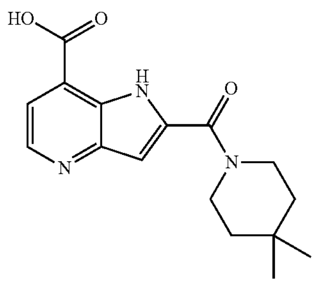 [SMILES: CC1(C)CCN(C(=O)c2cc3nccc(C(=O)O)c3[nH]2)CC1] | 2-[(4,4-dimethylpiperidyl)carbonyl]pyrrolo[3,2-b]pyridine-7-carboxylic acid |
| 119 | 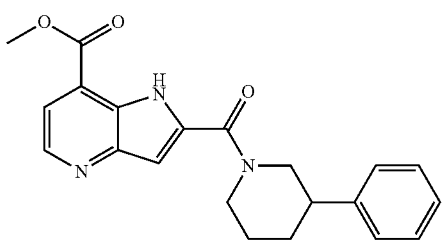 [SMILES: COC(=O)c1ccnc2cc(C(=O)N3CCCC(c4ccccc4)C3)[nH]c12] | methyl 2-[(3-phenylpiperidyl)carbonyl]pyrrolo[3,2-b]pyridine-7-carboxylate |
| 120 | 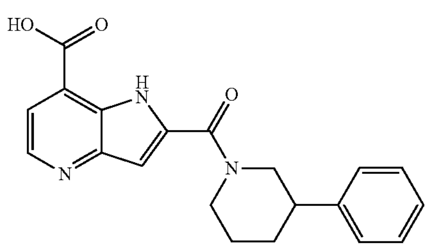 [SMILES: O=C(O)c1ccnc2cc(C(=O)N3CCCC(c4ccccc4)C3)[nH]c12] | 2-[(3-phenylpiperidyl)carbonyl]pyrrolo[3,2-b]pyridine-7-carboxylic acid |
| 121 | 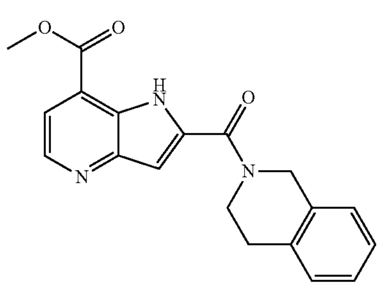 [SMILES: COC(=O)c1ccnc2cc(C(=O)N3CCc4ccccc4C3)[nH]c12] | methyl 2-(2-1,2,3,4-tetrahydro-isoquinolylcarbonyl)pyrrolo-[3,2-b]-pyridine-7-carboxylate |

TABLE 1-continued

| Chemical Synthesis Example | Structure | Name |
|---|---|---|
| 122 | 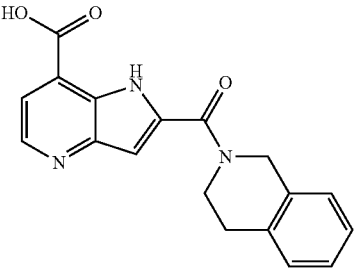 [SMILES: O=C(O)c1ccnc2cc(C(=O)N3CCc4ccccc4C3)[nH]c12] | 2-(2-1,2,3,4-tetrahydro-isoquinolylcarbonyl)pyrrolo-[3,2-b]pyridine-7-carboxylic acid |
| 123 | 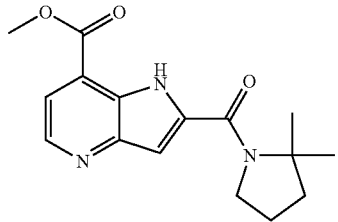 | methyl 2-[(2,2-dimethyl-pyrrolidinyl)carbonyl]pyrrolo-[3,2-b]-pyridine-7-carboxylate |
| 124 | 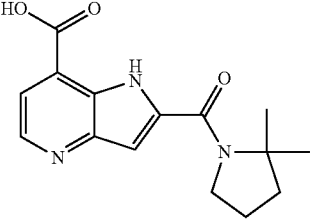 [SMILES: CC1(C)CCCN1C(=O)c1cc2nccc(C(=O)O)c2[nH]1] | 2-[(2,2-dimethylpyrrolidinyl)-carbonyl]pyrrolo[3,2-b]pyridine-7-carboxylic acid |
| 125 | 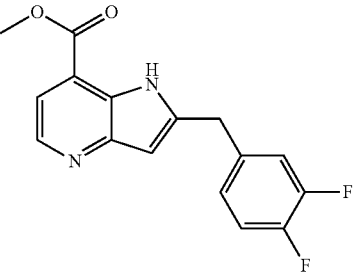 [SMILES: COC(=O)c1ccnc2cc(Cc3ccc(F)c(F)c3)[nH]c12] | methyl 2-(3,4-difluorobenzyl)-1H-pyrrolo[3,2-b]pyridine-7-carboxylate |
| 126 | 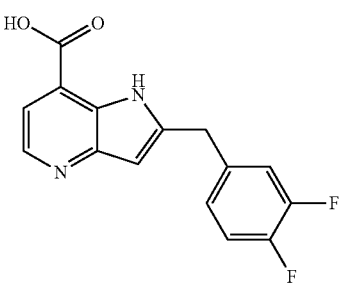 [SMILES: O=C(O)c1ccnc2cc(Cc3ccc(F)c(F)c3)[nH]c12] | 2-(3,4-difluorobenzyl)-1H-pyrrolo[3,2-b]pyridine-7-carboxylic acid |

TABLE 1-continued

| Chemical Synthesis Example | Structure | Name |
|---|---|---|
| 127 | 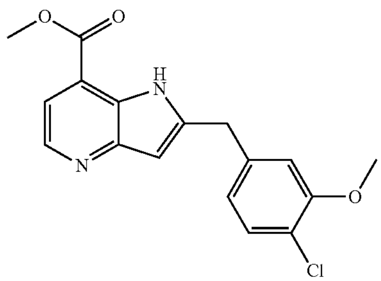 | methyl 2-(4-chloro-3-methoxybenzyl)-1H-pyrrolo-[3,2-b]-pyridine-7-carboxylate |
| 128 | 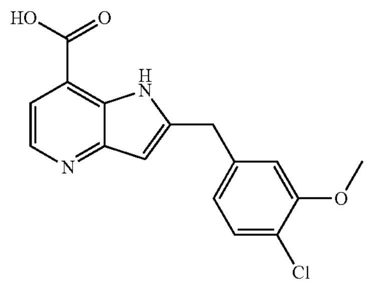 [SMILES: COc1cc(Cc2cc3nccc(C(=O)O)c3[nH]2)ccc1Cl] | 2-(4-chloro-3-methoxybenzyl)-1H-pyrrolo[3,2-b]pyridine-7-carboxylic acid |
| 129 | 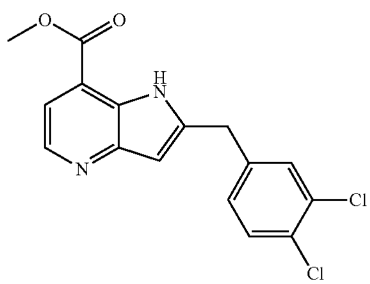 [SMILES: COC(=O)c1ccnc2cc(Cc3ccc(Cl)c(Cl)c3)[nH]c12] | methyl 2-(3,4-dichlorobenzyl)-1H-pyrrolo[3,2-b]pyridine-7-carboxylate |
| 130 | 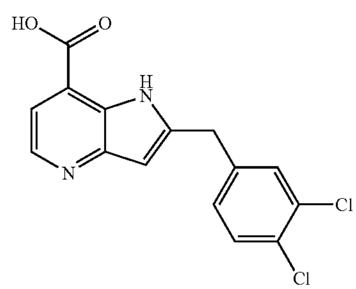 [SMILES: O=C(O)c1ccnc2cc(Cc3ccc(Cl)c(Cl)c3)[nH]c12] | 2-(3,4-dichlorobenzyl)-1H-pyrrolo[3,2-b]pyridine-7-carboxylic acid |
| 131 | 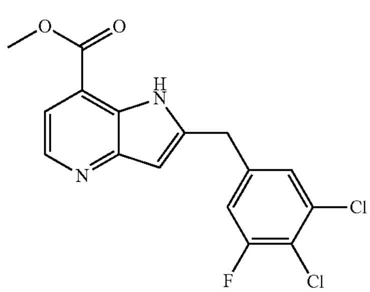 [SMILES: COC(=O)c1ccnc2cc(Cc3cc(F)c(Cl)c(Cl)c3)[nH]c12] | methyl 2-(3,4-dichloro-5-fluorobenzyl)-1H-pyrrolo-[3,2-b]pyridine-7-carboxylate |

TABLE 1-continued

| Chemical Synthesis Example | Structure | Name |
|---|---|---|
| 132 | 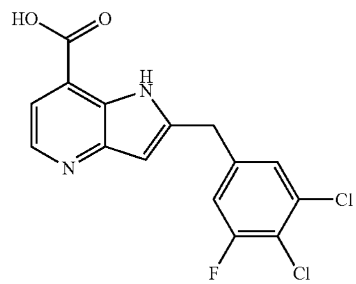 [SMILES: O=C(O)c1ccnc2cc(Cc3cc(F)c(Cl)c(Cl)c3)[nH]c12] | 2-(3,4-dichloro-5-fluorobenzyl)-1H-pyrrolo[3,2-b]pyridine-7-carboxylic acid |
| 133 | 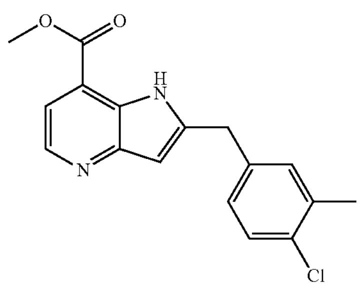 | methyl-2-(4-chloro-3-methylbenzyl)-1H-pyrrolo-[3,2-b]pyridine-7-carboxylate |
| 134 | 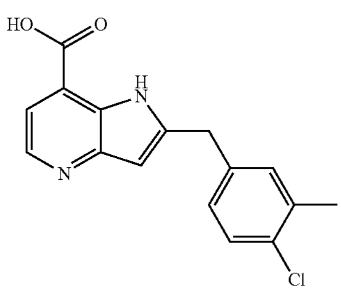 [SMILES: Cc1cc(Cc2cc3nccc(C(=O)O)c3[nH]2)ccc1Cl] | 2-(4-chloro-3-methylbenzyl)-1H-pyrrolo[3,2-b]pyridine-7-carboxylic acid |
| 135 | 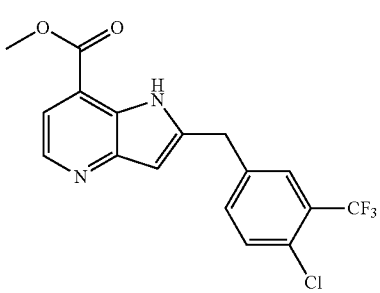 | methyl 2-[4-chloro-3-(trifluoromethyl)benzyl]-1H-pyrrolo[3,2-b]pyridine-7-carboxylate |
| 136 | 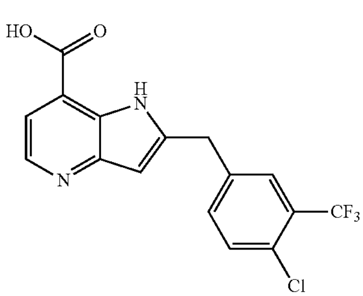 [SMILES: O=C(O)c1ccnc2cc(Cc3ccc(Cl)c(C(F)(F)F)c3)[nH]c12] | 2-[4-chloro-3-(trifluoromethyl)benzyl]-1H-pyrrolo-[3,2-b]pyridine-7-carboxylic acid |

TABLE 1-continued

| Chemical Synthesis Example | Structure | Name |
|---|---|---|
| 137 | 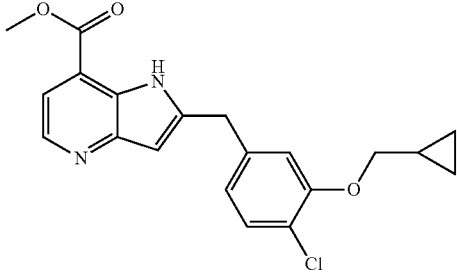 [SMILES: COC(=O)c1ccnc2cc(Cc3ccc(Cl)c(OCC4CC4)c3)[nH]c12] | methyl 2-[4-chloro-3-(cyclo-propylmethoxy)benzyl]-1H-pyrrolo[3,2-b]pyridine-7-carboxylate |
| 138 | 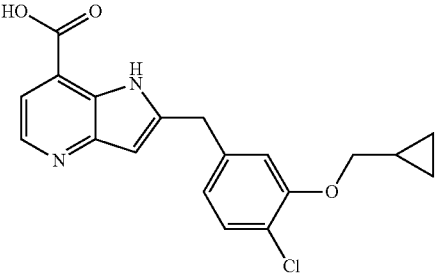 [SMILES: O=C(O)c1ccnc2cc(Cc3ccc(Cl)c(OCC4CC4)c3)[nH]c12] | 2-[4-chloro-3-(cyclopropyl-methoxy)benzyl]-1H-pyrrolo[3,2-b] pyridine-7-carboxylic acid |
| 139 | 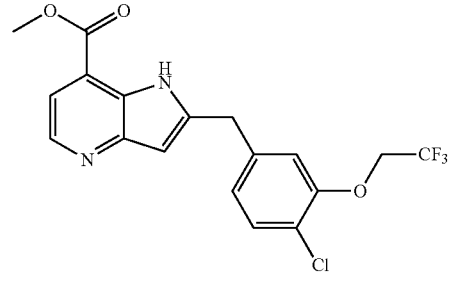 [SMILES: COC(=O)c1ccnc2cc(Cc3ccc(Cl)c(OCC(F)(F)F)c3)[nH]c12] | methyl-2-[4-chloro-3-(2,2,2-trifluoroethoxy)benzyl]-1H-pyrrolo[3,2-b]pyridine-7-carboxylate |
| 140 | 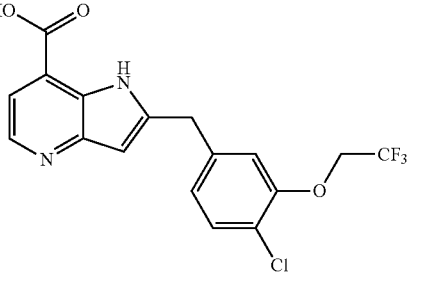 | 2-[4-chloro-3-(2,2,2-trifluoroethoxy)benzyl]-1H-pyrrolo[3,2-b]pyridine-7-carboxylic acid |
| 141 | 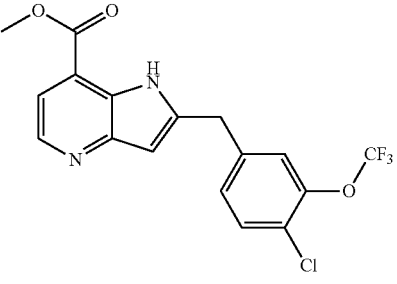 [SMILES: COC(=O)c1ccnc2cc(Cc3ccc(Cl)c(OC(F)(F)F)c3)[nH]c12] | methyl-2-[4-chloro-3-(trifluoromethoxy)benzyl]-1H-pyrrolo[3,2-b]pyridine-7-carboxylate |

TABLE 1-continued

| Chemical Synthesis Example | Structure | Name |
|---|---|---|
| 142 | 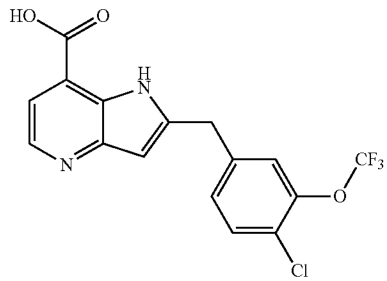 [SMILES: O=C(O)c1ccnc2cc(Cc3ccc(Cl)c(OC(F)(F)F)c3)[nH]c12] | 2-[4-chloro-3-(trifluoro-methoxy)benzyl]-1H-pyrrolo-[3,2-b]pyridine-7-carboxylic acid |
| 143 | 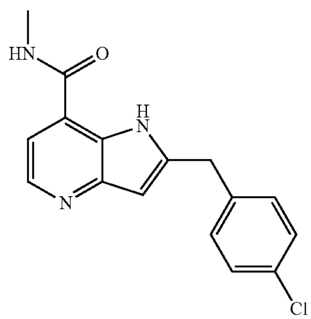 [SMILES: CNC(=O)c1ccnc2cc(Cc3ccc(Cl)cc3)[nH]c12] | 2-[4-chloro-benzyl]-N-methyl-1H-pyrrolo[3,2-b]pyridine-7-carboxamide |
| 144 | 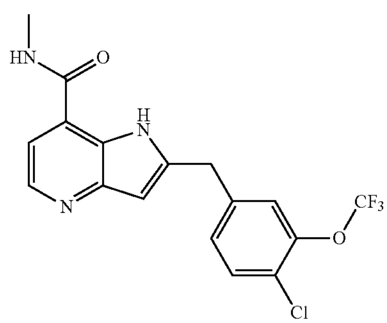 [SMILES: CNC(=O)c1ccnc2cc(Cc3ccc(Cl)c(OC(F)(F)F)c3)[nH]c12] | 2-[4-chloro-3-(trifluoro-methoxy)benzyl]-N-methyl-1H-pyrrolo-[3,2-b]pyridine- |

In additional embodiments, the compound of Formula (I), (Ia), or (II) is selected from a compound provided in Table 2, or alkyl ester derivative thereof.

TABLE 2

2-(4-fluoro-3-methylphenoxy)-1H-pyrrolo[3,2-b]pyridine-7-carboxylic acid 2-(cyclopentylcarbonyl)-1H-pyrrolo[3,2-b]pyridine-7-carboxylic acid 2-(cyclopentyloxy)-1H-pyrrolo[3,2-b]pyridine-7-carboxylic acid 2-phenoxy-1H-pyrrolo[3,2-b]pyridine-7-carboxylic acid TABLE 2-continued

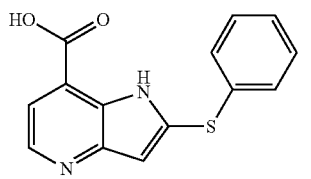 [SMILES: O=C(O)c1ccnc2cc(Oc3ccccc3)[nH]c12]

2-(phenylsulfanyl)-1H-
pyrrolo[3,2-b]pyridine-7-carboxylic acid

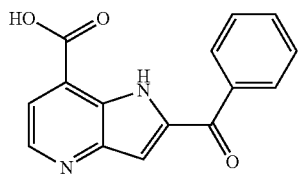 [SMILES: O=C(c1ccccc1)c1cc2nccc(C(=O)O)c2[nH]1]

2-benzoyl-1H-pyrrolo[3,2-b]pyridine-7-
carboxylic acid

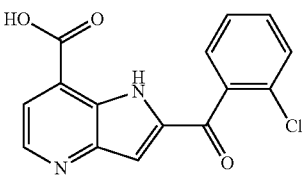 [SMILES: O=C(c1cc2nccc(C(=O)O)c2[nH]1)c1ccccc1Cl]

2-(2-chlorobenzoyl)-1H-
pyrrolo[3,2-b]pyridine-7-carboxylic acid

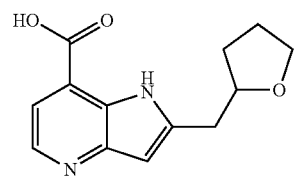 [SMILES: O=C(O)c1ccnc2cc(CC3CCCO3)[nH]c12]

2-(tetrahydrofuran-2-ylmethyl)-1H-
pyrrolo[3,2-b]pyridine-7-carboxylic acid

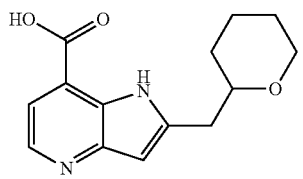 [SMILES: O=C(O)c1ccnc2cc(CC3CCCCO3)[nH]c12]

2-(tetrahydro-2H-pyran-2-ylmethyl)-1H-
pyrrolo[3,2-b]pyridine-7-carboxylic acid

2-(tetrahydrofuran-3-ylmethyl)-1H-
pyrrolo[3,2-b]pyridine-7-carboxylic acid

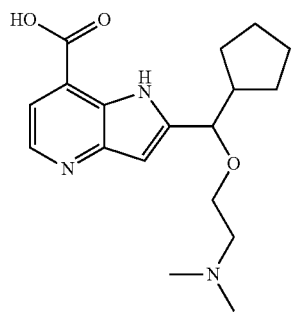 [SMILES: CN(C)CCOC(c1cc2nccc(C(=O)O)c2[nH]1)C1CCCC1]

2-{cylopentyl[2-
(dimethylamino)ethoxy]methyl}-1H-
pyrrolo[3,2-b]pyridine-7-carboxylic acid

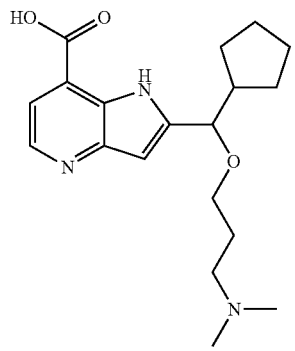 [SMILES: CN(C)CCCOC(c1cc2nccc(C(=O)O)c2[nH]1)C1CCCC1]

2-{cylopentyl[3-(dimethylamino)propoxy]-
methyl}-1H-pyrrolo[3,2-b]pyridine-7-
carboxylic acid

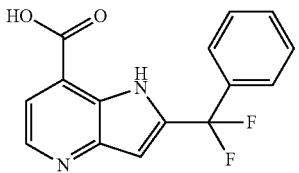 [SMILES: O=C(O)c1ccnc2cc(C(F)(F)c3ccccc3)[nH]c12]

2-[difluoro(phenyl)methyl]-1H-pyrrolo[3,2-
b]pyridine-7-carboxylic acid

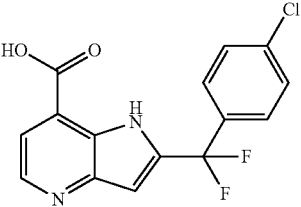

2-[(4-chlorophenyl)(difluoro)methyl]-1H-
pyrrolo[3,2-b]pyridine-7-carboxylic acid

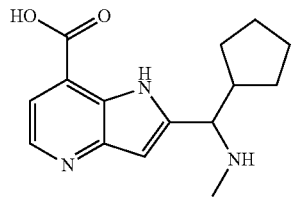 [SMILES: CNC(c1cc2nccc(C(=O)O)c2[nH]1)C1CCCC1]

2-[cyclopentyl(methylamino)methyl]-1H-
pyrrolo[3,2-b]pyridine-7-carboxylic acid

TABLE 2-continued

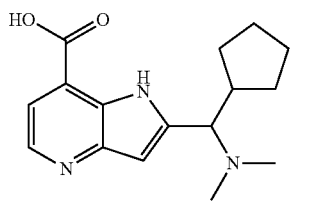 [SMILES: CN(C)C(c1cc2nccc(C(=O)O)c2[nH]1)C1CCCC1]

2-[cyclopentyl(dimethylamino)methyl]-1H-
pyrrolo[3,2-b]pyridine-7-carboxylic acid

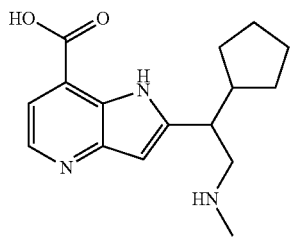 [SMILES: CNCC(c1cc2nccc(C(=O)O)c2[nH]1)C1CCCC1]

2-[1-cyclopentyl-2-(methylamino)ethyl]-1H-
pyrrolo[3,2-b]pyridine-7-carboxylic acid

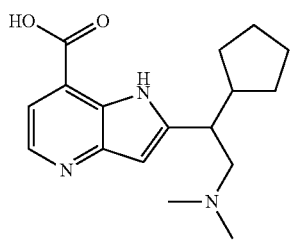 [SMILES: CN(C)CC(c1cc2nccc(C(=O)O)c2[nH]1)C1CCCC1]

2-[1-cyclopentyl-2-(dimethylamino)ethyl]-
1H-pyrrolo[3,2-b]pyridine-7-carboxylic acid

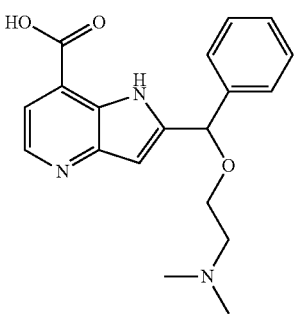 [SMILES: CN(C)CCOC(c1ccccc1)c1cc2nccc(C(=O)O)c2[nH]1]

2-{[2-(dimethylamino)ethoxy](phenyl)methyl}-
1H-pyrrolo[3,2-b]pyridine-7-carboxylic acid

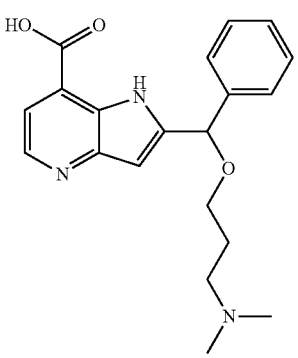 [SMILES: CN(C)CCCOC(c1ccccc1)c1cc2nccc(C(=O)O)c2[nH]1]

2-{[3-(dimethylamino)propoxy]-
(phenyl)methyl}-1H-pyrrolo[3,2-b]pyridine-
7-carboxylic acid TABLE 2-continued

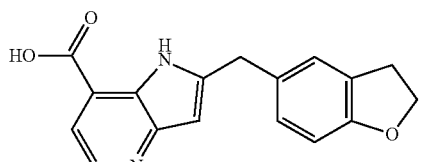

2-(2,3-dihydro-1-benzofuran-5-ylmethyl)-
1H-pyrrolo[3,2-b]pyridine-7-carboxylic acid

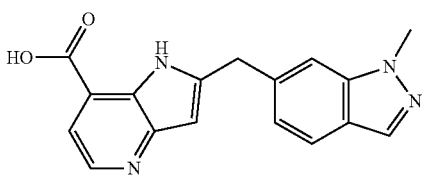 [SMILES: Cn1ncc2ccc(Oc3cc4nccc(C(=O)O)c4[nH]3)cc21]

2-[(1-methylindazol-6-yl)methyl]-1H-
pyrrolo[3,2-b]pyridine-7-carboxylic acid

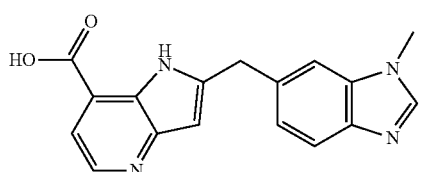

2-[(3-methylbenzimidazol-5-yl) methyl]-1H-
pyrrolo[3,2-b]pyridine-7-carboxylic acid

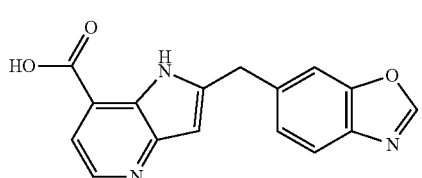

2-(1,3-benzoxazol-6-ylmethyl)-1H-
pyrrolo[3,2-b]pyridine-7-carboxylic acid

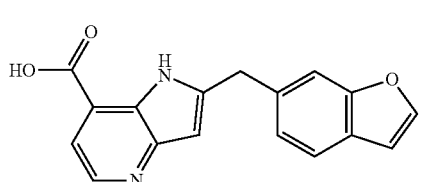

2-(1-benzofuran-6-ylmethyl)-1H-
pyrrolo[3,2-b]pyridine-7-carboxylic acid

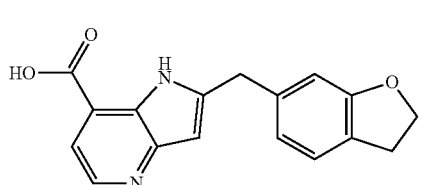

2-(2,3-dihydro-1-benzofuran-6-ylmethyl)-
1H-pyrrolo[3,2-b]pyridine-7-carboxylic acid

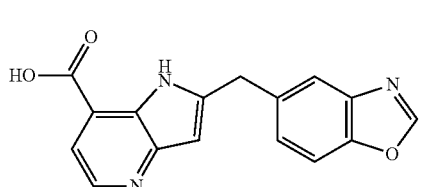

2-(1,3-benzoxazol-5-ylmethyl)-1H-
pyrrolo[3,2-b]pyridine-7-carboxylic acid

TABLE 2-continued

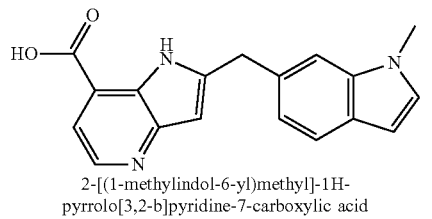

2-[(1-methylindol-6-yl)methyl]-1H-
pyrrolo[3,2-b]pyridine-7-carboxylic acid

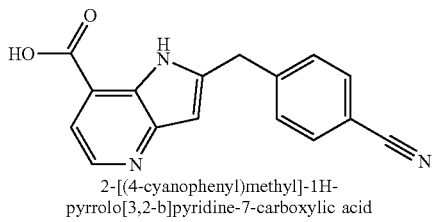

2-[(4-cyanophenyl)methyl]-1H-
pyrrolo[3,2-b]pyridine-7-carboxylic acid

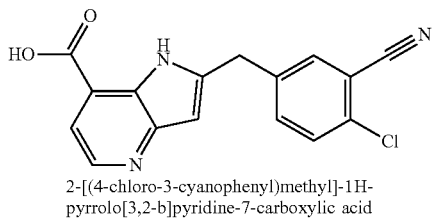

2-[(4-chloro-3-cyanophenyl)methyl]-1H-
pyrrolo[3,2-b]pyridine-7-carboxylic acid

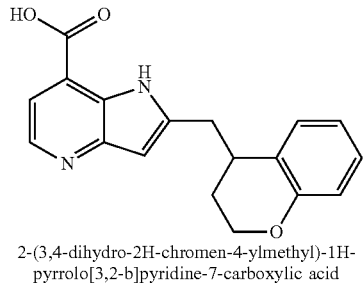

2-(3,4-dihydro-2H-chromen-4-ylmethyl)-1H-
pyrrolo[3,2-b]pyridine-7-carboxylic acid

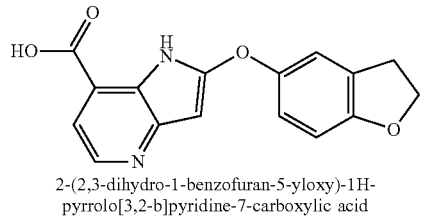

2-(2,3-dihydro-1-benzofuran-5-yloxy)-1H-
pyrrolo[3,2-b]pyridine-7-carboxylic acid

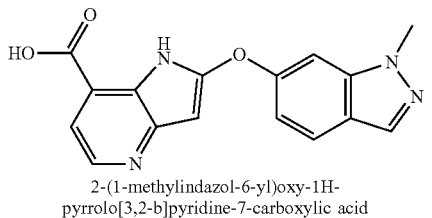

2-(1-methylindazol-6-yl)oxy-1H-
pyrrolo[3,2-b]pyridine-7-carboxylic acid

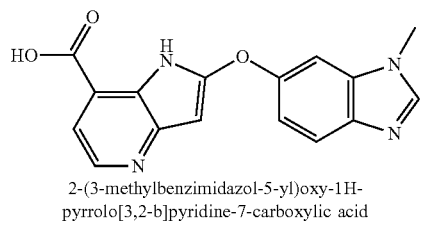

2-(3-methylbenzimidazol-5-yl)oxy-1H-
pyrrolo[3,2-b]pyridine-7-carboxylic acid

TABLE 2-continued

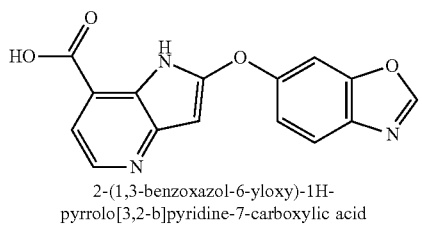

2-(1,3-benzoxazol-6-yloxy)-1H-
pyrrolo[3,2-b]pyridine-7-carboxylic acid

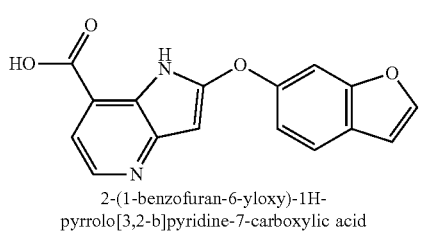

2-(1-benzofuran-6-yloxy)-1H-
pyrrolo[3,2-b]pyridine-7-carboxylic acid

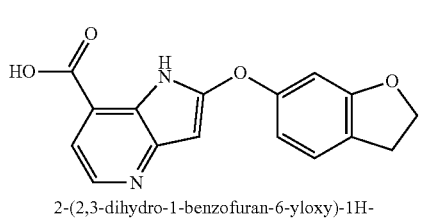

2-(2,3-dihydro-1-benzofuran-6-yloxy)-1H-
pyrrolo[3,2-b]pyridine-7-carboxylic acid

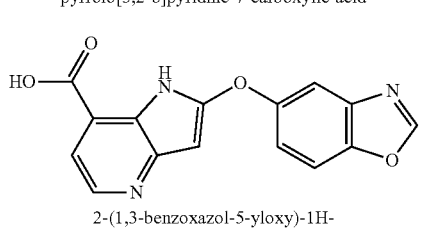

2-(1,3-benzoxazol-5-yloxy)-1H-
pyrrolo[3,2-b]pyridine-7-carboxylic acid

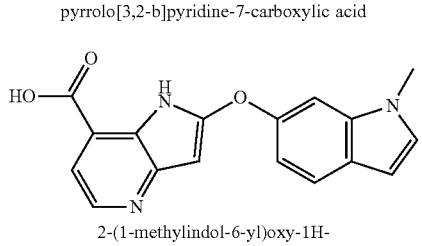

2-(1-methylindol-6-yl)oxy-1H-
pyrrolo[3,2-b]pyridine-7-carboxylic acid

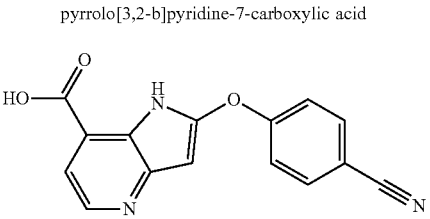

2-(4-cyanophenoxy)-1H-
pyrrolo[3,2-b]pyridine-7-carboxylic acid

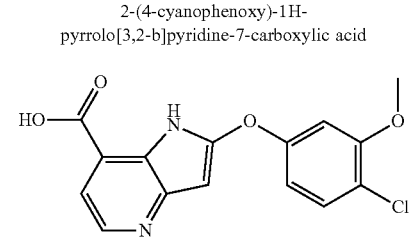

2-(4-chloro-3-methoxyphenoxy)-1H-
pyrrolo[3,2-b]pyridine-7-carboxylic acid

TABLE 2-continued

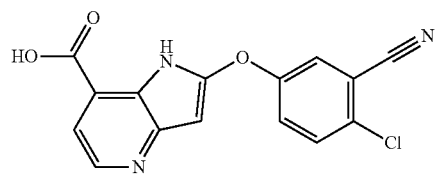 [SMILES: N#Cc1cc(Oc2cc3nccc(C(=O)O)c3[nH]2)ccc1Cl]

2-(4-chloro-3-cyanophenoxy)-1H-
pyrrolo[3,2-b]pyridine-7-carboxylic acid

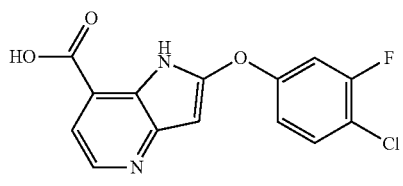 [SMILES: O=C(O)c1ccnc2cc(Oc3ccc(Cl)c(F)c3)[nH]c12]

2-(4-chloro-3-fluorophenoxy)-1H-
pyrrolo[3,2-b]pyridine-7-carboxylic acid

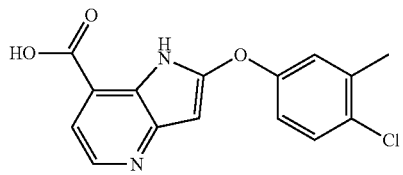 [SMILES: Cc1cc(Oc2cc3nccc(C(=O)O)c3[nH]2)ccc1Cl]

2-(4-chloro-3-methylphenoxy)-1H-
pyrrolo[3,2-b]pyridine-7-carboxylic acid

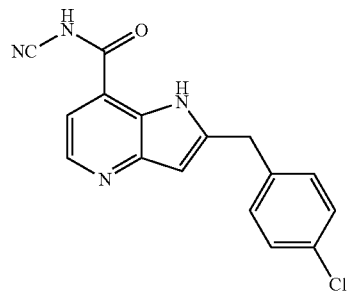

2-(4-chlorobenzyl)-N-cyano-1H-pyrrolo-
[3,2-b]pyridine-7-carboxamide

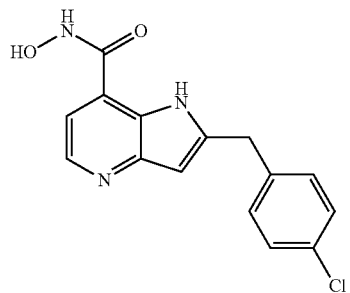 [SMILES: N#CNC(=O)c1ccnc2cc(Cc3ccc(Cl)cc3)[nH]c12]

2-(4-chlorobenzyl)-N-hydroxy-1H-
pyrrolo[3,2-b]pyridine-7-carboxamide

TABLE 2-continued

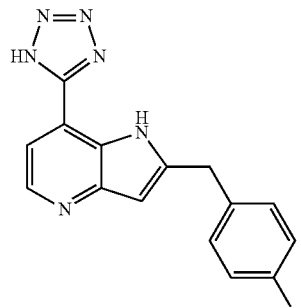

2-(4-chlorobenzyl)-7-(1H-tetrazol-5-yl)-1H-
pyrrolo[3,2-b]pyridine

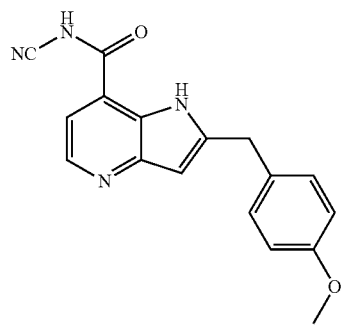

N-cyano-2-(4-methoxybenzyl)-1H-
pyrrolo[3,2-b]pyridine-7-carboxamide

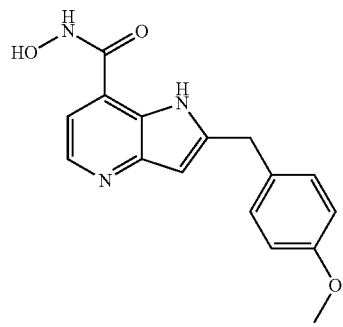 [SMILES: COc1ccc(Cc2cc3nccc(C(=O)NC#N)c3[nH]2)cc1]

N-hydroxy-2-(4-methoxybenzyl)-1H-
pyrrolo[3,2-b]pyridine-7-carboxamide

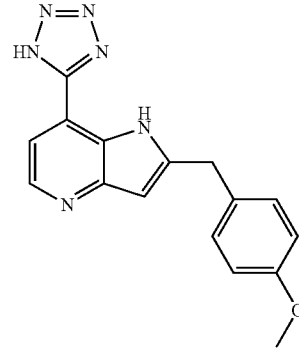

2-(4-methoxybenzyl)-7-(1H-tetrazol-5-yl)-
1H-pyrrolo[3,2-b]pyridine

TABLE 2-continued

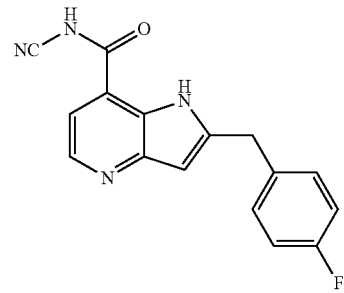 [SMILES: N#CNC(=O)c1ccnc2cc(Cc3ccc(F)cc3)[nH]c12]

N-cyano-2-(4-fluorobenzyl)-1H-pyrrolo-
[3,2-b]pyridine-7-carboxamide

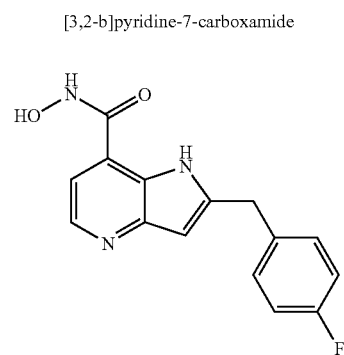

2-(4-fluorobenzyl)-N-hydroxy-1H-
pyrrolo[3,2-b]pyridine-7-carboxamide

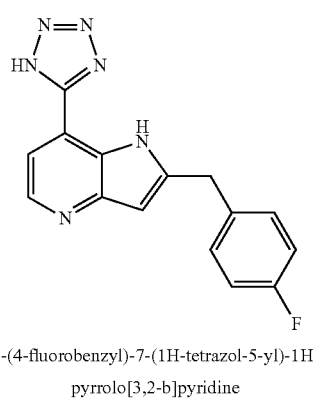

2-(4-fluorobenzyl)-7-(1H-tetrazol-5-yl)-1H-
pyrrolo[3,2-b]pyridine

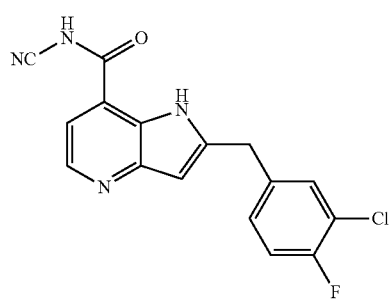

2-(3-chloro-4-fluorobenzyl)-N-cyano-1H-
pyrrolo[3,2-b]pyridine-7-carboxamide

TABLE 2-continued

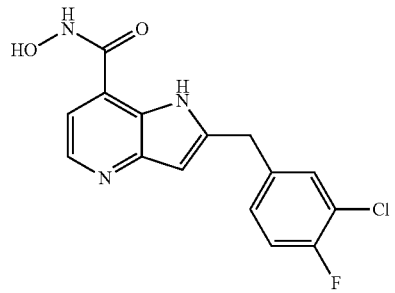 [SMILES: N#CNC(=O)c1ccnc2cc(Cc3ccc(F)c(Cl)c3)[nH]c12]

2-(3-chloro-4-fluorobenzyl)-N-hydroxy-1H-
pyrrolo[3,2-b]pyridine-7-carboxamide

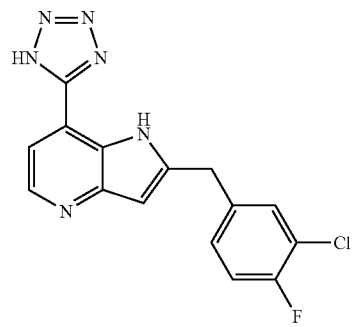 [SMILES: Fc1ccc(Cc2cc3nccc(-c4nnn[nH]4)c3[nH]2)cc1Cl]

2-(3-chloro-4-fluorobenzyl)-7-(1H-tetrazol-
5-yl)-1H-pyrrolo[3,2-b]pyridine

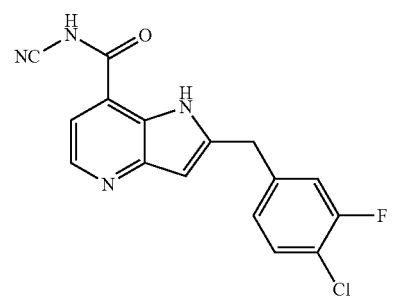

2-(4-chloro-3-fluorobenzyl)-N-cyano-1H-
pyrrolo[3,2-b]pyridine-7-carboxamide

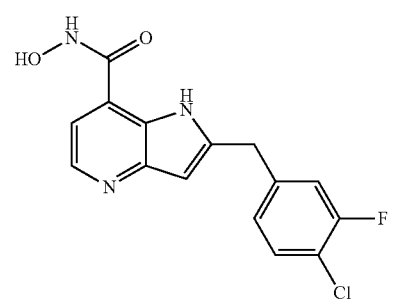 [SMILES: N#CNC(=O)c1ccnc2cc(Cc3ccc(Cl)c(F)c3)[nH]c12]

2-(4-chloro-3-fluorobenzyl)-N-hydroxy-1H-
pyrrolo[3,2-b]pyridine-7-carboxamide

TABLE 2-continued 2-(4-chloro-3-fluorobenzyl)-7-(1H-tetrazol-5-yl)-1H-pyrrolo[3,2-b]pyridine ethyl 2-[(4-chloro-3-fluorophenyl)methyl]-1H-pyrrolo[3,2-b]pyridine-7-carboxylate 2,2-dimethylpropanoyloxymethyl 2-[(4-chloro-3-fluorophenyl)methyl]-1H-pyrrolo[3,2-b]pyridine-7-carboxylate 2-[(3,4,5-trichlorophenyl)methyl]-1H-pyrrolo[3,2-b]pyridine-7-carboxylic acid methyl 2-[(3,4,5-trichlorophenyl)methyl]-1H-pyrrolo[3,2-b]pyridine-7-carboxylate methyl 2-[(3-chlorophenyl)methyl]-1H-pyrrolo[3,2-b]pyridine-7-carboxylate 2-[(3-chlorophenyl)methyl]-1H-pyrrolo-[3,2-b]pyridine-7-carboxylic acid methyl 2-[(4-chloro-3-ethylphenyl)methyl]-1H-pyrrolo[3,2-b]pyridine-7-carboxylate cyclobutylmethyl 2-[(4-chlorophenyl)-methyl]-1H-pyrrolo[3,2-b]pyridine-7-carboxylate

TABLE 2-continued

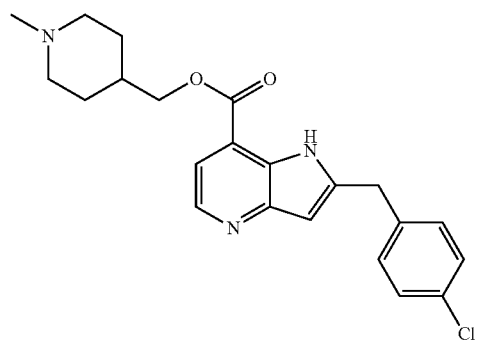 [SMILES: CN1CCC(COC(=O)c2ccnc3cc(Cc4ccc(Cl)cc4)[nH]c23)CC1]

(1-methylpiperidin-4-yl)methyl-2-
[(4-chlorophenyl)methyl]-1H-pyrrolo-
[3,2-b]pyridine-7-carboxylate

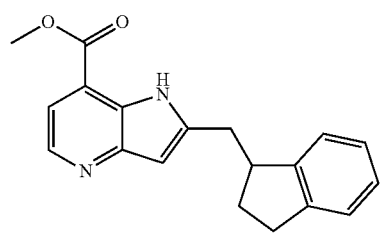 [SMILES: COC(=O)c1ccnc2cc(CC3CCc4ccccc43)[nH]c12]

methyl 2-(2,3-dihydro-1H-inden-1-yl-
methyl)-1H-pyrrolo[3,2-b]pyridine-7-carboxylate

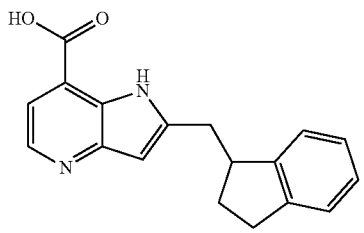 [SMILES: O=C(O)c1ccnc2cc(CC3CCc4ccccc43)[nH]c12]

2-(2,3-dihydro-1H-inden-1-ylmethyl)-1H-
pyrrolo[3,2-b]pyridine-7-carboxylic acid

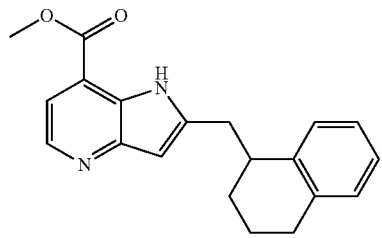 [SMILES: COC(=O)c1ccnc2cc(CC3CCCc4ccccc43)[nH]c12]

methyl 2-(1,2,3,4-tetrahydronaphthalen-1-yl-
methyl)-1H-pyrrolo[3,2-b]pyridine-7-carboxylate

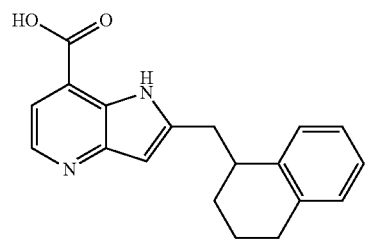 [SMILES: O=C(O)c1ccnc2cc(CC3CCCc4ccccc43)[nH]c12]

2-(1,2,3,4-tetrahydronaphthalen-1-ylmethyl)-
1H-pyrrolo[3,2-b]pyridine-7-carboxylic acid

TABLE 2-continued

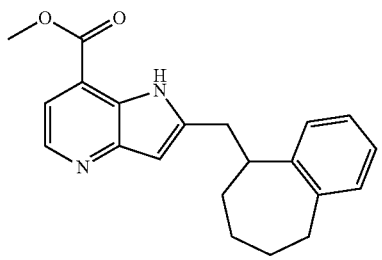 [SMILES: COC(=O)c1ccnc2cc(CC3CCCCc4ccccc43)[nH]c12]

methyl 2-(6,7,8,9-tetrahydro-5H-
benzo[7]annulen-5-ylmethyl)-1H-
pyrrolo[3,2-b]pyridine-7-carboxylate

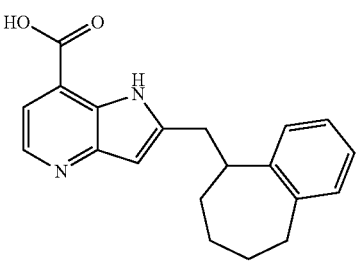 [SMILES: O=C(O)c1ccnc2cc(CC3CCCCc4ccccc43)[nH]c12]

2-(6,7,8,9-tetrahydro-5H-benzo[7]annulen-
5-yl-methyl)-1H-pyrrolo[3,2-b]pyridine-
7-carboxylic acid

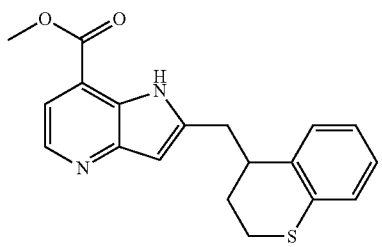 [SMILES: COC(=O)c1ccnc2cc(CC3CCSc4ccccc43)[nH]c12]

methyl 2-(3,4-dihydro-2H-thiochromen-4-yl-
methyl)-1H-pyrrolo[3,2-b]pyridine-
7-carboxylate

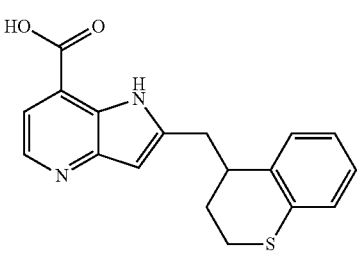 [SMILES: O=C(O)c1ccnc2cc(CC3CCSc4ccccc43)[nH]c12]

2-(3,4-dihydro-2H-thiochromen-4-ylmethyl)-
1H-pyrrolo[3,2-b]pyridine-7-carboxylic acid Preparation of the Substituted Pyrrolopyridine
Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., NY; Sandler et al., "Organic Functional Group Preparations," 2nd Ed., Academic Press, N Y, 1983; House, "Modern Synthetic Reactions", 2nd Ed., Benjamin, Inc. Menlo Park, Calif. 1972; Gilchrist, "Heterocyclic Chemistry", 2nd Ed., John Wiley & Sons, N Y, 1992; March, "Advanced Organic Chemistry: Reactions, Mechanisms & Structure", 4th Ed., Wiley-Interscience, N Y, 1992. Additional suitable reference books and treatise that detail the synthesis of reactants useful in the preparation of compounds described herein, or provide references to articles that describe the preparation, include for example, Fuhrhop & Penzlin "Organic Synthesis: Concepts, Methods, Starting Materials", 2nd, Revised, Enlarged Ed. (1994) John Wiley & Sons ISBN: 3-527-29074-5; Hoffman, "Organic Chemistry, Intermediate Text" (1996) Oxford Univ. Press, ISBN 0-19-509618-5; Larock, "Comprehensive Organic Transformations: A Guide to Functional Group Preparations" 2nd Ed. (1999) Wiley-VCH, ISBN: 0-471-19031-4; March, "Advanced Organic Chemistry: Reactions, Mechanisms, and Structure" 4th Ed. (1992) John Wiley & Sons, ISBN: 0-471-60180-2; Otera, (editor) "Modern Carbonyl Chemistry" (2000) Wiley-VCH, ISBN: 3-527-29871-1; Patai, "Patai's 1992 Guide to the Chemistry of Functional Groups" (1992) Interscience ISBN: 0-471-93022-9; Solomons, "Organic Chemistry" 7th Ed. (2000) John Wiley & Sons, ISBN: 0-471-19095-0; Stowell, "Intermediate Organic Chemistry" 2nd Ed. (1993) Wiley-Interscience, ISBN: 0-471-57456-2; "Industrial Organic Chemicals: Starting Materials & Intermediates: Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted pyrrolopyridine derivative compounds described herein is Stahl & Wermuth "Handbook of Pharmaceutical Salts", Verlag Helvetica Chimica Acta, Zurich, 2002.

The substituted pyrrolopyridine derivative compounds are prepared by the general synthetic routes described in Schemes 1 and 2.

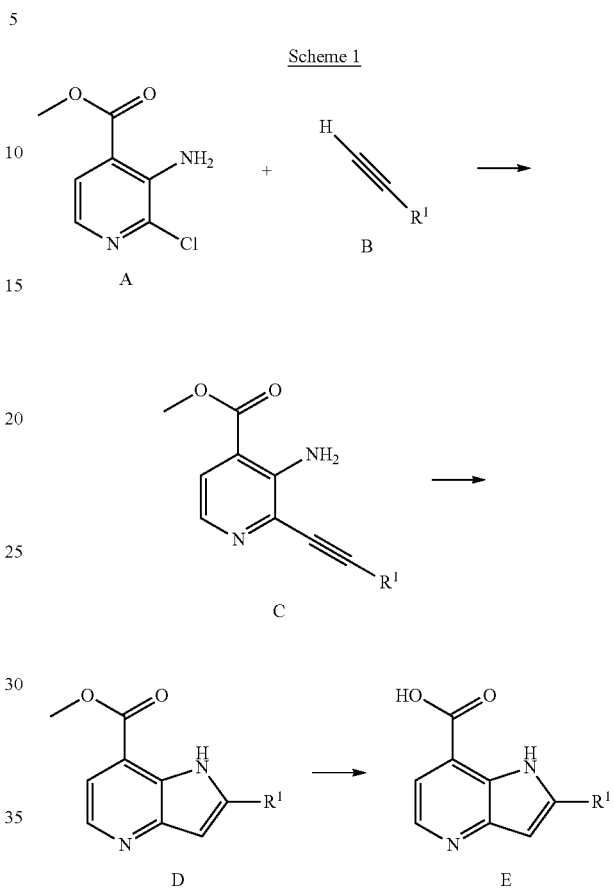

Referring to Scheme 1, compound A and terminal alkyne compound B are combined and treated under a variety of palladium-mediated Sonogashira cross-coupling conditions to form compound C. For example, the mixture of compound A and an alkyne B can be subjected to conditions similar to procedures described in literature (Tetrahedron Lett. 4467-4470; Org. Lett. 2006, 3307-10 (1975)) using various catalyst, co-catalyst, ligand, base, and solvent, at temperatures ranging from 40° C. to 100° C. The azaindole compound D can be prepared by cycloisomerization of compound C using a base, such as KOtBu at 0° C., or catalyzed by CuI at temperature ranging from 100° C. to 140° C. Acid compound E can be prepared by hydrolysis of ester compound D using base, such as NaOH, or by other conditions known in the art for ester hydrolysis.

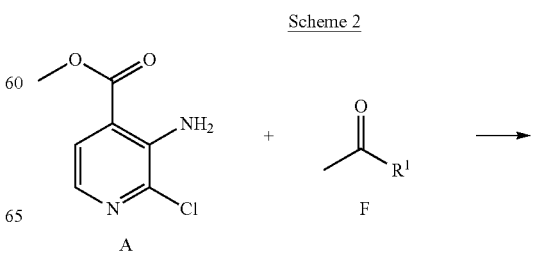

-continued

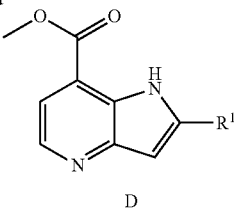

D

Referring to Scheme 2, compound A and a ketone compound F are mixed and treated to palladium-mediated direct annulation conditions to form compound D. For example, the mixture of compound A and a ketone B can be subjected to conditions similar to procedures described in literature (Angew. Chem. Int. Ed. 2004, 4526-4528) using a Pd catalyst, ligand, acid, base, and solvent, at temperatures range up to 140° C.

In each of the above reaction procedures or schemes, the various substituents may be selected from among the various substituents otherwise taught herein.

Pharmaceutical Compositions

In certain embodiments, a substituted pyrrolopyridine derivative compound as described herein is administered as a pure chemical. In other embodiments, the substituted pyrrolopyridine derivative compound as described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: Science & Practice of Pharmacy (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising at least one substituted pyrrolopyridine derivative compound as described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (Ia), or a pharmaceutically acceptable salt thereof.

One embodiment provides a pharmaceutical composition comprising a pharmaceutically acceptable carrier and a compound of Formula (II), or a pharmaceutically acceptable salt thereof.

In certain embodiments, the substituted pyrrolopyridine derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: Science & Practice of Pharmacy (Gennaro, 21$^{st}$ Ed. Mack Pub. Co., Easton, Pa. (2005)).

The dose of the composition comprising at least one substituted pyrrolopyridine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas monomethylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri- and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and α-ketoglutarate., wherein oxidative decarboxylation of α-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. Proc. Natl. Acad. Sci. USA, Aug. 16, 2011, 108(33),13379-86; doi: 10.1073/pnas.1110104108) and lead to the conclusion that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as $BR^cA1$, CAV1 and 14-3-3a, and knockdown of JARID1B was found to increase the levels of tri-methylated H3K4 at these genes.

In an additional embodiment is a method for inhibiting a histone-demethylase enzyme comprising contacting a histone demethylase enzyme with a compound of Formula (I), or a pharmaceutically acceptable salt thereof.

In an additional embodiment is a method for inhibiting a histone-demethylase enzyme comprising contacting a histone demethylase enzyme with a compound of Formula (Ia), or a pharmaceutically acceptable salt thereof.

In an additional embodiment is a method for inhibiting a histone-demethylase enzyme comprising contacting a histone demethylase enzyme with a compound of Formula (II), or a pharmaceutically acceptable salt thereof.

In an additional embodiment is the method for inhibiting a histone-demethylase enzyme, wherein the histone-demethylase enzyme comprises a JmjC domain. In an additional embodiment is the method for inhibiting a histone-demethylase enzyme, wherein the histone-demethylase enzyme is selected from JARID1A, JARID1B, JMJD2C, or JMJD2A.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a JmjC domain (e.g., a histone demethylase such as a JHDM protein(s)).

In an additional embodiment is a method for treating cancer in subject comprising administering a composition comprising a compound of Formula (I), (Ia), or (II), or a pharmaceutically acceptable salt thereof.

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound of Formula (I), (Ia), or (II), or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound of Formula (I), (Ia), or (II), or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1: 3-chloro-1H-pyrrolo[3,2-b]pyridine-7-carboxylic Acid

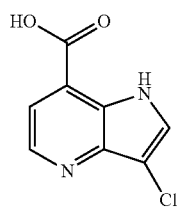

To a vial charged with 1H-pyrrolo[3,2-b]pyridine-7-carboxylic acid (130 mg, 0.8 mmol) in acetonitrile (2 mL) was added NCS (133.5 mg, 1.0 mmol). The reaction was allowed to stir at 70° C. for 2 hr. The reaction was quenched with water and pH adjusted to ~3 with HCl (1 N). The precipitate was filtered and washed successively with water, ethanol, and dried in vacuo to afford the title compound (79 mg, 40%) as a yellow solid. $^1$H NMR (400 MHz, DMSO-d$_6$) δ ppm 7.66 (d, J=4.80 Hz, 1H), 7.82 (d, J=3.03 Hz, 1H), 8.56 (d, J=4.80 Hz, 1H), 11.54-11.87 (m, 1H), 13.90 (br. s., 1H). [M+H] calc'd for $C_8H_5N_2O_2Cl$, 197; found 197.

Example 2: 2-phenyl-1H-pyrrolo[3,2-b]pyridine-7-carboxylic Acid

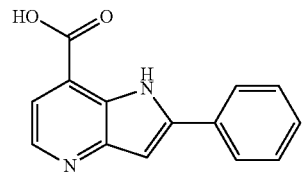 [SMILES: O=C(O)c1ccnc2cc(-c3ccccc3)[nH]c12]

Methyl 3-amino-2-chloroisonicotinate (187 mg, 1.0 mmol), Pd(PPh$_3$)$_2$C$_2$ (35 mg, 0.05 mmol), CuI (38 mg, 0.20 mmol), TEA (278 μL, 2.0 mmol) and phenylacetylene (130 mg, 1.2 mmol) were suspended in DMF (2 mL). N$_2$ was bubbled into the reaction for 2 min and it was allowed to stir at 100° C. for 16 hr. The reaction was concentrated in vacuo and purified by column chromatography (0-50% gradient of EtOAc/Hex) to afford methyl 3-amino-2-(phenylethynyl)pyridine-4-carboxylate (195 mg, 77%) as a brown foam. [M+H] calc'd for $C_{14}H_{10}N_2O_2$, 239; found 239.

Methyl 3-amino-2-(phenylethynyl)pyridine-4-carboxylate (50 mg, 0.2 mmol) in NMP (1 mL) was added KO-t-Bu (67.5 mg, 0.6 mmol) and allowed to stir for 2 hr. Water was added and the pH was adjusted to ~3 with HCl (1N). The precipitate was filtered and the filter cake was successively washed with water followed by ethanol to afford the title compound as a white solid (34 mg, 74%). $^1$H NMR (400 MHz, DMSO-d$_6$): δ ppm 7.18 (s, 1H), 7.38-7.63 (m, 5H), 8.02 (d, J=7.33 Hz, 2H), 8.36-8.62 (m, 1H). [M+H] calc'd for $C_{14}H_{10}N_2O_2$, 239; found 239.

Example 3: 2-(2-methylphenyl)-1H-pyrrolo[3,2-b]pyridine-7-carboxylic Acid

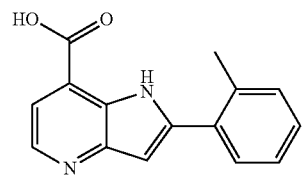

The title compound was prepared in 64% yield using 2-ethynyltoluene according to the procedure for the preparation of Example 2. $^1$H NMR (400 MHz, DMSO-d$_6$): δ ppm 2.43 (s, 3H), 6.80 (s, 1H), 7.30-7.42 (m, 3H), 7.45-7.66 (m, 2H), 8.49 (d, J=4.80 Hz, 1H), 11.21 (br. s., 1H), 13.66 (br. s., 1H). [M+H] calc'd for $C_{15}H_{12}N_2O_2$, 253; found 253.

Example 4: methyl 2-(2-hydroxypropan-2-yl)-1H-pyrrolo[3,2-b]pyridine-7-carboxylate

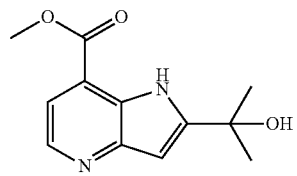 [SMILES: COC(=O)c1ccnc2cc(C(C)(C)O)[nH]c12]

Methyl 3-amino-2-chloroisonicotinate (186 mg, 1 mmol), PdCl$_2$(CH$_3$CN)$_2$ (5.2 mg, 0.02 mmol), X-Phos (19 mg, 0.04 mmol), K$_2$CO$_3$ (278 mg, 2.0 mmol), and 2-methyl-3-butyn-2-ol (130 mg, 1.2 mmol) in CH$_3$CN (2 mL) was purged with N$_2$ for 2 min. The reaction was allowed to stir at 80° C. for 16 hr. The reaction was concentrated in vacuo and purified by column chromatography (0-50% gradient of EtOAc/Hex) to afford methyl 3-amino-2-(3-hydroxy-3-methylbut-1-yn-1-yl)pyridine-4-carboxylate (191 mg, 81%). [M+H] calc'd for C$_{12}$H$_{14}$N$_2$O$_3$, 235; found 235.

Methyl 3-amino-2-(3-hydroxy-3-methylbut-1-yn-1-yl)pyridine-4-carboxylate (191 mg, 0.82 mmol) and CuI (47.5 mg, 0.25 mmol) in DMF (2 mL) was purged with N$_2$ for 2 min, and the reaction was allowed to stir at 110° C. for 2 hr. The reaction mixture was concentrated and purified by column chromatography (0-50% gradient of EtOAc/Hex) to afford the title compound as an amorphous solid (172 mg, 74%). $^1$H NMR (400 MHz, DMSO-d$_6$): δ ppm 2.43 (s, 3H), 6.80 (s, 1H), 7.30-7.42 (m, 3H), 7.45-7.66 (m, 2H), 8.49 (d, J=4.80 Hz, 1H), 11.21 (br. s., 1H), 13.66 (br. s., 1H). [M+H] calc'd for C$_{12}$H$_{14}$N$_2$O$_3$, 235; found 235.

Example 5: 2-(2-hydroxypropan-2-yl)-1H-pyrrolo[3,2-b]pyridine-7-carboxylic Acid

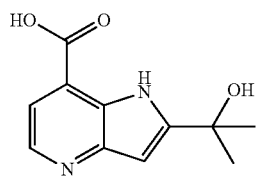

To methyl 2-(2-hydroxypropan-2-yl)-1H-pyrrolo[3,2-b]pyridine-7-carboxylate (100 mg, 0.45 mmol) in MeOH (1 mL) was added NaOH (75 μL, 1N), and the reaction stirred at 60° C. for 30 min. HCl (75 μL, 1N) was added at ambient temperature to give a suspension. The solid was filtered and washed successively with water followed by ethanol and dried in vacuo to afford the title compound (68 mg, 69%) as an off-white solid. $^1$H NMR (400 MHz, DMSO-d$_6$): δ ppm 1.50 (s, 6H), 5.56 (br. s., 1H), 6.40 (s, 1H), 7.41 (d, J=5.05 Hz, 1H), 8.33 (d, J=4.80 Hz, 1H), 10.30 (br. s., 1H). [M+H] calc'd for C$_{11}$H$_{12}$N$_2$O$_3$, 221; found 221.

Example 6: methyl 2-benzyl-1H-pyrrolo[3,2-b]pyridine-7-carboxylate

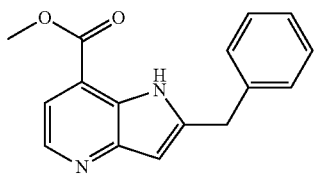 [SMILES: COC(=O)c1ccnc2cc(Cc3ccccc3)[nH]c12]

The title compound was prepared in 60% yield using 3-phenyl-propyne according to the procedure for the preparation of Example 4. $^1$H NMR (400 MHz, CDCl$_3$): δ ppm 3.98 (s, 3H), 4.22 (s, 2H), 6.59-6.63 (m, 1H), 7.27-7.42 (m, 5H), 7.55 (d, J=4.80 Hz, 1H), 8.50 (d, J=5.05 Hz, 1H), 9.26 (br. s., 1H). [M+H] calc'd for C$_{16}$H$_{14}$N$_2$O$_2$, 267; found 267.

Example 7: 2-benzyl-1H-pyrrolo[3,2-b]pyridine-7-carboxylic Acid, Sodium Salt

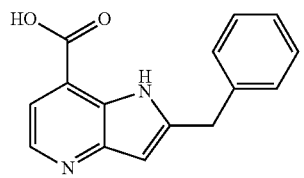 [SMILES: O=C(O)c1ccnc2cc(Cc3ccccc3)[nH]c12]

The title compound was prepared in 94% yield with methyl 2-benzyl-1H-pyrrolo[3,2-b]-pyridine-7-carboxylate according to the procedure for the preparation of Example 5. The title compound (67 mg, 0.27 mmol) was taken up in CH$_3$CN/water (1:1) and NaOH (293 μL, 1N) and lyophilized for 16 hr to afford the sodium salt. $^1$H NMR (400 MHz, DMSO-d$_6$): δ ppm 4.11 (s, 2H), 6.12 (d, J=2.02 Hz, 1H), 7.17 (d, J=4.80 Hz, 2H), 7.21-7.31 (m, 4H), 8.08 (d, J=4.80 Hz, 1H), 10.66 (br. s., 1H). [M+H] calc'd for C$_{15}$H$_{12}$N$_2$O$_2$, 253; found 253.

Example 8: 2-propyl-1H-pyrrolo[3,2-b]pyridine-7-carboxylic Acid

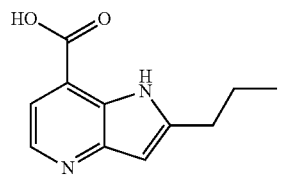

The title compound was prepared in 28% yield using 1-pentyne according to the procedures for the preparation of Examples 4 and 5. $^1$H NMR (400 MHz, DMSO-d$_6$): δ ppm 0.84-0.97 (m, 3H), 1.67 (m, 2H), 6.52 (s, 1H), 7.57-7.70 (m, 1H), 8.42-8.59 (m, 1H), 11.79 (br. s., 1H). [M+H] calc'd for C$_{11}$H$_{12}$N$_2$O$_2$, 205; found 205.

Example 9: methyl-2-(hydroxymethyl)-1H-pyrrolo[3,2-b]pyridine-7-carboxylate

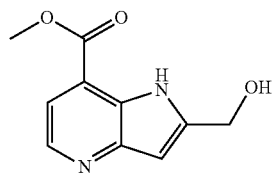

Methyl 3-amino-2-chloroisonicotinate (1.04 g, 5.64 mmol), propargyl alcohol (393 μL, 6.76 mmol), Pd(PPh$_3$)$_2$Cl$_2$ (198 mg, 0.28 mmol), CuI (28 mg, 0.14 mmol), and TEA (2.84 g, 28.18 mmol) were combined in acetonitrile (20 mL). The reaction was purged with nitrogen for 2 min and then was stirred at 40° C. for 16 hr. The reaction was concentrated in vacuo and the residue suspended in dichloromethane and filtered. The filtrate was concentrated in vacuo and the residue purified by silica gel chromatography (PE/EA=3/1~1/1) to afford methyl 3-amino-2-(3-hydroxy-prop-1-yn-1-yl)pyridine-4-carboxylate (200 mg, 18%). ¹H NMR (300 MHz, DMSO-d₆): δ 3.86 (3H, s), 4.39 (2H, d, J=8.0 Hz), 5.42 (1H, t, J=8.0 Hz), 6.24 (2H, s), 7.55 (1H, d, J=6.4 Hz), 7.81 (1H, d, J=5.6 Hz). [M+H] Calc'd for C₁₀H₁₀N₂O₃, 207; Found, 207.

Methyl 3-amino-2-(3-hydroxyprop-1-yn-1-yl)pyridine-4-carboxylate (476 mg, 2.31 mmol), CaCO₃ (427 mg, 4.27 mmol), CuI (203 mg, 1.07 mmol), and DMF (10 mL) was purged with nitrogen and stirred for 1 hr at 120° C. The reaction was concentrated in vacuo and the residue suspended in dichloromethane and filtered. The filtrate was concentrated in vacuo and the residue purified by silica gel chromatograph (PE/EA=3/1~1/1) to afford title the compound (40 mg, 20%). ¹H NMR (400 MHz, DMSO-d₆) δ 3.98 (3H, s), 4.72 (2H, d, J=6.8 Hz), 5.37 (1H, t, J=8.4 Hz), 6.57 (1H, t, J=1.6 Hz), 7.52 (1H, d, J=6.8 Hz), 8.42 (1H, d, J=6.4 Hz), 11.11 (1H, s). LCMS (mobile phase: 10%-95% Acetonitrile-Water-0.02% NH₄Ac): purity is >95%, Rt=1.970 min. [M+H] Calc'd for C₁₀H₁₀N₂O₃, 207; Found, 207.

Example 10: 2-(hydroxymethyl)-1H-pyrrolo[3,2-b]pyridine-7-carboxylic Acid

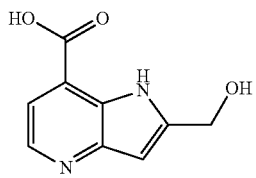 [SMILES: O=C(O)c1ccnc2cc(CO)[nH]c12]

The title compound was prepared in 37% yield using methyl-2-(hydroxymethyl)-1H-pyrrolo[3,2-b]pyridine-7-carboxylate according to the procedure for the preparation of Example 5. ¹H NMR (400 MHz, DMSO-d₆): δ ppm 4.76 (s, 2H), 6.67 (s, 1H), 7.68 (d, J=5.31 Hz, 1H), 8.53 (d, J=5.31 Hz, 1H), 11.63 (br. s., 1H). [M+H] calc'd for C₉H₈N₂O₃, 193; found 193.

Example 11: methyl 2-cyclopropyl-1H-pyrrolo[3,2-b]pyridine-7-carboxylate

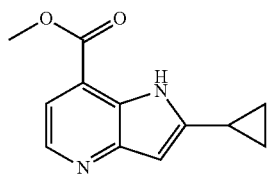 [SMILES: COC(=O)c1ccnc2cc(C3CC3)[nH]c12]

The title compound was prepared in 54% yield using cyclopropylacetylene according to the procedure for the preparation of Example 4. ¹H NMR (400 MHz, CDCl₃): δ ppm 0.79-0.98 (m, 2H), 1.00-1.17 (m, 2H), 1.96-2.21 (m, 1H), 4.02 (s, 3H), 6.38 (s, 1H), 7.51 (d, J=5.05 Hz, 1H), 8.47 (d, J=5.05 Hz, 1H), 9.38 (br. s., 1H). [M+H] calc'd for C₁₂H₁₂N₂O₂, 217; found 217.

Example 12: 2-cyclopropyl-1H-pyrrolo[3,2-b]pyridine-7-carboxylic Acid

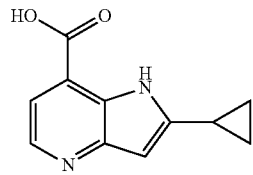 [SMILES: O=C(O)c1ccnc2cc(C3CC3)[nH]c12]

The title compound was prepared in 85% yield using methyl 2-cyclopropyl-1H-pyrrolo-[3,2-b]pyridine-7-carboxylate according to the procedure for the preparation of Example 5. ¹H NMR (400 MHz, DMSO-d₆): δ ppm 0.99 (dd, J=4.80, 2.27 Hz, 1H), 1.21 (dd, J=8.34, 2.53 Hz, 1H), 6.36 (d, J=1.77 Hz, 1H), 7.69 (d, J=5.56 Hz, 1H), 8.50 (d, J=5.56 Hz, 1H), 12.31 (br. s., 1H). [M+H] calc'd for C₁₁H₁₀N₂O₂, 203; found 203.

Example 13: methyl 2-(1-hydroxycyclohexyl)-1H-pyrrolo[3,2-b]pyridine-7-carboxylate

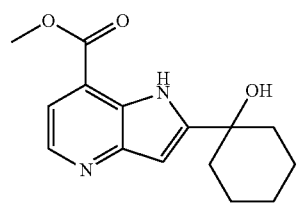 [SMILES: COC(=O)c1ccnc2cc(C3(O)CCCCC3)[nH]c12]

The title compound was prepared in 62% yield using 1-ethynylcyclohexanol according to the procedure for the preparation of example 4. ¹H NMR (400 MHz, CDCl₃): δ ppm 1.61-2.37 (m, 11H), 4.03 (s, 3H), 6.59 (d, J=2.27 Hz, 1H), 7.54-7.78 (m, 1H), 8.51 (d, J=4.80 Hz, 1H), 9.73 (br. s., 1H). [M+H] calc'd for C₁₅H₁₈N₂O₃, 275; found 275.

Example 14: 2-(1-hydroxycyclohexyl)-1H-pyrrolo[3,2-b]pyridine-7-carboxylic Acid

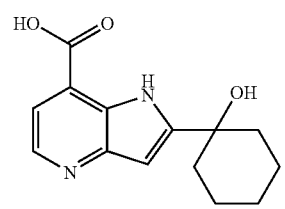

The title compound was prepared in 85% yield using methyl 2-(1-hydroxycyclohexyl)-1H-pyrrolo[3,2-b]pyridine-7-carboxylate according to the procedure for the preparation of Example 5. ¹H NMR (400 MHz, DMSO-d₆): δ ppm 1.46-1.59 (m, 2H), 1.59-1.96 (m, 8H), 5.36 (s, 1H), 6.50 (d, J=2.02 Hz, 1H), 7.49 (d, J=5.05 Hz, 1H), 8.41 (d, J=4.80 Hz, 1H), 10.32 (br. s., 1H), 13.81 (br. s., 1H). [M+H] calc'd for C₁₄H₁₆N₂O₃, 261; found 261.

Example 15: methyl 2-(4-methoxy-2-methylphenyl)-1H-pyrrolo[3,2-b]-pyridine-7-carboxylate

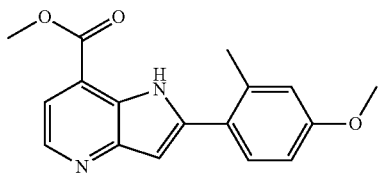

The title compound was prepared in 23% yield using 1-ethynyl-4-methoxy-2-methylbenzene according to the procedure for the preparation of Example 4. $^1$H NMR (400 MHz, CDCl$_3$): δ ppm 2.52 (s, 3H), 3.87 (s, 3H), 4.05 (s, 3H), 6.86-7.00 (m, 3H), 7.48 (d, J=8.08 Hz, 1H), 7.63 (d, J=5.05 Hz, 1H), 8.56 (d, J=5.31 Hz, 1H), 9.61 (br. s., 1H). [M+H] calc'd for C$_{17}$H$_{16}$N$_2$O$_3$, 297; found 297.

Example 16: 2-(4-methoxy-2-methylphenyl)-1H-pyrrolo[3,2-b]pyridine-7-carboxylic Acid

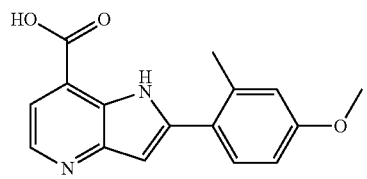 [SMILES: COc1ccc(-c2cc3nccc(C(=O)O)c3[nH]2)c(C)c1]

The title compound was prepared in 95% yield using methyl 2-(4-methoxy-2-methyl-phenyl)-1H-pyrrolo[3,2-b]pyridine-7-carboxylate according to the procedure for the preparation of Example 5. $^1$H NMR (400 MHz, DMSO-d$_6$): δ ppm 2.42 (s, 3H), 3.81 (s, 3H), 6.72 (s, 1H), 6.85-7.02 (m, 2H), 7.50 (dd, J=13.52, 6.69 Hz, 2H), 8.45 (d, J=4.80 Hz, 1H), 11.02 (br. s., 1H), 13.59-13.76 (m, 1H). [M+H] calc'd for C$_{16}$H$_{14}$N$_2$O$_3$, 283; found 283.

Example 17: (±)-methyl 2-(1-hydroxyethyl)-1H-pyrrolo[3,2-b]pyridine-7-carboxylate

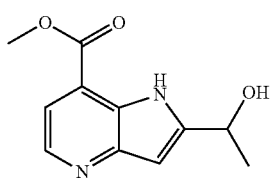 [SMILES: COC(=O)c1ccnc2cc(C(C)O)[nH]c12]

The title compound was prepared in 9% yield using (±)-propyn-3-ol according to the preparation of Example 9. $^1$H NMR (400 MHz, CDCl$_3$): δ ppm 1.68 (3H, d, J=6.4 Hz), 4.02 (3H, s), 5.18 (1H, q, J=6.4 Hz), 6.61 (1H, s), 7.69 (1H, d, J=4.8 Hz), 8.52 (1H, d, J=4.8 Hz), 9.68 (1H, s). LCMS (mobile phase: 5-60% Acetonitrile-Water-0.02% NH$_4$Ac): purity is >95%, Rt=2.852 min. [M+H] calc'd for C$_{11}$H$_{12}$N$_2$O$_3$, 221; found 221.

Example 18: (±)-2-(1-hydroxyethyl)-1H-pyrrolo[3,2-b]pyridine-7-carboxylic Acid

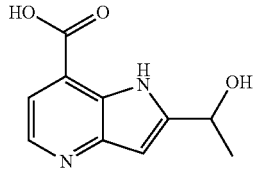

The title compound was prepared in 68% yield using (±)-methyl 2-(1-hydroxyethyl)-1H-pyrrolo[3,2-b]pyridine-7-carboxylate according to the procedure for the preparation of Example 5. $^1$H NMR (400 MHz, DMSO-d$_6$): δ ppm 1.49 (3H, d, J=6.4 Hz), 5.00 (1H, m), 5.50 (1H, s), 6.51 (1H, d, J=2.0 Hz), 7.49 (1H, d, J=5.2 Hz), 8.41 (1H, d, J=4.8 Hz), 10.80 (1H, s). LCMS (mobile phase: 0-60% Acetonitrile-Water-0.02% NH$_4$Ac): purity is >95%, Rt=2.688 min. [M+H] calc'd for C$_{10}$H$_{10}$N$_2$O$_3$, 207; found 207.

Example 19: (±)-methyl 2-[hydroxy(phenyl)methyl]-1H-pyrrolo[3,2-b]-pyridine-7-carboxylate

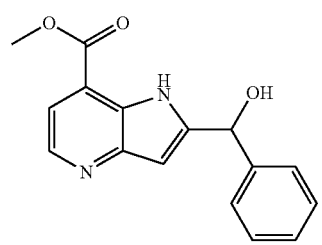 [SMILES: COC(=O)c1ccnc2cc(C(O)c3ccccc3)[nH]c12]

The title compound was prepared in 3% yield using (±)-1-phenyl-2-propyn-1-ol according to the procedure for the preparation of Example 9. $^1$H NMR (400 MHz, CDCl$_3$): δ ppm 3.96 (3H, s), 6.06 (1H, s), 6.54 (1H, s), 7.27-7.31 (3H, m), 7.33-7.40 (2H, m), 7.57 (1H, d, J=5.2 Hz), 8.42 (1H, d, J=5.2 Hz), 9.71 (1H, s). LCMS (mobile phase: 10-95% Acetonitrile-Water-0.02% NH$_4$Ac): purity is >95%, Rt=2.978 min. [M+H] calc'd for C$_{16}$H$_{14}$N$_2$O$_3$, 283; found 283.

Example 20: (±)-2-[hydroxy(phenyl)methyl]-1H-pyrrolo[3,2-b]pyridine-7-carboxylic Acid

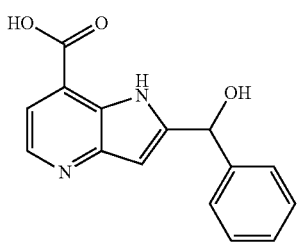 [SMILES: O=C(O)c1ccnc2cc(C(O)c3ccccc3)[nH]c12]

The title compound was prepared in 68% yield using (±)-methyl 2-[hydroxy(phenyl)-methyl]-1H-pyrrolo[3,2-b]pyridine-7-carboxylate according to the procedure for the preparation of Example 5. $^1$H NMR (400 MHz, DMSO-d$_6$):

δ ppm 6.05 (1H, d, J=4.0 Hz), 6.20 (1H, d, J=4.8 Hz), 6.43 (1H, d, J=1.2 Hz), 7.25-7.29 (1H, m), 7.33-7.37 (2H, m), 7.46-7.51 (3H, m), 8.42 (1H, d, J=4.8 Hz), 10.94 (1H, s). LCMS (mobile phase: 5-60% Acetonitrile-Water-0.02% NH$_4$Ac): purity is >95%, Rt=2.217 min. [M+H] calc'd for C$_{15}$H$_{12}$N$_2$O$_3$, 269; found 269.

Example 21: (±)-Methyl 2-[hydroxy-(3-methylphenyl)methyl]-1H-pyrrolo[3,2-b]-pyridine-7-carboxylate

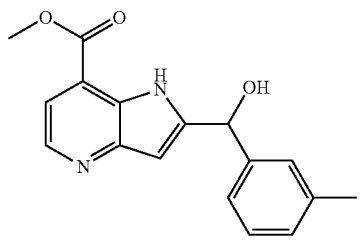

The title compound was prepared in 27% yield using (±)-1-(3-methylphenyl)prop-2-yn-1-ol according to the procedure for the preparation of example 4. $^1$H NMR (400 MHz, CDCl$_3$): δ ppm 2.36 (s, 4H), 4.02 (s, 3H), 6.08 (s, 1H), 6.56-6.63 (m, 1H), 7.14-7.20 (m, 1H), 7.28-7.34 (m, 2H), 7.61 (d, J=5.05 Hz, 1H), 8.51 (d, J=5.05 Hz, 1H), 9.68 (br. s., 1H). [M+H] calc'd for C$_{17}$H$_{16}$N$_2$O$_3$, 297; found 297.

Example 22: (±)-2-[hydroxy-(3-methylphenyl)methyl]-1H-pyrrolo[3,2-b]-pyridine-7-carboxylic Acid

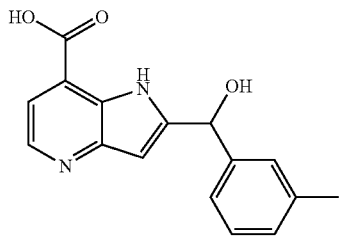 [SMILES: Cc1cccc(C(O)c2cc3nccc(C(=O)O)c3[nH]2)c1]

The title compound was prepared in 90% yield using (±)-methyl 2-[hydroxy-(3-methyl-phenyl)methyl]-1H-pyrrolo[3,2-b]pyridine-7-carboxylate according to the procedure for the preparation of Example 5. $^1$H NMR (400 MHz, DMSO-d$_6$): δ ppm 2.29 (s, 3H), 6.00 (d, J=5.56 Hz, 1H), 6.15 (d, J=5.05 Hz, 1H), 6.39-6.50 (m, 1H), 7.04-7.13 (m, 1H), 7.24 (s, 3H), 7.48 (s, 1H), 8.40 (d, J=4.80 Hz, 1H), 10.86 (br. s., 1H), 13.75 (br. s., 1H). [M+H] calc'd for C$_{16}$H$_{14}$N$_2$O$_3$, 283; found 283.

Example 23: (±)-methyl 2-[hydroxy-(3-methoxyphenyl)methyl]-1H-pyrrolo[3,2-b]pyridine-7-carboxylate

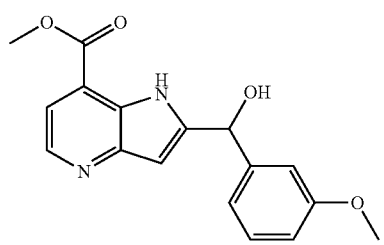

The title compound was prepared in 27% yield using (±)-1-(3-methoxyphenyl)prop-2-yn-1-ol according to the procedure for the preparation of Example 4. $^1$H NMR (400 MHz, CDCl$_3$) δ ppm 3.81 (s, 3H), 4.03 (s, 3H), 6.10 (s, 1H), 6.65 (s, 1H), 6.85-6.95 (m, 1H), 6.99-7.07 (m, 2H), 7.29-7.36 (m, 2H), 7.65 (d, J=5.31 Hz, 1H), 8.51 (d, J=5.31 Hz, 1H), 9.77 (br. s., 1H). [M+H] calc'd for C$_{17}$H$_{16}$N$_2$O$_4$, 313; found 313.

Example 24: (±)-2-[hydroxy-(3-methoxyphenyl)methyl]-1H-pyrrolo[3,2-b]-pyridine-7-carboxylic Acid

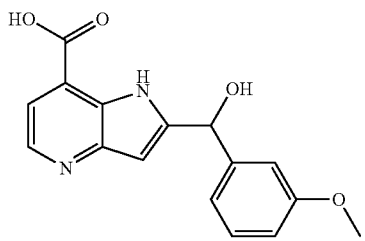 [SMILES: COc1cccc(C(O)c2cc3nccc(C(=O)O)c3[nH]2)c1]

The title compound was prepared in 90% yield using (±)-methyl 2-[hydroxy-(3-methoxy-phenyl)methyl]-1H-pyrrolo[3,2-b]pyridine-7-carboxylate according to the procedure for the preparation of Example 5. $^1$H NMR (400 MHz, DMSO-d$_6$): δ ppm 3.74 (s, 3H), 6.01 (d, J=5.31 Hz, 1H), 6.19 (d, J=5.56 Hz, 1H), 6.43 (s, 1H), 6.83 (dd, J=8.08, 2.53 Hz, 1H), 6.98-7.13 (m, 2H), 7.26 (t, J=7.83 Hz, 1H), 7.40-7.58 (m, 1H), 8.40 (d, J=5.05 Hz, 1H), 10.89 (br. s., 1H), 13.77 (br. s., 1H). [M+H] calc'd for C$_{16}$H$_{14}$N$_2$O$_4$, 299; found 299.

Example 25: (±)-methyl 2-(1-hydroxypropyl)-1H-pyrrolo[3,2-b]pyridine-7-carboxylate

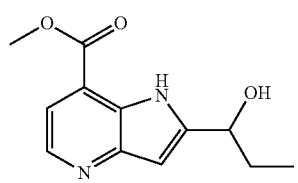 [SMILES: CCC(O)c1cc2nccc(C(=O)OC)c2[nH]1]

The title compound was prepared in 3% yield using (±)-1-pentyn-3-ol according to the procedure for the preparation of Example 9. $^1$H NMR (400 MHz, CDCl$_3$): δ 0.94 (3H, t, J=7.2 Hz), 1.84-1.88 (2H, m), 3.62 (1H, bs), 3.94 (3H, s), 4.85 (1H, t, J=5.6 Hz), 6.46 (1H, s), 7.49 (1H, s), 8.36 (1H, s), 9.74 (1H, s). LCMS (mobile phase: 10-95% Acetonitrile-Water-0.02% NH$_4$Ac): purity is >95%, Rt=2.523 min. [M+H] calc'd for C$_{12}$H$_{14}$N$_2$O$_3$, 235; found 235.

Example 26: (±)-2-(1-hydroxypropyl)-1H-pyrrolo[3,2-b]pyridine-7-carboxylic Acid

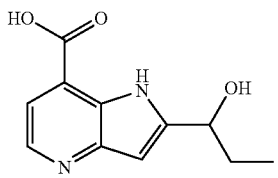 [SMILES: CCC(O)c1cc2nccc(C(=O)O)c2[nH]1]

The title compound was prepared in 50% yield using (±)-methyl 2-(1-hydroxypropyl)-1H-pyrrolo[3,2-b]pyridine-7-carboxylate according to the procedure for the preparation of Example 5. $^1$H NMR (400 MHz, DMSO-d$_6$): δ ppm 0.92 (3H, t, J=7.2 Hz), 1.72-1.89 (2H, m), 4.76-4.81 (1H, m), 5.43 (1H, d, J=5.6 Hz), 6.51 (1H, d, J=2.0 Hz), 7.49 (1H, d, J=5.2 Hz), 8.40 (1H, d, J=5.2 Hz), 10.75 (1H, s). LCMS (mobile phase: 0-60% Acetonitrile-Water-0.02% NH$_4$Ac): purity is >95%, Rt=2.887 min. [M+H] calc'd for C$_{11}$H$_{12}$N$_2$O$_3$, 221; found 221.

Example 27: 2-(1-hydroxycyclopentyl)-1H-pyrrolo[3,2-b]pyridine-7-carboxylic Acid

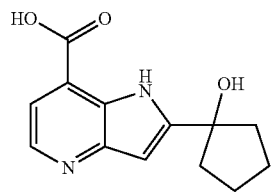 [SMILES: O=C(O)c1ccnc2cc(C3(O)CCCC3)[nH]c12]

The title compound was prepared in 37% yield using 1-ethynylcyclopropanol according to the procedure for the preparation of Examples 4 and 5. $^1$H NMR (400 MHz, DMSO-d$_6$): δ ppm 1.71-2.15 (m, 8H), 5.43 (s, 1H), 6.52 (d, J=1.77 Hz, 1H), 7.49 (d, J=4.80 Hz, 1H), 8.42 (br. s., 1H), 10.40 (br. s., 1H), 13.81 (br. s., 1H). [M+H] calc'd for C$_{13}$H$_{14}$N$_2$O$_3$, 247; found 247.

Example 28: methyl 2-cyclopentyl-1H-pyrrolo[3,2-b]pyridine-7-carboxylate

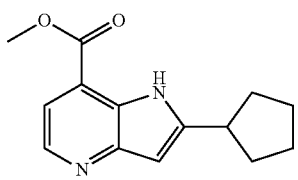 [SMILES: COC(=O)c1ccnc2cc(C3CCCC3)[nH]c12]

The title compound was prepared in 40% yield using 1-ethynylcyclopentane according to the procedure for the preparation of Example 4. $^1$H NMR (400 MHz, CDCl$_3$): δ ppm 1.76-1.91 (m, 6H), 2.12-2.27 (m, 2H), 3.21-3.35 (m, 1H), 4.04 (s, 3H), 6.59 (d, J=1.01 Hz, 1H), 7.57 (d, J=5.05 Hz, 1H), 8.48 (d, J=5.05 Hz, 1H), 9.28-9.55 (m, 1H). [M+H] calc'd for C$_{14}$H$_{16}$N$_2$O$_2$, 245; found 245.

Example 29: 2-cyclopentyl-1H-pyrrolo[3,2-b]pyridine-7-carboxylic Acid

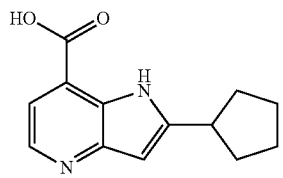 [SMILES: O=C(O)c1ccnc2cc(C3CCCC3)[nH]c12]

The title compound was prepared in 83% yield using 2-cyclopentyl-1H-pyrrolo[3,2-b]-pyridine-7-carboxylic acid according to procedure for the preparation of Example 5. $^1$H NMR (400 MHz, DMSO-d$_6$): δ ppm 1.56-1.84 (m, 6H), 1.98-2.20 (m, 2H), 3.36-3.42 (m, 1H), 6.41 (s, 1H), 7.39-7.49 (m, 1H), 7.43 (d, J=4.55 Hz, 1H), 8.35 (d, J=4.80 Hz, 1H), 11.03 (br. s., 1H), 13.61 (br. s., 1H). [M+H] calc'd for C$_{13}$H$_{14}$N$_2$O$_2$, 231; found 231.

Example 30: (±)-methyl 2-(1-hydroxy-2-methylpropyl)-1H-pyrrolo[3,2-b]-pyridine-7-carboxylate

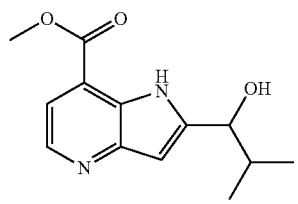 [SMILES: COC(=O)c1ccnc2cc(C(O)C(C)C)[nH]c12]

The title compound was prepared in 7% yield using (±)-4-methyl-pentyn-3-ol according to the procedure for the preparation of Example 9. $^1$H NMR (400 MHz, CDCl$_3$): δ ppm 0.93 (6H, d, J=6.8 Hz), 2.04-2.11 (1H, m), 3.98 (3H, s), 4.74 (1H, d, J=6.0 Hz), 6.58 (1H, d, J=2.0 Hz), 7.56 (1H, d, J=5.2 Hz), 8.43 (1H, d, J=5.2 Hz), 9.70 (1H, s). LCMS (mobile phase: 10-95% Acetonitrile-Water-0.02% NH$_4$Ac): purity is >95%, Rt=2.826 min. [M+H] calc'd for C$_{13}$H$_{16}$N$_2$O$_3$, 249; found 249.

Example 31: (±)-2-(1-hydroxy-2-methylpropyl)-1H-pyrrolo[3,2-b]-pyridine-7-carboxylic Acid

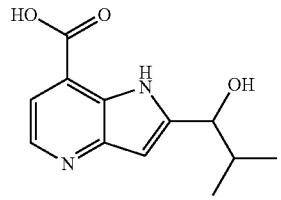 [SMILES: CC(C)C(O)c1cc2nccc(C(=O)O)c2[nH]1]

The title compound was prepared in 30% yield using (±)-methyl 2-(1-hydroxy-2-methyl-propyl)-1H-pyrrolo[3,2-b]pyridine-7-carboxylate according to procedure for the preparation of Example 5. $^1$H NMR (400 MHz, DMSO-d$_6$): δ ppm 0.88 (6H, d, J=6.8 Hz), 2.03-2.08 (1H, m), 4.63-4.64 (1H, m), 5.42-5.44 (1H, m), 6.52 (1H, d, J=2.0 Hz), 7.50 (1H, d, J=5.2 Hz), 8.42 (1H, d, J=5.2 Hz), 10.76 (1H, s).

LCMS (mobile phase: 0-60% Acetonitrile-Water-0.02% NH₄Ac): purity is >95%, Rt=3.175 min. [M+1-1] calc'd for C₁₂H₁₄N₂O₃, 235; found 235.

Example 32: (±)-methyl 2-[cyclopropyl(hydroxy)methyl]-1H-pyrrolo[3,2-b]-pyridine-7-carboxylate

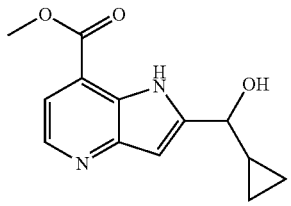

The title compound was prepared in 7% yield using (±)-3-cyclopropylpropyn-3-ol according to the procedure for the preparation of Example 9. ¹H NMR (400 MHz, CDCl₃): δ ppm 0.57-0.65 (2H, m), 0.76-0.83 (2H, m), 1.39-1.46 (1H, m), 4.09 (3H, s), 4.37 (1H, d, J=8.4 Hz), 6.80 (1H, s), 7.68 (1H, bs), 8.59 (1H, br), 9.81 (1H, s). LCMS (mobile phase: 10%-95% Acetonitrile-Water-0.02% NH₄Ac): purity is >95%, Rt=2.555 min. [M+H] calc'd for C₁₃H₁₄N₂O₃, 247; found 247.

Example 33: (±)-2-[cyclopropyl(hydroxy)methyl]-1H-pyrrolo[3,2-b]-pyridine-7-carboxylic Acid

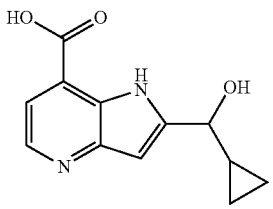

The title compound was prepared in 30% yield using methyl 2-[cyclopropyl(hydroxy)-methyl]-1H-pyrrolo[3,2-b]pyridine-7-carboxylate according to procedure for the preparation of Example 5. ¹H NMR (400 MHz, DMSO-d₆): δ ppm 0.42-0.53 (4H, m), 1.26-1.30 (1H, m), 4.31 (1H, t, J=6.8 Hz), 5.53 (1H, d, J=5.6 Hz), 6.57 (1H, d, J=2.0 Hz), 7.50 (1H, d, J=4.8 Hz), 8.42 (1H, d, J=5.2 Hz), 10.68 (1H, s). LCMS (mobile phase: 0-60% Acetonitrile-Water-0.02% NH₄Ac): purity is >95%, Rt=2.931 min. [M+H] calc'd for C₁₂H₁₂N₂O₃, 233; found 233.

Example 34: 2-[(3-methoxyphenyl)methyl]-1H-pyrrolo[3,2-b]pyridine-7-carboxylic Acid

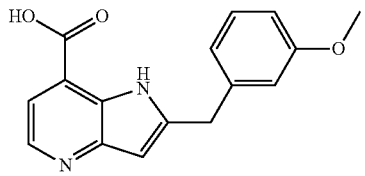

A mixture containing methyl 2-[hydroxy-(3-methoxyphenyl)methyl]-1H-pyrrolo[3,2-b]-pyridine-7-carboxylate (31 mg, 0.1 mmol), Et₃SiH (160 μL, 1 mmol), and TFA (149 μL, 2 mmol) was stirred at 60° C. for 16 hr. The reaction was concentrated in vacuo and purified by column chromatography (0%-50% EtOAc/Hex) to afford methyl-2-[(3-methoxyphenyl)methyl]-1H-pyrrolo[3,2-b]pyridine-7-carboxylate, which was converted to the title compound (21 mg, 70%) according to procedure for Example 5. ¹H NMR (400 MHz, DMSO-d₆): δ ppm 3.66 (s, 4H), 4.12 (s, 2H), 6.30 (s, 1H), 6.73 (d, J=8.34 Hz, 1H), 6.79-6.95 (m, 3H), 7.15 (t, J=7.83 Hz, 1H), 7.39 (d, J=4.80 Hz, 1H), 8.30 (d, J=4.55 Hz, 1H), 11.19 (br. s., 1H), 13.60 (br. s., 1H). [M+H] calc'd for C₁₆H₁₄N₂O₃, 283; found 283.

Example 35: methyl 2-[(3-methylphenyl)methyl]-1H-pyrrolo[3,2-b]pyridine-7-carboxylate

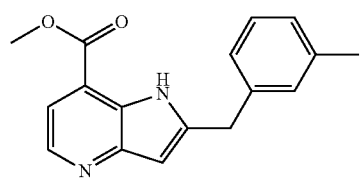

The title compound was prepared in 74% yield using methyl 2-[hydroxy-(3-methylphenyl)-methyl]-1H-pyrrolo[3,2-b]pyridine-7-carboxylate according to the procedure for the preparation of Example 34. ¹H NMR (400 MHz, CDCl₃): δ ppm 2.33 (s, 3H), 3.97 (s, 3H), 4.16 (s, 2H), 6.47-6.75 (m, 1H), 7.07 (s, 3H), 7.17-7.33 (m, 1H), 7.50-7.70 (m, 1H), 8.40-8.83 (m, 1H), 9.18-9.49 (m, 1H). [M+H] calc'd for C₁₇H₁₆N₂O₂, 281; found 283.

Example 36: 2-[(3-methylphenyl)methyl]-1H-pyrrolo[3,2-b]pyridine-7-carboxylic Acid

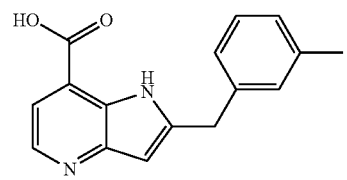

The title compound was prepared in 98% yield using methyl 2-[(3-methylphenyl)methyl]-1H-pyrrolo[3,2-b]pyridine-7-carboxylate according to procedure for the preparation of Example 5. ¹H NMR (400 MHz, DMSO-d₆): δ ppm 2.27 (s, 3H), 4.13-4.24 (m, 2H), 6.35 (s, 1H), 7.03 (d, J=7.33 Hz, 1H), 7.08-7.27 (m, 4H), 7.45 (d, J=5.05 Hz, 1H), 8.37 (d, J=5.05 Hz, 1H), 11.25 (br. s., 1H), 13.65 (br. s., 1H). [M+H] calc'd for C₁₆H₁₄N₂O₂, 267; found 267.

Example 37: (±)-methyl 2-(2-cyclopropyl-1-hydroxyethyl)-1H-pyrrolo[3,2-b]-pyridine-7-carboxylate

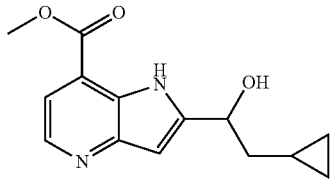 [SMILES: COC(=O)c1ccnc2cc(C(O)CC3CC3)[nH]c12]

A solution of 2-cyclopropylacetaldehyde (6.0 g, 71 mmol) in 15 mL THF was added to a solution of ethynylmagnesium bromide (0.5 M, 214 mL, 107 mmol) at 0° C. After 1.5 hr, saturated NH$_4$Cl solution (75 mL) was added the mixture was extracted with EtOAc. The organic layers were successively washed water, brine, dried over Na$_2$SO$_4$ and concentrated in vacuo. The residue was purified by flash chromatography (EA/PE=1/5) to afford (±)-4-cyclopropylbutyn-3-ol (700 mg, 9%). $^1$H NMR (400 MHz, CDCl$_3$): δ ppm 0.03-0.17 (2H, m), 0.31-0.37 (2H, m), 0.71-0.76 (1H, m), 1.42-1.57 (2H, m), 2.33 (1H, d, J=2.4 Hz), 4.29-4.32 (1H, m).

The title compound was prepared in 6% yield using (±)-4-cyclopropylbutyn-3-ol according to the procedure for the preparation of Example 9. $^1$H NMR (400 MHz, CDCl$_3$): δ ppm 0.15-0.21 (2H, m), 0.48-0.58 (2H, m), 0.82-0.86 (1H, m), 1.85 (2H, t, J=6.8 Hz), 4.04 (3H, s), 5.12 (1H, t, J=6.8 Hz), 6.62 (1H, s), 7.61 (1H, bs), 8.52 (1H, bs), 9.75 (1H, s). LCMS (mobile phase: 10-95% Acetonitrile-Water-0.02% NH$_4$Ac): purity is >95%, Rt=2.869 min. [M+H] calc'd for C$_{14}$H$_{16}$N$_2$O$_3$, 261; found 261.

Example 38: (±)-2-(2-cyclopropyl-1-hydroxyethyl)-1H-pyrrolo[3,2-b]-pyridine-7-carboxylic Acid

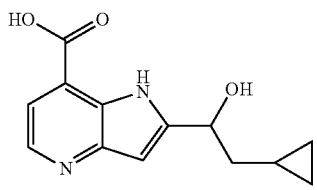 [SMILES: O=C(O)c1ccnc2cc(C(O)CC3CC3)[nH]c12]

The title compound was prepared in 32% yield using (±)-methyl 2-(2-cyclopropyl-1-hydroxyethyl)-1H-pyrrolo[3,2-b]pyridine-7-carboxylate according to procedure for the preparation of Example 5. $^1$H NMR (400 MHz, DMSO-d$_6$): δ ppm 0.05-0.15 (2H, m), 0.35-0.42 (2H, m), 0.85-0.89 (1H, m), 1.51-1.57 (1H, m), 1.80-1.87 (1H, m), 5.01-5.04 (1H, m), 6.78 (1H, s), 7.82 (1H, d, J=5.6 Hz), 8.63 (1H, d, J=3.6 Hz), 11.95 (1H, s). LCMS (mobile phase: 0-60% Acetonitrile-Water-0.02% NH$_4$Ac): purity is >95%, Rt=3.313 min. [M+H] calc'd for C$_{13}$H$_{14}$N$_2$O$_3$, 247; found 247.

Example 39: 2-(phenoxymethyl)-1H-pyrrolo[3,2-b]pyridine-7-carboxylic Acid

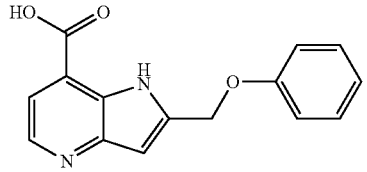

The title compound was prepared in 1% yield using phenylpropargylether according to the procedure for the preparation of Examples 4 and 5. $^1$H NMR (400 MHz, DMSO-d$_6$): δ ppm 5.33 (s, 2H), 6.74 (s, 1H), 6.90-6.99 (m, 1H), 7.05 (d, J=8.59 Hz, 2H), 7.29-7.37 (m, 2H), 7.55 (d, J=4.80 Hz, 1H), 8.45 (d, J=4.80 Hz, 1H), 11.50 (br. s., 1H), 13.75 (br. s., 1H). [M+H] calc'd for C$_{15}$H$_{12}$N$_2$O$_3$, 269; found 269.

Example 40: methyl 2-(methoxymethyl)-1H-pyrrolo[3,2-b]pyridine-7-carboxylate

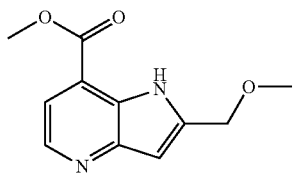

The title compound was prepared in 17% yield using methylpropargylether according to the procedure for the preparation of Example 4. $^1$H NMR (400 MHz, CDCl$_3$): δ ppm 3.45-3.50 (m, 3H), 4.07 (s, 3H), 4.73 (s, 2H), 6.84 (br. s., 1H), 7.68-7.75 (m, 1H), 8.55 (d, J=5.31 Hz, 1H), 9.70-9.89 (m, 1H). [M+H] calc'd for C$_{11}$H$_{12}$N$_2$O$_3$, 221; found 221.

Example 41: 2-(methoxymethyl)-1H-pyrrolo[3,2-b]pyridine-7-carboxylic Acid

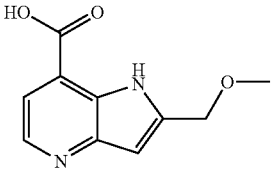

The title compound was prepared in 26% yield using methyl 2-(methoxymethyl)-1H-pyrrolo[3,2-b]pyridine-7-carboxylate according to the procedure for the preparation of Example 5. $^1$H NMR (400 MHz, DMSO-d$_6$): δ ppm 3.34 (s, 2H), 4.65 (s, 2H), 6.55-6.67 (m, 1H), 7.52 (d, J=4.80 Hz, 1H), 8.43 (d, J=4.80 Hz, 1H), 11.23 (br. s., 1H), 13.72 (br. s., 1H). [M+H] calc'd for C$_{10}$H$_{10}$N$_2$O$_3$, 207; found 207.

Example 42: (±)-methyl 2-[hydroxy(oxan-4-yl)methyl]-1H-pyrrolo[3,2-b]-pyridine-7-carboxylate

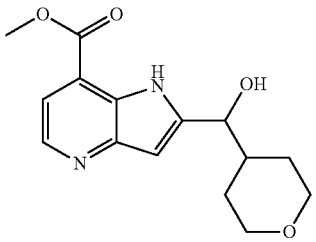 [SMILES: COC(=O)c1ccnc2cc(C(O)C3CCOCC3)[nH]c12]

The title compound was prepared in 32% yield using (±)-1-(oxan-4-yl)-1-prop-2-yn-1-ol according to the procedure for the preparation of Example 9. $^1$H NMR (400 MHz, CDCl$_3$): δ ppm 1.47-1.57 (3H, m), 1.86-1.89 (1H, m), 2.03-2.10 (1H, m), 3.39-3.46 (2H, m), 3.98-4.07 (2H, m), 4.09 (3H, s), 4.82 (1H, d, J=6.8 Hz), 6.64 (1H, s), 7.65 (1H, d, J=4.8 Hz), 8.55 (1H, d, J=4.4 Hz), 9.75 (1H, s). LCMS (mobile phase: 10-95% Acetonitrile-Water-0.02% NH$_4$Ac): purity is >95%, Rt=2.433 min. [M+H] calc'd for C$_{15}$H$_{18}$N$_2$O$_4$, 291; found 291.

Example 43: (±)-2-[hydroxy(oxan-4-yl)methyl]-1H-pyrrolo[3,2-b]-pyridine-7-carboxylic Acid

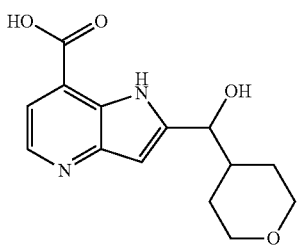 [SMILES: O=C(O)c1ccnc2cc(C(O)C3CCOCC3)[nH]c12]

The title compound was prepared in 54% yield (±)-methyl 2-[hydroxy(oxan-4-yl)methyl]-1H-pyrrolo[3,2-b]pyridine-7-carboxylate according to the procedure for the preparation of Example 5. $^1$H NMR (400 MHz, CD$_3$OD): δ ppm 1.30-1.33 (1H, m), 1.43-1.60 (3H, m), 1.94-2.01 (1H, m), 3.26-3.38 (2H, m), 3.82-3.89 (2H, m), 4.75 (1H, d, J=6.0 Hz), 6.67 (1H, s), 7.80 (1H, d, J=5.6 Hz), 8.41 (1H, d, J=5.6 Hz). LCMS (mobile phase: 0-60% Acetonitrile-Water-0.02% NH$_4$Ac): purity is >95%, Rt=2.873 min. [M+H] calc'd for C$_{14}$H$_{16}$N$_2$O$_4$, 277; found 277.

Example 44: 2-[(4-chlorophenyl)methyl]-1H-pyrrolo[3,2-b]pyridine-7-carboxylic Acid

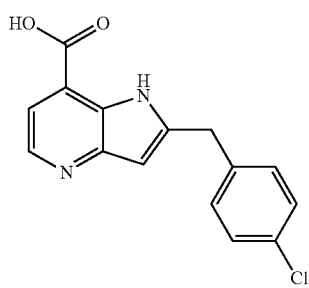 [SMILES: O=C(O)c1ccnc2cc(Cc3ccc(Cl)cc3)[nH]c12]

The title compound was prepared in 4% yield using 1-chloro-4-(prop-2-yn-1-yl)benzene according to the procedure for the preparation of Examples 4 and 5. $^1$H NMR (400 MHz, DMSO-d$_6$): δ ppm 4.22 (s, 2H), 6.37 (s, 1H), 7.37 (s, 4H), 7.46 (d, J=4.80 Hz, 1H), 8.37 (d, J=4.80 Hz, 1H), 11.31 (br. s., 1H), 13.61-13.73 (m, 1H). [M+H] calc'd for C$_{15}$H$_{11}$N$_2$O$_2$Cl, 287; found 287.

Example 45: (±)-methyl 2-(1-hydroxy-1-phenyl-ethyl)-1H-pyrrolo[3,2-b]-pyridine-7-carboxylate

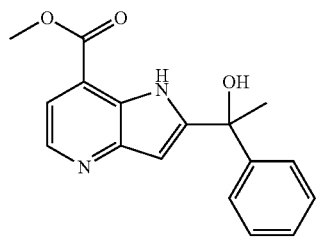 [SMILES: COC(=O)c1ccnc2cc(C(C)(O)c3ccccc3)[nH]c12]

The title compound was prepared in 31% yield using (±)-2-phenyl-3-butyn-2-ol according to the procedure for the preparation of example 4. $^1$H NMR (400 MHz, CDCl$_3$): δ ppm 2.09 (s, 3H), 4.01 (s, 3H), 6.77-6.89 (m, 1H), 7.28-7.41 (m, 5H), 7.45-7.55 (m, 3H), 7.65 (d, J=5.05 Hz, 1H), 8.51 (d, J=5.05 Hz, 1H), 9.69 (br. s., 1H). [M+H] calc'd for C$_{17}$H$_{16}$N$_2$O$_3$, 297; found 297.

Example 46: (±)-2-(1-hydroxy-1-phenylethyl)-1H-pyrrolo[3,2-b]pyridine-7-carboxylic Acid

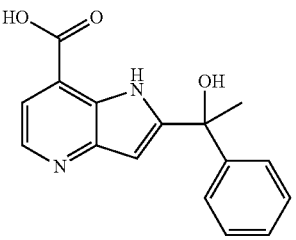 [SMILES: CC(O)(c1ccccc1)c1cc2nccc(C(=O)O)c2[nH]1]

The title compound was prepared in 84% yield using (±)-methyl 2-(1-hydroxy-1-phenylethyl)-1H-pyrrolo[3,2-b]pyridine-7-carboxylate according to the procedure for the preparation of Example 5. $^1$H NMR (400 MHz, DMSO-d$_6$): δ ppm 1.89 (s, 3H), 6.36 (s, 1H), 6.68 (d, J=2.02 Hz, 1H), 7.20-7.26 (m, 1H), 7.32 (t, J=7.58 Hz, 2H), 7.42 (d, J=7.33 Hz, 2H), 7.51 (d, J=4.80 Hz, 1H), 8.45 (s, 1H), 10.28 (br. s., 1H), 13.80 (br. s., 1H). [M+H] calc'd for C$_{16}$H$_{14}$N$_2$O$_3$, 283; found 283.

Example 47: (±)-methyl 2-[hydroxy-(2-methylpyrazol-3-yl)methyl]-1H-pyrrolo[3,2-b]-pyridine-7-carboxylate

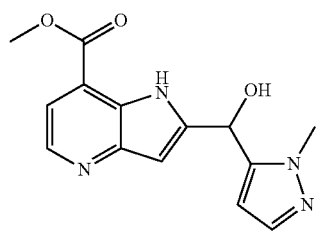

The title compound was prepared in 2% yield using 1-methyl-1H-pyrazole-5-carbaldehyde according to the procedure for the preparation of Example 37. $^1$H NMR (400 MHz, DMSO-$d_6$): δ ppm 3.86 (3H, s), 3.97 (3H, s), 5.93 (1H, d, J=1.6 Hz), 6.19 (1H, d, J=6.4 Hz), 6.34 (1H, d, J=6.4 Hz), 6.59 (1H, d, J=1.2 Hz), 7.29 (1H, d, J=2.0 Hz), 7.56 (1H, d, J=4.8 Hz), 8.43 (1H, d, J=4.8 Hz), 11.14 (1H, s). LCMS (mobile phase: 5%-95% Acetonitrile-Water-0.02% NH$_4$Ac): purity is >95%, Rt=2.514 min. [M+H] calc'd for $C_{14}H_{14}N_4O_3$, 287; found 287.

Example 48: (±)-2-[hydroxy-(2-methylpyrazol-3-yl)methyl]-1H-pyrrolo[3,2-b]-pyridine-7-carboxylic Acid

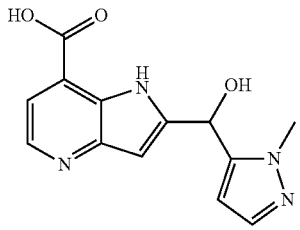 [SMILES: Cn1nccc1C(O)c1cc2nccc(C(=O)O)c2[nH]1]

The title compound was prepared in 65% yield using (±)-methyl 2-[hydroxy-(2-methyl-pyrazol-3-yl)methyl]-1H-pyrrolo[3,2-b]pyridine-7-carboxylate according to the procedure for the preparation of Example 5. $^1$H NMR (400 MHz, CD$_3$OD): δ ppm 3.93 (3H, s), 6.16 (1H, d, J=1.6 Hz), 6.32 (1H, s), 6.65 (1H, d, J=0.8 Hz), 7.42 (1H, d, J=1.6 Hz), 7.80 (1H, d, J=5.2 Hz), 7.48 (1H, d, J=4.8 Hz). LCMS (mobile phase: 0-60% Acetonitrile-Water-0.02% NH$_4$Ac): purity is >95%, Rt=2.762 min. [M+H] calc'd for $C_{13}H_{12}N_4O_3$, 273; found 273.

Example 49: (±)-methyl 2-[hydroxy-(1-methylpyrazol-4-yl)methyl]-1H-pyrrolo[3,2-b]pyridine-7-carboxylate

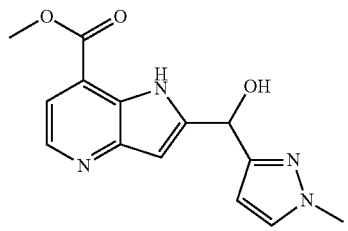

The title compound was prepared in 3% yield using 1-methyl-1H-pyrazole-4-carbaldehyde according to the procedure for the preparation of Example 37. $^1$H NMR (400 MHz, DMSO-$d_6$): δ ppm 3.78 (3H, s), 3.98 (3H, s), 5.91 (1H, d, J=7.2 Hz), 5.97 (1H, d, J=6.0 Hz), 6.51 (1H, d, J=1.6 Hz), 7.38 (1H, s), 7.52 (1H, d, J=4.8 Hz), 7.55 (1H, s), 8.43 (1H, d, J=4.8 Hz), 10.96 (1H, s). LCMS (mobile phase: 5%-95% Acetonitrile-Water-0.02% NH$_4$Ac): purity is >95%, Rt=2.407 min. [M+H] calc'd for $C_{14}H_{14}N_4O_3$, 287; found 287.

Example 50: (±)-2-[hydroxy-(1-methylpyrazol-4-yl)methyl]-1H-pyrrolo[3,2-b]pyridine-7-carboxylic Acid

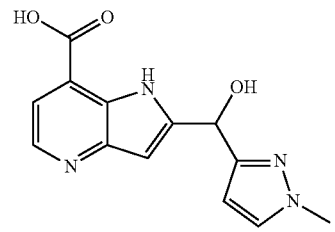 [SMILES: Cn1ccc(C(O)c2cc3nccc(C(=O)O)c3[nH]2)n1]

The title compound was prepared in 70% yield using (±)-methyl 2-[hydroxy-(1-methylpyrazol-4-yl)methyl]-1H-pyrrolo[3,2-b]pyridine-7-carboxylate according to the procedure for the preparation of Example 5. $^1$H NMR (400 MHz, DMSO-$d_6$): δ ppm 3.78 (3H, s), 6.07 (1H, s), 6.72 (1H, s), 7.39 (1H, s), 7.58 (1H, s), 7.80 (1H, d, J=5.6 Hz), 8.62 (1H, d, J=5.6 Hz), 11.87 (1H, s). LCMS (mobile phase: 0%-60% Acetonitrile-Water-0.02% NH$_4$Ac): purity is >95%, Rt=2.686 min. [M+H] calc'd for $C_{13}H_{12}N_4O_3$, 273; found 273.

Example 51: methyl 2-(cyclopentylmethyl)-1H-pyrrolo[3,2-b]pyridine-7-carboxylate

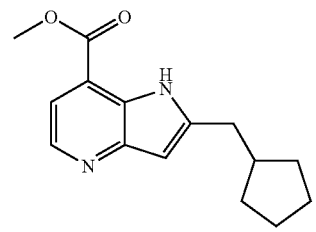 [SMILES: COC(=O)c1ccnc2cc(CC3CCCC3)[nH]c12]

The title compound was prepared in 8% yield using prop-2-ynyl-cyclopentane according to the procedure for the preparation of Example 9. $^1$H NMR (400 MHz, DMSO-$d_6$): δ ppm 1.25-1.29 (2H, m), 1.50-1.54 (2H, m), 1.59-1.65 (2H, m), 1.69-1.75 (2H, m), 2.27-2.34 (1H, m), 2.85 (2H, d, J=7.2 Hz), 3.98 (3H, s), 6.43 (1H, d, J=2.0 Hz), 7.46 (1H, d, J=4.4 Hz), 8.38 (1H, d, J=5.2 Hz), 11.10 (1H, s). LCMS (mobile phase: 10%-95% Acetonitrile-Water-0.02% NH$_4$Ac): purity is >95%, Rt=3.929 min. [M+H] Calc'd for $C_{15}H_{18}N_2O_2$, 259; Found, 259.

Example 52: 2-(cyclopentylmethyl)-1H-pyrrolo[3,2-b]pyridine-7-carboxylic Acid

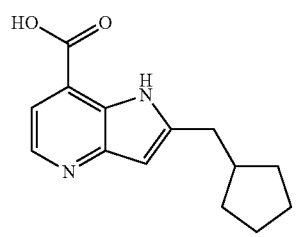 [SMILES: O=C(O)c1ccnc2cc(CC3CCCC3)[nH]c12]

The title compound was prepared in 44% yield using methyl 2-(cyclopentylmethyl)-1H-pyrrolo[3,2-b]pyridine-7-carboxylate according to the procedure for the preparation of Example 5. $^1$H NMR (400 MHz, DMSO-d$_6$): δ ppm 1.22-1.28 (2H, m), 1.47-1.75 (6H, m), 2.25-2.32 (1H, m), 2.84 (2H, d, J=7.2 Hz), 6.40 (1H, s), 7.44 (1H, d, J=4.8 Hz), 8.36 (1H, d, J=3.6 Hz), 11.06 (1H, s), 13.59 (1H, br). LCMS (mobile phase: 0-60% Acetonitrile-Water-0.02% NH$_4$Ac): purity is >95%, Rt=4.194 min. [M+H] calc'd for C$_{14}$H$_{16}$N$_2$O$_2$, 245; found 245.

Example 53: methyl 2-(cyclohexylmethyl)-1H-pyrrolo[3,2-b]pyridine-7-carboxylate

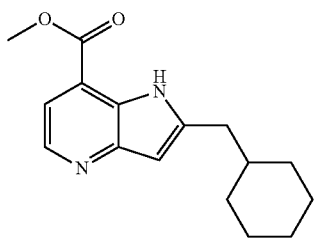

The title compound was prepared in 24% yield using prop-2-ynyl-cyclohexane according to the procedure for the preparation of Example 9. $^1$H NMR (400 MHz, DMSO-d$_6$): δ ppm 0.94-1.04 (2H, m), 1.12-1.25 (3H, m), 1.61-1.75 (6H, m), 2.74 (2H, d, J=7.2 Hz), 3.98 (3H, s), 6.40 (1H, d, J=2.0 Hz), 7.46 (1H, d, J=5.2 Hz), 8.38 (1H, d, J=4.8 Hz), 11.10 (1H, s). [M+H] calc'd for C$_{16}$H$_{20}$N$_2$O$_2$, 273; found 273.

Example 54: 2-(cyclohexylmethyl)-1H-pyrrolo[3,2-b]pyridine-7-carboxylic Acid

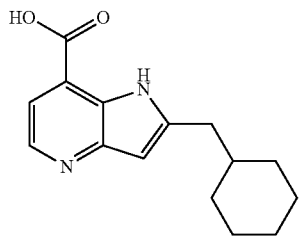 [SMILES: O=C(O)c1ccnc2cc(CC3CCCCC3)[nH]c12]

The title compound was prepared in 42% yield using methyl 2-(cyclohexylmethyl)-1H-pyrrolo[3,2-b]pyridine-7-carboxylate according to the procedure for the preparation of Example 5. $^1$H NMR (400 MHz, DMSO-d$_6$): δ ppm 0.93-0.99 (2H, m), 1.16-1.24 (3H, m), 1.60-1.72 (6H, m), 2.74 (2H, d, J=7.0 Hz), 6.38 (1H, s), 7.45 (1H, d, J=5.2 Hz), 8.37 (1H, d, J=3.2 Hz), 11.15 (1H, s). LCMS (mobile phase: 0-60% Acetonitrile-Water-0.02% NH$_4$Ac): purity is >95%, Rt=4.404 min. [M+H] calc'd for C$_{15}$H$_{18}$N$_2$O$_2$, 259; found 259.

Example 55: methyl 2-[[4-(trifluoromethyl)phenyl]methyl]-1H-pyrrolo[3,2-b]pyridine-7-carboxylate

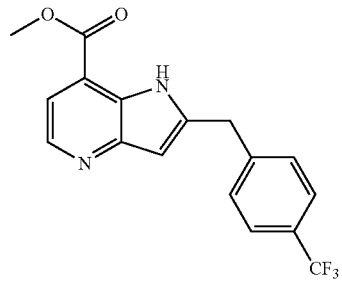 [SMILES: COC(=O)c1ccnc2cc(Cc3ccc(C(F)(F)F)cc3)[nH]c12]

4-(trifluoromethyl)benzaldehyde (2.73 mL, 20 mmol) was added dropwise into a round-bottom flask containing a solution of ethynylMg bromide (50 mL, 25 mmol) in THF at 0° C. After 30 min the reaction was quenched with aq. NH$_4$Cl. The mixture was taken up in EtOAc and washed successively with water, brine, and dried with Na$_2$SO$_4$. The organic layers were concentrated in vacuo to afford 1-[4-trifuoromethyl)phenyl]prop-2-yn-1-ol as a yellow oil (3.65 g, 91%).

To a vial containing 1-[4-trifluoromethyl)phenyl]prop-2-yn-1-ol (1.65 g, 8.25 mmol) was added Et$_3$SiH (3.98 mL, 25 mmol) followed by TFA (3.83 mL, 50 mmol). The reaction was capped and allowed to stir at 60° C. for 16 hr. The reaction was concentrated in vacuo and the residue purified by column chromatography (0-10% EtOAc/hexanes gradient, 12 g silica) to afford 1-(prop-2-yn-1yl)-4-(trifluoromethyl)benzene (325 mg, 21%) as a clear oil.

The title compound was prepared in 17% yield using 1-(prop-2-yn-1yl)-4-(trifluoro-methyl)benzene according to the procedure for the preparation of Example 4. $^1$H NMR (400 MHz, CDCl$_3$): δ ppm 4.00 (s, 3H), 4.28 (s, 2H), 6.59-6.68 (m, 1H), 7.39 (d, J=8.08 Hz, 3H), 7.56-7.67 (m, 4H), 8.53 (d, J=4.80 Hz, 1H), 9.33 (br. s., 1H). [M+H] calc'd for C$_{17}$H$_{13}$N$_2$O$_2$, 335; found 335.

Example 56: 2-[[4-(trifluoromethyl)phenyl]methyl]-1H-pyrrolo[3,2-b]-pyridine-7-carboxylic Acid

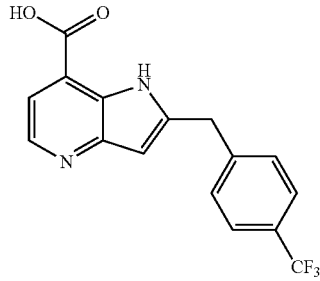 [SMILES: O=C(O)c1ccnc2cc(Cc3ccc(C(F)(F)F)cc3)[nH]c12]

The title compound was prepared in 80% yield using methyl 2-[[4-(trifluoromethyl)-phenyl]methyl]-1H-pyrrolo[3,2-b]pyridine-7-carboxylate according to the procedure for the preparation in Example 5. $^1$H NMR (400 MHz, DMSO-d$_6$): δ ppm 3.32 (s, 3H), 4.33 (s, 2H), 6.42 (s, 1H), 7.47 (d, J=5.05 Hz, 1H), 7.56 (d, J=8.08 Hz, 3H), 7.68 (d, J=8.08 Hz, 3H), 8.39 (s, 1H), 11.38 (br. s., 1H), 13.67 (br. s., 1H). [M+H] calc'd for C$_{16}$H$_{11}$N$_2$O$_2$, 321; found 321.

Example 57: methyl 2-(2-cyanoethyl)-1H-pyrrolo[3,2-b]pyridine-7-carboxylate

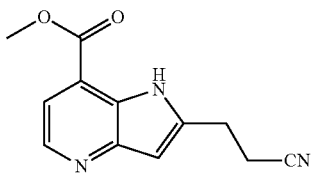 [SMILES: COC(=O)c1ccnc2cc(CCC#N)[nH]c12]

The title compound was prepared in 5% yield using 4-cyano-1-butyne according to the procedure for the preparation of Example 4. $^1$H NMR (400 MHz, CDCl$_3$): δ ppm 2.84 (t, J=7.07 Hz, 2H) 3.28 (t, J=7.20 Hz, 2H) 4.06 (s, 3H) 6.75 (s, 1H) 7.68 (d, J=5.31 Hz, 1H) 8.56 (d, J=5.05 Hz, 1H) 9.58-9.87 (m, 1H). [M+H] calc'd for C$_{12}$H$_{11}$N$_3$O$_2$, 230; found 230.

Example 58: 2-(2-cyanoethyl)-1H-pyrrolo[3,2-b]pyridine-7-carboxylic Acid

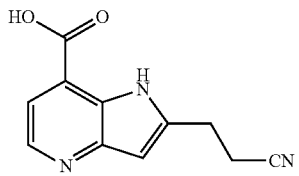 [SMILES: N#CCCc1cc2nccc(C(=O)O)c2[nH]1]

The title compound was prepared in 71% yield using methyl 2-(2-cyanoethyl)-1H-pyrrolo-[3,2-b]pyridine-7-carboxylate according to the procedure for the preparation of Example 5. $^1$H NMR (400 MHz, DMSO-d$_6$): δ ppm 2.98 (t, J=7.07 Hz, 2H) 3.18 (t, J=7.07 Hz, 2H) 6.56-6.59 (m, 1H) 7.50 (d, J=4.80 Hz, 1H) 8.41 (d, J=4.80 Hz, 1H) 11.32 (d, J=1.26 Hz, 1H) 13.71 (br. s., 1H). [M+H] calc'd for C$_{11}$H$_9$N$_3$O$_2$, 216; found 216.

Example 59: 2-[(4-methoxyphenyl)methyl]-1H-pyrrolo[3,2-b]pyridine-7-carboxylic Acid

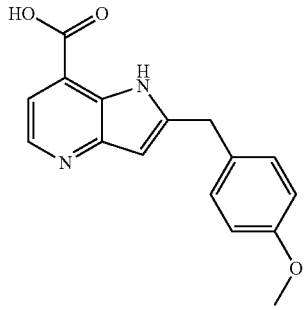 [SMILES: COc1ccc(Cc2cc3nccc(C(=O)O)c3[nH]2)cc1]

To a vial containing 1-[4-methoxy)phenyl]prop-2-yn-1-ol (1.62 g, 10.0 mmol), Et$_3$SiH (1.91 mL, 12 mmol) in DCM (10 mL) at −78° C. was added BF$_3$-Et$_2$O (1.48 mL, 12 mmol) dropwise. The reaction was capped and allowed to stir at −78° C. for 2 hr. The reaction was quenched with saturated NH$_4$Cl and the aqueous layers were extracted with DCM. The combined organic layers were concentrated in vacuo and purified by column chromatography (0-5% EtOAc/hexanes gradient, 12 g silica) to afford 1-methoxy-4-(prop-2-yn-1-yl)benzene (400 mg, 27%) as a clear oil.

The title compound was prepared in 4% yield using 1-methoxy-4-(prop-2-yn-1-yl)benzene according to the procedure for the preparation of Examples 4 and 5. $^1$H NMR (400 MHz, DMSO-d$_6$) δ ppm 3.72 (s, 3H), 4.17 (s, 2H), 6.37 (s, 1H), 6.88 (d, J=8.08 Hz, 2H), 7.27 (d, J=8.34 Hz, 2H), 7.54 (br. s., 1H), 8.42 (br. s., 1H), 11.45-11.56 (m, 1H). [M+H] calc'd for C$_{16}$H$_{14}$N$_2$O$_3$, 283; found 283.

Example 60: 2-[(4-fluorophenoxy)methyl]-1H-pyrrolo[3,2-b]pyridine-7-carboxylic Acid

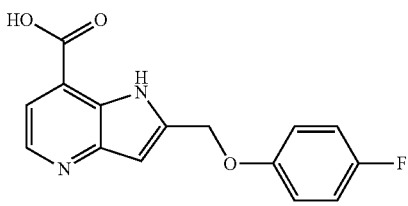 [SMILES: O=C(O)c1ccnc2cc(COc3ccc(F)cc3)[nH]c12]

The title compound was prepared in <1% yield using 1-fluoro-4-(prop-2-yn-1-yloxy)-benzene according to the procedure for the preparation of Examples 9 and 5. $^1$H NMR (400 MHz, CD$_3$OD): δ ppm 5.43 (2H, s), 6.95 (1H, s), 7.05-7.079 (4H, m), 8.02 (1H, br), 8.64 (1H, br). LCMS (mobile phase: 0-60% Acetonitrile-Water-0.02% NH$_4$Ac): purity is >95%, Rt=2.416 min. [M+H] calc'd for C$_{15}$H$_{11}$FN$_2$O$_3$, 287; found 287.

Example 61: methyl-2-[(4-methylphenoxy)methyl]-1H-pyrrolo[3,2-b]-pyridine-7-carboxylate

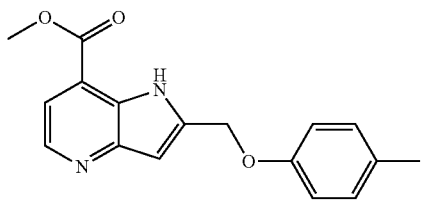

The title compound was prepared in <1% yield using 1-methyl-4-(prop-2-yn-1-yloxy)-benzene according to the procedure for the preparation of Example 9. $^1$H NMR (400 MHz, CD$_3$OD): δ ppm 2.17 (3H, s), 3.96 (3H, s), 5.21 (2H, s), 6.64 (1H, s), 6.84 (2H, d, J=8.8 Hz), 7.00 (2H, d, J=8.4 Hz), 7.60 (1H, d, J=5.2 Hz), 8.32 (1H, d, J=4.8 Hz). [M+H] Calc'd for C$_{17}$H$_{16}$N$_2$O$_3$, 297; Found, 297.

Example 62: 2-[(4-methylphenoxy)methyl]-1H-pyrrolo[3,2-b]pyridine-7-carboxylic Acid

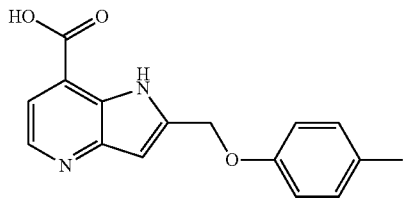 [SMILES: Cc1ccc(OCc2cc3nccc(C(=O)O)c3[nH]2)cc1]

The title compound was prepared in 51% yield using methyl-2-[(4-methylphenoxy)-methyl]-1H-pyrrolo[3,2-b]pyridine-7-carboxylate according to the procedure for the preparation of Example 5. $^1$H NMR (400 MHz, CD$_3$OD): δ ppm 2.17 (3H, s), 5.33 (2H, s), 6.84-6.86 (3H, m), 7.02 (2H, d, J=8.8 Hz), 7.94 (1H, d, J=6.4 Hz), 8.50 (1H, d, J=6.0 Hz). LCMS (mobile phase: 0-60% Acetonitrile-Water-0.02% NH$_4$Ac): purity is >95%, Rt=4.234 min. [M+H] Calc'd for C$_{16}$H$_{14}$N$_2$O$_3$, 283; Found, 283.

Example 63: methyl-2-[(4-chlorophenoxy)methyl]-1H-pyrrolo[3,2-b]pyridine-7-carboxylate

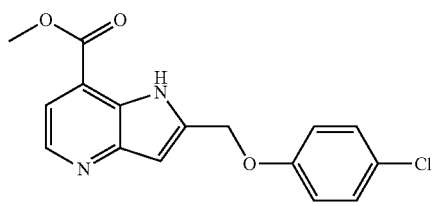 [SMILES: COC(=O)c1ccnc2cc(COc3ccc(Cl)cc3)[nH]c12]

The title compound was prepared in <1% yield using 1-chloro-4-(prop-2-yn-1-yloxy)-benzene according to the procedure for the preparation of Example 9. $^1$H NMR (400 MHz, CD$_3$OD): δ ppm 4.09 (3H, s), 5.37 (2H, s), 6.80 (1H, s), 7.07-7.09 (2H, s), 7.30-7.32 (2H, m), 7.75 (1H, d, J=4.8 Hz), 8.47 (1H, d, J=5.2 Hz). [M+H] Calc'd for C$_{16}$H$_{13}$ClN$_2$O$_3$, 317; Found, 317.

Example 64: 2-[(4-chlorophenoxy)methyl]-1H-pyrrolo[3,2-b]pyridine-7-carboxylic acid

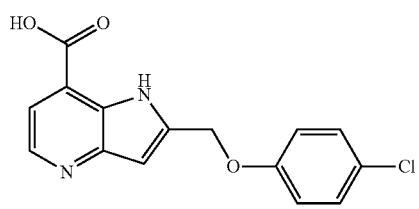 [SMILES: O=C(O)c1ccnc2cc(COc3ccc(Cl)cc3)[nH]c12]

The title compound was prepared in 75% yield using methyl-2-[(4-chlorophenoxy)methyl]-1H-pyrrolo[3,2-b]pyridine-7-carboxylate according to the procedure for the preparation of Example 5. $^1$H NMR (400 MHz, CD$_3$OD): δ ppm 5.32 (2H, s), 6.79 (1H, s), 6.96 (2H, d, J=8.8 Hz), 7.20 (2H, d, J=9.2 Hz), 7.84 (1H, d, J=5.6 Hz), 8.45 (1H, br).

LCMS (mobile phase: 0-60% Acetonitrile-Water-0.02% NH$_4$Ac): purity is >95%, Rt=4.345 min. [M+H] Calc'd for C$_{15}$H$_{11}$ClN$_2$O$_3$, 303; Found, 303.

Example 65: methyl 2-[(2-methylphenoxy)methyl]-1H-pyrrolo[3,2-b]-pyridine-7-carboxylate

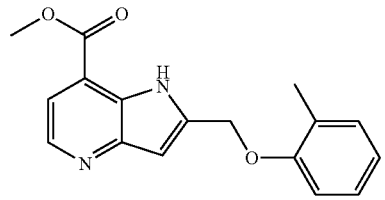 [SMILES: COC(=O)c1ccnc2cc(COc3ccccc3C)[nH]c12]

The title compound was prepared in 2% yield using 1-methyl-2-(prop-2-yn-1-yloxy)-benzene according to the procedure for the preparation of Example 9. $^1$H NMR (400 MHz, DMSO-d$_6$): δ ppm 2.19 (3H, s), 3.99 (3H, s), 5.34 (2H, s), 6.77 (1H, s), 6.86-6.88 (1H, m), 7.08 (1H, d, J=8.4 Hz), 7.16-7.18 (2H, m), 7.59 (1H, d, J=5.2 Hz), 8.48 (1H, d, J=4.8 Hz), 11.56 (1H, s). LCMS (mobile phase: 20-95% Acetonitrile-Water-0.02% NH$_4$Ac): purity is >95%, Rt=3.742 min. [M+H] calc'd for C$_{17}$H$_{16}$N$_2$O$_3$, 297; found 297.

Example 66: 2-[(2-methylphenoxy)methyl]-1H-pyrrolo[3,2-b]pyridine-7-carboxylic Acid

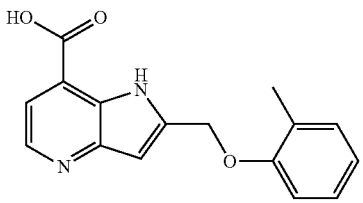 [SMILES: Cc1ccccc1OCc1cc2nccc(C(=O)O)c2[nH]1]

The title compound was prepared in 91% yield using methyl 2-[(2-methylphenoxy)-methyl]-1H-pyrrolo[3,2-b]pyridine-7-carboxylate according to the procedure for the preparation of Example 5. $^1$H NMR (400 MHz, DMSO-d$_6$): δ ppm 2.21 (3H, s), 5.41 (2H, s), 6.84-6.90 (2H, m), 7.05 (1H, d, J=8.4 Hz), 7.17-7.20 (2H, m), 7.75 (1H, d, J=5.6 Hz), 8.59 (1H, d, J=5.2 Hz), 12.08 (1H, s). LCMS (mobile phase: 0-60% Acetonitrile-Water-0.02% NH$_4$Ac): purity is >95%, Rt=4.218 min. [M+H] Calc'd for C$_{16}$H$_{14}$N$_2$O$_3$, 283; Found, 283.

Example 67: methyl 2-[[4-(trifluoromethyl)phenoxy]methyl]-1H-pyrrolo[3,2-b]-pyridine-7-carboxylate

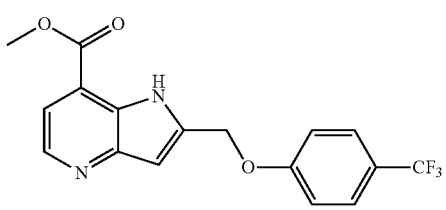 [SMILES: COC(=O)c1ccnc2cc(COc3ccc(C(F)(F)F)cc3)[nH]c12]

The title compound was prepared in 2% yield using 1-(prop-2-yn-1-yloxy)-4-trifluoro-methylbenzene according to the procedure for the preparation of Example 9. $^1$H NMR (400 MHz, DMSO-d$_6$): δ ppm 3.99 (3H, s), 5.43 (2H, s), 6.83 (1H, d, J=1.2 Hz), 7.27 (2H, d, J=8.4 Hz), 7.60 (1H, d, J=4.8 Hz), 7.70 (2H, d, J=8.8 Hz), 8.50 (1H, d, J=4.8 Hz), 11.63 (1H, s). LCMS (mobile phase: 20-95% Acetonitrile-Water-0.02% NH$_4$Ac): purity is >95%, Rt=3.876 min. [M+H] calc'd for C$_{17}$H$_{13}$N$_2$O$_3$F$_3$, 351; found 351.

Example 68: 2-[[4-(trifluoromethyl)phenoxy]methyl]-1H-pyrrolo[3,2-b]-pyridine-7-carboxylic Acid

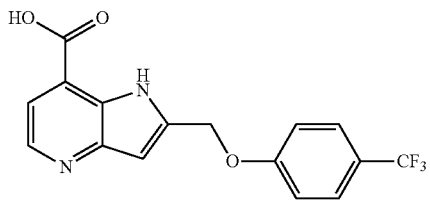 [SMILES: O=C(O)c1ccnc2cc(COc3ccc(C(F)(F)F)cc3)[nH]c12]

The title compound was prepared in 85% yield using methyl 2-[[4-(trifluoromethyl)-phenoxy]methyl]-1H-pyrrolo[3,2-b]pyridine-7-carboxylate according to the procedure for the preparation of Example 5. $^1$H NMR (400 MHz, DMSO-d$_6$): δ ppm 5.43 (2H, s), 6.79 (1H, s), 7.25 (2H, d, J=8.8 Hz), 7.58 (1H, d, J=4.8 Hz), 7.69 (2H, d, J=8.8 Hz), 8.48 (1H, d, J=4.0 Hz), 11.62 (1H, s), 13.82 (1H, br). LCMS (mobile phase: 0-60% Acetonitrile-Water-0.02% NH$_4$Ac): purity is >95%, Rt=4.575 min. [M+H] calc'd for C$_{16}$H$_{11}$N$_2$O$_3$F$_3$, 337; found 337.

Example 69: methyl 2-(2-phenylethyl)-1H-pyrrolo[3,2-b]pyridine-7-carboxylate

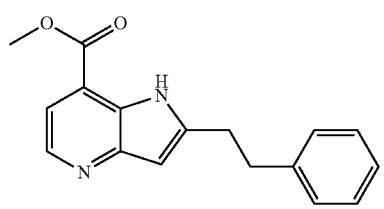 [SMILES: COC(=O)c1ccnc2cc(CCc3ccccc3)[nH]c12]

The title compound was prepared in 33% yield using 4-phenyl-1-butyne according to the procedure for the preparation of Example 4. $^1$H NMR (400 MHz, CDCl$_3$): δ ppm 3.07-3.14 (m, 2H) 3.16-3.25 (m, 2H) 4.00 (s, 3H) 6.62 (br. s., 1H) 7.21-7.25 (m, 2H) 7.28-7.39 (m, 3H) 7.59 (br. s., 1H) 8.49 (br. s., 1H) 9.23 (br. s., 1H). [M+H] calc'd for C$_{17}$H$_{16}$N$_2$O$_2$, 281; found 281.

Example 70: 2-(2-phenylethyl)-1H-pyrrolo[3,2-b]pyridine-7-carboxylic Acid

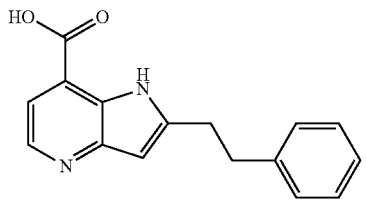 [SMILES: O=C(O)c1ccnc2cc(CCc3ccccc3)[nH]c12]

The title compound was prepared in 85% yield using methyl 2-(2-phenylethyl)-1H-pyrrolo[3,2-b]pyridine-7-carboxylate according to the procedure for the preparation of Example 5. $^1$H NMR (400 MHz, DMSO-d$_6$): δ ppm 3.00-3.08 (m, 2H) 3.11-3.20 (m, 2H) 6.41-6.45 (m, 1H) 7.16-7.23 (m, 1H) 7.26-7.34 (m, 5H) 7.45 (d, J=5.05 Hz, 2H) 8.36 (d, J=5.05 Hz, 1H) 11.21 (br. s., 1H) 13.62 (br. s., 1H). [M+H] calc'd for C$_{16}$H$_{14}$N$_2$O$_2$, 267; found 267.

Example 71: (±)-methyl 2-[(2-chlorophenyl)-hydroxymethyl]-1H-pyrrolo[3,2-b]-pyridine-7-carboxylate

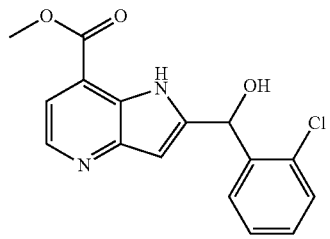 [SMILES: COC(=O)c1ccnc2cc(C(O)c3ccccc3Cl)[nH]c12]

The title compound was prepared in 33% yield using (±)-1-(2-chlorophenyl)-prop-2-yn-1-ol according to the procedure for the preparation of Example 4. $^1$H NMR (400 MHz, CDCl$_3$): δ ppm 4.04 (s, 3H), 6.53 (s, 1H), 6.58-6.65 (m, 1H), 7.29-7.36 (m, 2H), 7.41 (d, J=2.02 Hz, 1H), 7.61 (d, J=7.33 Hz, 1H), 7.64 (d, J=5.05 Hz, 1H), 8.51 (d, J=4.80 Hz, 1H), 9.84 (br. s., 1H). [M+H] calc'd for C$_{16}$H$_{13}$N$_2$O$_3$Cl, 317; found 317.

Example 72: (±)-2-[(2-chlorophenyl)-hydroxymethyl]-1H-pyrrolo[3,2-b]-pyridine-7-carboxylic Acid

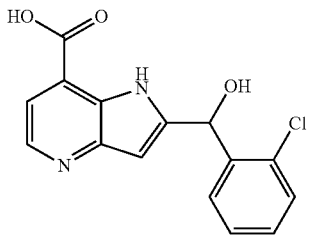

The title compound was prepared in 88% yield using (±)-methyl 2-[(2-chlorophenyl)-hydroxymethyl]-1H-pyrrolo[3,2-b]pyridine-7-carboxylate according to the procedure for the preparation of Example 5. $^1$H NMR (400 MHz, DMSO-d$_6$): δ ppm 6.12 (d, J=1.52 Hz, 1H), 6.30-6.40 (m, 2H), 7.33-7.45 (m, 2H), 7.45-7.49 (m, 1H), 7.53 (d, J=4.80 Hz, 1H), 7.63 (dd, J=7.58, 1.77 Hz, 1H), 8.42 (d, J=5.05 Hz, 1H), 11.09 (br. s., 1H), 13.80 (br. s., 1H). [M+H] calc'd for C$_{15}$H$_{11}$N$_2$O$_3$Cl, 303; found 303.

Example 73: methyl 2-[(3-methylphenoxy)methyl]-1H-pyrrolo[3,2-b]-pyridine-7-carboxylate

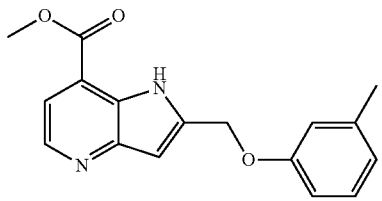

The title compound was prepared in <1% yield using 3-fluoro-4-(prop-2-yn-1-yloxy)-benzene according to the procedure for the preparation of Example 9. $^1$H NMR (400 MHz, DMSO-d$_6$): δ 2.19 (3H, s), 3.99 (3H, s), 5.34 (2H, s), 6.77 (1H, s), 6.86-6.88 (1H, m), 7.08 (1H, d, J=8.4 Hz), 7.16-7.18 (2H, m), 7.59 (1H, d, J=5.2 Hz), 8.48 (1H, d, J=4.8 Hz), 11.56 (1H, s). LCMS (mobile phase: 20-95% Acetonitrile-Water-0.02% NH$_4$Ac): purity is >95%, Rt=3.491 min. [M+H] Calc'd for C$_{17}$H$_{16}$N$_2$O$_3$, 297; Found, 297.

Example 74: 2-[(3-methylphenoxy)methyl]-1H-pyrrolo[3,2-b]pyridine-7-carboxylic Acid

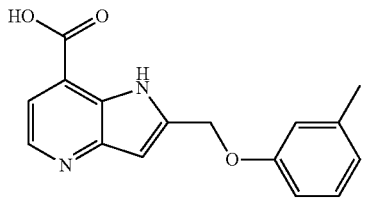 [SMILES: Cc1cccc(OCc2cc3nccc(C(=O)O)c3[nH]2)c1]

The title compound was prepared in 88% yield using methyl 2-[(3-methylphenoxy)-methyl]-1H-pyrrolo[3,2-b]pyridine-7-carboxylate according to the procedure for the preparation of Example 5. $^1$H NMR (400 MHz, DMSO-d$_6$): δ ppm 2.29 (3H, s), 5.36 (2H, s), 6.78-6.88 (4H, m), 7.17-7.22 (1H, m), 7.73 (1H, d, J=7.2 Hz), 8.58 (1H, d, J=7.2 Hz), 12.02 (1H, s). LCMS (mobile phase: 0-60% Acetonitrile-Water-0.02% NH$_4$Ac): purity is >95%, Rt=3.491 min. [M+H] Calc'd for C$_{16}$H$_{14}$N$_2$O$_3$, 283; Found, 283.

Example 75: methyl-2-(2,3dihydro-1-benzofuran-5-yloxymethyl)-1H-pyrrolo[3,2-b]pyridine-7-carboxylate

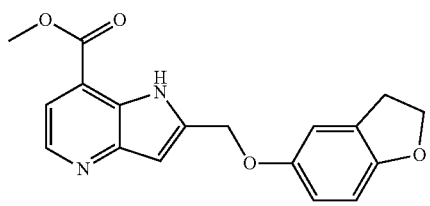 [SMILES: COC(=O)c1ccnc2cc(COc3ccc4c(c3)CCO4)[nH]c12]

A mixture containing 2,3-dihydrobenzofuran-5-ol (3.12 mg, 23 mmol), 3-bromo-propyne (3.3 g, 28 mmol), and K$_2$CO$_3$ (6.4 g, 46 mmol) in acetone (30 mL) was purged with nitrogen and stirred at 60° C. overnight. The reaction was concentrated in vacuo and the residue suspended in dichloromethane and filtered. The filtrate was concentrated in vacuo and the residue purified by silica gel chromatograph (PE/EA=50/1~20/1) to afford 5-(prop-2-yn-1-yloxy)-2,3-dihydrobenzofuran (3.48 g, 86%) as a yellow oil.

The title compound was prepared in <1% yield using 5-(prop-2-yn-1-yloxy)-2,3-dihydro-benzofuran according to the procedure for the preparation of Example 9. $^1$H NMR (400 MHz, DMSO-d$_6$): δ ppm 3.15 (2H, t, J=8.8 Hz), 3.99 (3H, s), 4.47 (2H, t, J=8.8 Hz), 5.24 (2H, s), 6.67 (1H, d, J=8.4 Hz), 6.74-6.79 (2H, m), 6.98 (1H, d, J=2.8 Hz), 7.58 (1H, d, J=4.8 Hz), 8.48 (1H, d, J=5.2 Hz), 11.53 (1H, s). LCMS (mobile phase: 20-95% Acetonitrile-Water-0.02% NH$_4$Ac): purity is >95%, Rt=3.105 min. [M+H] Calc'd for C$_{18}$H$_{16}$N$_2$O$_4$, 325; Found, 325.

Example 76: 2-(2,3dihydro-1-benzofuran-5-yloxymethyl)-1H-pyrrolo[3,2-b]-pyridine-7-carboxylic Acid

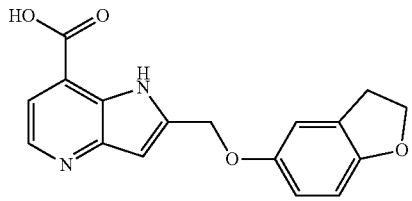 [SMILES: O=C(O)c1ccnc2cc(COc3ccc4c(c3)CCO4)[nH]c12]

The title compound was prepared in 88% yield using methyl-2-(2,3dihydro-1-benzofuran-5-yloxymethyl)-1H-pyrrolo[3,2-b]pyridine-7-carboxylate according to the procedure for the preparation of Example 5. $^1$H NMR (400 MHz, DMSO-d$_6$): δ ppm 3.15 (2H, t, J=8.4 Hz), 4.47 (2H, t, J=8.4 Hz), 5.31 (2H, s), 6.68 (1H, d, J=8.4 Hz), 6.75-6.81 (2H, m), 6.98 (1H, d, J=2.4 Hz), 7.74 (1H, d, J=5.2 Hz), 8.59 (1H, d, J=5.6 Hz), 12.04 (1H, s). [M+H] Calc'd for C$_{17}$H$_{14}$N$_2$O$_4$, 311; Found, 311.

Example 77: methyl 2-[(2-chlorophenyl)methyl]-1H-pyrrolo[3,2-b]-pyridine-7-carboxylate

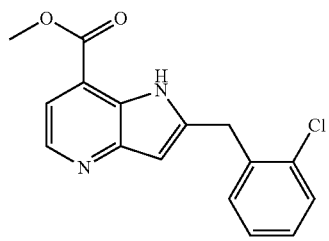 [SMILES: COC(=O)c1ccnc2cc(Cc3ccccc3Cl)[nH]c12]

The title compound was prepared in 74% yield using methyl 2-[(2-chlorophenyl)-hydroxymethyl]-1H-pyrrolo[3,2-b]pyridine-7-carboxylate according to the procedure for the preparation of Example 34. $^1$H NMR (400 MHz, CDCl$_3$): δ ppm 4.11 (s, 3H), 4.42 (s, 2H), 7.00 (s, 1H), 7.28-7.38 (m, 3H), 7.45-7.51 (m, 1H), 7.89 (d, J=6.06 Hz, 1H), 8.62 (d, J=5.81 Hz, 1H), 10.14 (br. s., 1H). [M+H] Calc'd for C$_{16}$H$_{13}$ClN$_2$O$_2$, 301; Found, 301.

Example 78: 2-[(2-chlorophenyl)methyl]-1H-pyrrolo[3,2-b]pyridine-7-carboxylic Acid

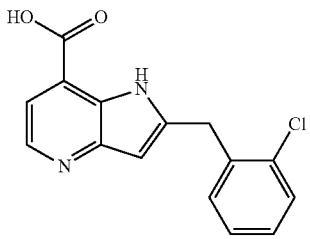 [SMILES: O=C(O)c1ccnc2cc(Cc3ccccc3Cl)[nH]c12]

The title compound was prepared in 88% yield using methyl 2-[(2-chlorophenyl)methyl]-1H-pyrrolo[3,2-b]pyridine-7-carboxylate according to the procedure for the preparation of Example 5. $^1$H NMR (400 MHz, DMSO-d$_6$): δ ppm 4.28 (s, 2H), 6.14 (s, 1H), 7.22-7.33 (m, 3H), 7.35-7.51 (m, 2H), 8.32 (d, J=5.05 Hz, 1H), 11.32 (br. s., 1H), 13.66 (br. s., 1H). [M+H] Calc'd for C$_{15}$H$_{11}$ClN$_2$O$_2$, 287; Found, 287.

Example 79: 2-[(3-fluorophenoxy)methyl]-1H-pyrrolo[3,2-b]pyridine-7-carboxylic Acid

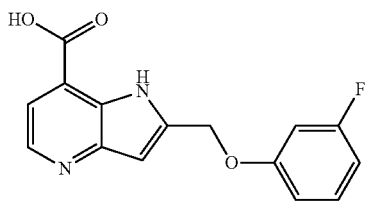

The title compound was prepared in <1% yield using 1-fluoro-3-(prop-2-yn-1-yloxy)-benzene according to the procedure for the preparation of Examples 9 and 5. $^1$H NMR (400 MHz, DMSO-d$_6$): δ ppm 5.40 (2H, s), 6.79-6.84 (1H, m), 6.89-6.99 (3H, m), 7.33-7.39 (1H, m), 7.76 (1H, d, J=4.8 Hz), 8.61 (1H, br), 12.11 (1H, s). LCMS (mobile phase: 5-95% Acetonitrile-Water-0.02% NH$_4$Ac): purity is >95%, Rt=3.321 min. [M+H] Calc'd for C$_{15}$H$_{11}$FN$_2$O$_3$, 287; Found, 287.

Example 80: 2-[(3-chlorophenoxy)methyl]-1H-pyrrolo[3,2-b]pyridine-7-carboxylic Acid

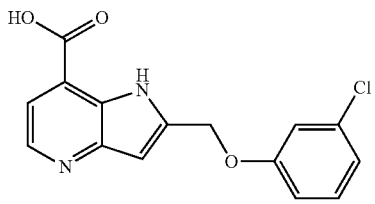 [SMILES: O=C(O)c1ccnc2cc(COc3cccc(Cl)c3)[nH]c12]

The title compound was prepared in <1% yield using 1-chloro-3-(prop-2-yn-1-yloxy)-benzene according to the procedure for the preparation of Examples 9 and 5. $^1$H NMR (400 MHz, DMSO-d$_6$): δ ppm 5.42 (2H, s), 6.90 (1H, s), 7.05 (2H, d, J=8.8 Hz), 7.18-7.19 (1H, m), 7.35 (1H, t, J=8.4 Hz), 7.79 (1H, d, J=5.2 Hz), 8.61-8.63 (1H, m), 12.18 (1H, s). LCMS (mobile phase: 5%-95% Acetonitrile-Water-0.02% NH$_4$Ac): purity is >95%, Rt=3.432 min. [M+H] Calc'd for C$_{15}$H$_{11}$ClN$_2$O$_3$, 303; Found, 303.

Example 81: 2-[(3,5-difluorophenoxy)methyl]-1H-pyrrolo[3,2-b]pyridine-7-carboxylic Acid

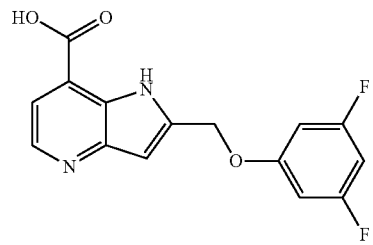 [SMILES: O=C(O)c1ccnc2cc(COc3cc(F)cc(F)c3)[nH]c12]

The title compound was prepared in <1% yield using 1,3-difluoro-5-(prop-2-yn-1-yloxy)-benzene according to the procedure for the preparation of Examples 9 and 5. $^1$H NMR (400 MHz, DMSO-d$_6$): δ ppm 5.40 (2H, s), 6.82-6.90 (4H, m), 7.75 (1H, d, J=5.2 Hz), 8.60 (1H, d, J=5.2 Hz), 12.07 (1H, s). LCMS (mobile phase: 5-95% Acetonitrile-Water-0.02% NH$_4$Ac): purity is >95%, Rt=3.385 min. [M+H] Calc'd for C$_{15}$H$_{10}$F$_2$N$_2$O$_3$, 305; Found, 305.

Example 82: 2-[(3,5-dimethylphenoxy)methyl]-1H-pyrrolo[3,2-b]pyridine-7-carboxylic Acid

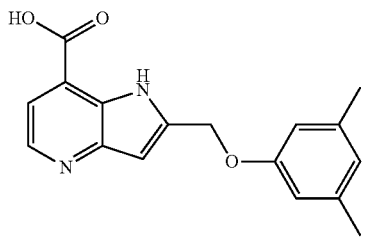 [SMILES: Cc1cc(C)cc(OCc2cc3nccc(C(=O)O)c3[nH]2)c1]

The title compound was prepared in <1% yield using 1,3-dimethyl-5-(prop-2-yn-1-yl-oxy)benzene according to the procedure for the preparation of Examples 9 and 5. $^1$H NMR (400 MHz, DMSO-d$_6$): δ ppm 2.24 (6H, s), 5.35 (2H, s), 6.62 (1H, s), 6.68 (2H, s), 8.83 (1H, d, J=2.0 Hz), 7.75 (1H, d, J=5.2 Hz), 8.59 (1H, d, J=5.6 Hz), 12.06 (1H, s). LCMS (mobile phase: 5-95% Acetonitrile-Water-0.02% NH$_4$Ac): purity is >95%, Rt=3.490 min. [M+H] Calc'd for C$_{16}$H$_{16}$N$_2$O$_3$, 297; Found, 297.

Example 83: 2-[(3,5-dichlorophenoxy)methyl]-1H-pyrrolo[3,2-b]pyridine-7-carboxylic Acid

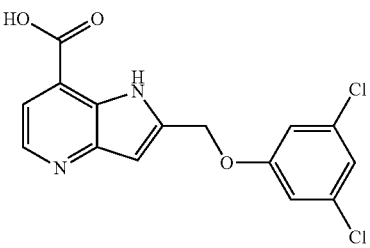 [SMILES: O=C(O)c1ccnc2cc(COc3cc(Cl)cc(Cl)c3)[nH]c12]

The title compound was prepared in <1% yield using 1,3-dichloro-5-(prop-2-yn-1-yloxy)-benzene according to the procedure for the preparation of Examples 9 and 5. ¹H NMR (400 MHz, DMSO-d$_6$): δ ppm 5.37 (2H, s), 6.79 (1H, s), 7.19 (3H, s), 7.59 (1H, s), 8.59 (1H, s, br), 11.59 (1H, s), 13.80 (1H, s). LCMS (mobile phase: 5-95% Acetonitrile-Water-0.02% NH$_4$Ac): purity is >95%, Rt=3.490 min. [M+H] Calc'd for C$_{15}$H$_{10}$Cl$_2$N$_2$O$_3$, 337; Found, 337.

Example 84: (±)-2-(1-phenoxyethyl)-1H-pyrrolo[3,2-b]pyridine-7-carboxylic Acid

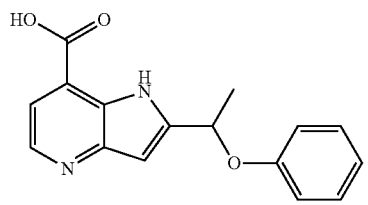 [SMILES: CC(Oc1ccccc1)c1cc2nccc(C(=O)O)c2[nH]1]

To a mixture containing (±)-3-butyn-2-ol (2.02 g, 29 mmol), TsCl (6.8 g, 36 mmol) in Et$_2$O (30 mL) was added KOH (10.0 g, 174 mmol) at 0° C. The mixture was stirred at 0° C. for 1.5 hr and filtered. The filtrate was concentrated in vacuo to afford (±)-(but-3-yn-2-yl)-4-methylphenylsulfonate (2.03 g, 31%) as a yellow oil. ¹H NMR (400 MHz, CDCl$_3$): δ ppm 1.57 (3H, d, J=6.8 Hz), 2.41-2.42 (1H, m), 2.45 (3H, s), 5.14-4.19 (1H, m), 7.34 (2H, d, J=8.0 Hz), 7.82 (2H, d, J=8.4 Hz).

To a mixture containing phenol (1.0 g, 10 mmol) and KOH (0.6 g, 10 mmol) in 95% EtOH (20 mL) was added (±)-(but-3-yn-2-yl)-4-methylphenylsulfonate (2.0 g, 9 mmol) at 0° C. The mixture was heated at 65° C. overnight. H$_2$O was added and the mixture was extracted with Et$_2$O. The organic layers were concentrated and purified by silica gel chromatography (PE/EA=10/1) to afford (±)-(but-3-yn-2-yloxy)benzene (690 mg, 50%). ¹H NMR (400 MHz, CDCl$_3$): δ ppm 1.66 (3H, d, J=6.4 Hz), 2.46 (1H, d, J=1.6 Hz), 4.85-4.90 (1H, m), 6.96-7.02 (3H, m), 7.25-7.32 (2H, m).

The title compound was prepared in 10% yield using (±)-(but-3-yn-2-yloxy)benzene according to the procedure for the preparation of Examples 9 and 5. ¹H NMR (400 MHz, DMSO-d$_6$): δ ppm 1.69 (3H, d, J=6.4 Hz), 5.84-5.89 (1H, m), 6.59 (1H, s), 6.87-6.97 (3H, m), 7.21-7.26 (2H, m), 7.54 (1H, d, J=4.8 Hz), 8.41-8.45 (1H, m), 11.48 (1H, s), 13.85 (1H, bs). LCMS (mobile phase: 5-95% Acetonitrile-Water-0.02% NH$_4$Ac): purity is >95%, Rt=3.266 min.

Example 85: (±)-2-(1-phenoxybutyl)-1H-pyrrolo[3,2-b]pyridine-7-carboxylic Acid

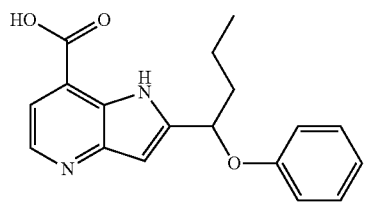 [SMILES: CCCC(Oc1ccccc1)c1cc2nccc(C(=O)O)c2[nH]1]

The title compound was prepared in <1% yield using (±)-1-hexyn-3-ol according to the procedure for the preparation of Example 84. ¹H NMR (400 MHz, DMSO-d$_6$): δ ppm 0.94 (3H, t, J=6.4 Hz), 1.38-1.54 (2H, m), 1.93-2.05 (2H, m), 5.71-5.74 (1H, m), 6.54 (1H, s), 6.85-6.96 (3H, m), 7.20-7.24 (2H, m), 7.53 (1H, s), 8.48-8.52 (1H, m), 11.45 (1H, s), 13.80 (1H, bs). LCMS (mobile phase: 5%-95% Acetonitrile-Water-0.02% NH$_4$Ac): purity is >95%, Rt=3.597 min. [M+H] Calc'd for C$_{18}$H$_{18}$N$_2$O$_3$, 311; Found, 311.

Example 86: (±)-2-(3-methyl-phenoxybutyl)-1H-pyrrolo[3,2-b]pyridine-7-carboxylic Acid

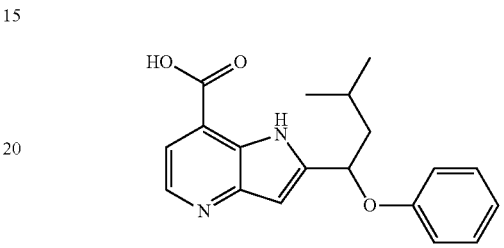

The title compound was prepared in <1% yield starting from (±)-5-methlyl-1-hexyn-3-ol according to the procedure for the preparation of Example 84. ¹H NMR (400 MHz, DMSO-d$_6$): δ ppm 0.95-0.99 (6H, m), 1.76-1.86 (2H, m), 1.97-2.052 (1H, m), 5.78-5.81 (1H, m), 6.57 (1H, s), 6.85-6.88 (1H, m), 6.97 (2H, d, J=8.0 Hz), 7.20-7.24 (2H, m), 7.52 (1H, d, J=4.0 Hz), 8.39-8.43 (1H, m). LCMS (mobile phase: 5-95% Acetonitrile-Water-0.02% NH$_4$Ac): purity is >95%, Rt=3.679 min. [M+H] Calc'd for C$_{19}$H$_{20}$N$_2$O$_3$, 325; Found, 325.

Example 87: (±)-methyl 2-[(2-chlorophenyl)propoxymethyl])-1H-pyrrolo[3,2-b]-pyridine-7-carboxylate

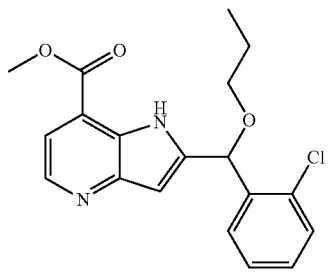 [SMILES: CCCOC(c1cc2nccc(C(=O)OC)c2[nH]1)c1ccccc1Cl]

To a round-bottom flask charged with (±)-1-(2-chlorophenyl)-prop-2-yn-1-ol (1.165 g, 7 mmol) in DMF was added NaH (336 mg, 8.4 mmol, 60% mineral oil suspension) portion-wise. The reaction was stirred for 30 min at ambient temp under N$_2$ atmosphere. 1-bromopropane was added dropwise at 0° C. and the reaction was allowed to warm to ambient temperature and stirred for 16 hr. The reaction was quenched with saturated NH$_4$Cl and extracted with EtOAc (2×). The combined organic layers were successively washed with water (2×), followed by brine, dried with Na$_2$SO$_4$ and concentrated in vacuo. The residue purified by silica gel chromatography (0%-5% gradient of EtOAc in hexanes) to afford (±)-1-(2-chlorophenyl)prop-2-yn-1-yl propyl ether (1.2 g, 82%) as a light yellow oil.

The title compound was prepared in 15% yield using (±)-1-(2-chlorophenyl)prop-2-yn-1-yl propyl ether according to the procedure for the preparation of Example 4. $^1$H NMR (400 MHz, CDCl$_3$): δ ppm 1.00 (t, J=7.45 Hz, 3H), 1.72 (dq, J=14.02, 6.95 Hz, 2H), 3.55 (t, J=6.57 Hz, 2H), 3.87-4.62 (m, 4H), 4.03 (s, 3H), 6.10 (s, 1H), 6.60 (br. s., 1H), 7.28-7.50 (m, 3H), 7.52-7.75 (m, 2H), 8.51 (br. s., 1H), 9.71 (br. s., 1H). [M+H] Calc'd for C$_{19}$H$_{19}$ClN$_2$O$_3$, 359; Found, 359.

Example 88: (±)-2-[(2-chlorophenyl)propoxymethyl])-1H-pyrrolo[3,2-b]-pyridine-7-carboxylic Acid

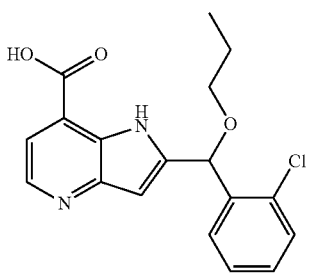

The title compound was prepared in 15% yield using (±)-methyl 2-[(2-chlorophenyl)-propoxymethyl])-1H-pyrrolo[3,2-b]pyridine-7-carboxylate according to the procedure for the preparation of Example 5. $^1$H NMR (400 MHz, DMSO-d$_6$): δ ppm 0.90 (t, J=7.33 Hz, 3H) 1.60 (m, 2H) 3.40-3.52 (m, 2H) 3.40-3.52 (m, 2H) 3.54-3.64 (m, 1H) 6.11-6.14 (m, 1H) 6.24 (d, J=2.02 Hz, 1H) 6.55-6.59 (m, 1H) 7.35-7.45 (m, 2H) 7.47-7.52 (m, 2H) 7.54 (d, J=5.05 Hz, 1H) 8.44 (d, J=4.80 Hz, 1H) 11.33 (br. s., 1H) 13.76 (br. s., 1H). [M+H] Calc'd for C$_{18}$H$_{17}$ClN$_2$O$_3$, 345; Found, 345.

Example 89: methyl 2-[(2,4-dichlorophenyl) methyl]-1H-pyrrolo[3,2-b]-pyridine-7-carboxylate

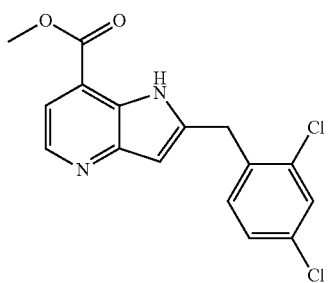 [SMILES: COC(=O)c1ccnc2cc(Cc3ccc(Cl)cc3Cl)[nH]c12]

The title compound was prepared in 10% yield using 2,4-dichloro-1-(prop-2-yn-1-yl)-benzene according to the procedure for the preparation of Example 55. $^1$H NMR (400 MHz, CDCl$_3$): δ ppm 4.02 (s, 3H), 4.31 (s, 2H), 6.61 (s, 1H), 7.20-7.23 (m, 1H), 7.46 (d, J=1.77 Hz, 1H), 7.61 (d, J=5.05 Hz, 1H), 8.51 (d, J=5.31 Hz, 1H), 9.54 (br. s., 1H). [M-FH] Calc'd for C$_{16}$H$_{12}$Cl$_2$N$_2$O$_2$, 335; Found, 335.

Example 90: 2-[(2,4-dichlorophenyl)methyl]-1H-pyrrolo[3,2-b]pyridine-7-carboxylic Acid

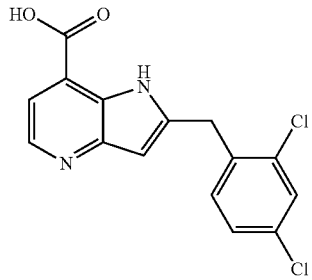 [SMILES: O=C(O)c1ccnc2cc(Cc3ccc(Cl)cc3Cl)[nH]c12]

The title compound was prepared in 88% yield using 5-methlyl-1-hexyn-3-ol according to the procedure for the preparation of Example 5. $^1$H NMR (400 MHz, DMSO-d$_6$) δ ppm 4.33 (s, 2H) 6.24 (s, 1H) 7.31-7.44 (m, 2H) 7.49 (d, J=5.31 Hz, 1H) 7.66 (s, 1H) 8.39 (d, J=4.55 Hz, 1H) 11.43 (br. s., 1H) 13.70 (br. s., 1H). [M+H] Calc'd for C$_{15}$H$_{10}$Cl$_2$N$_2$O$_2$, 321; Found, 321.

Example 91: methyl 2-(1-benzofuran-2-yl)-1H-pyrrolo[3,2-b]pyridine-7-carboxylate

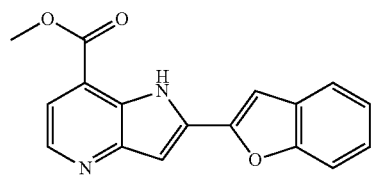 [SMILES: COC(=O)c1ccnc2cc(-c3cc4ccccc4o3)[nH]c12]

A mixture containing methyl 3-amino-2-chloroisonicotinate (372 mg, 2 mmol), 2-benzo-furanyl methyl ketone (960 mg, 6 mmol), MgSO$_4$ (120 mg, 1 mmol), and AcOH (150 μL, 3 mmol) in DMA was purged with N$_2$ for 10 min. Pd(tBu$_3$P)$_2$ (101 mg, 0.2 mmol) and K$_3$PO$_4$ (552 mg, 2.6 mmol) were added and the reaction sealed and heated at 140° C. for 16 hr. The reaction mixture was taken up in EtOAc and washed successively with water (2×), brine, and dried with N$_2$SO$_4$. The organic layers were concentrated in vacuo and the residue purified by column chromatography to afford the title compound (152 mg, 26%) as a yellow solid. $^1$H NMR (400 MHz, DMSO-d$_6$) δ ppm 4.33 (s, 2H), 6.24 (s, 1H), 7.31-7.44 (m, 2H), 7.49 (d, J=5.31 Hz, 1H), 7.66 (s, 1H), 8.39 (d, J=4.55 Hz, 1H), 11.43 (br. s., 1H), 13.70 (br. s., 1H). [M+H] Calc'd for C$_{17}$H$_{12}$N$_2$O$_3$, 293; Found, 293.

Example 92: 2-(1-benzofuran-2-yl)-1H-pyrrolo[3,2-b]pyridine-7-carboxylic Acid

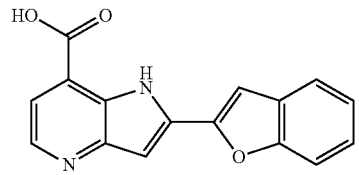 [SMILES: O=C(O)c1ccnc2cc(-c3cc4ccccc4o3)[nH]c12]

The title compound was prepared in 75% yield using 5-methlyl-1-hexyn-3-ol according to the procedure for the preparation of Example 5. ¹H NMR (400 MHz, DMSO-d₆) δ ppm 7.21 (s, 1H) 7.32 (d, J=7.58 Hz, 1H) 7.39 (s, 1H) 7.62 (d, J=4.80 Hz, 1H) 7.69 (d, J=8.08 Hz, 1H) 7.74 (d, J=7.58 Hz, 1H) 7.95 (s, 1H) 8.54 (d, J=5.05 Hz, 1H) 11.55 (br. s., 1H) 13.88 (br. s., 1H).

Example 93: 2-[(4-methoxyphenoxy)methyl]-1H-pyrrolo[3,2-b]pyridine-7-carboxylic Acid

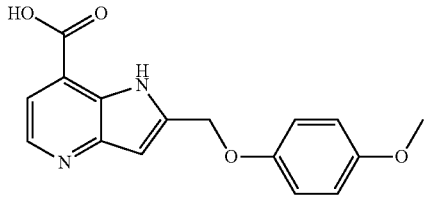

The title compound was prepared in <1% yield using 1-methoxy-4-(prop-2-yn-1-yloxy)-benzene according to the procedure for the preparation of Examples 9 and 5. ¹H NMR (400 MHz, DMSO-d₆): δ ppm 3.69 (3H, s), 5.27 (2H, s), 6.72 (1H, s), 6.87-6.90 (2H, m), 6.97-7.00 (2H, m), 7.56-7.57 (1H, m), 8.47-8.53 (1H, m), 11.53 (1H, s), 13.78 (1H, br s). LCMS (mobile phase: 5-95% Acetonitrile-Water-0.02% NH₄Ac): purity is >95%, Rt=3.137 min. [M+H] Calc'd for $C_{16}H_{14}N_2O_4$, 299; Found, 299.

Example 94: 2-[(2-chlorophenoxy)methyl]-1H-pyrrolo[3,2-b]pyridine-7-carboxylic Acid

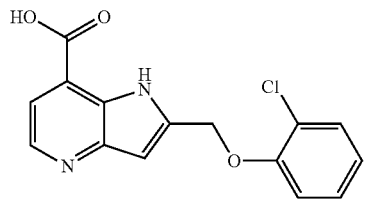 [SMILES: O=C(O)c1ccnc2cc(COc3ccccc3Cl)[nH]c12]

The title compound was prepared in <1% yield using 2-chloro-(prop-2-yn-1-yloxy)benzene according to the procedure for the preparation of Examples 9 and 5. ¹H NMR (400 MHz, CD₃OD): δ ppm 5.41 (2H, s), 6.84 (1H, s), 6.88-6.91 (1H, m), 7.11-7.13 (1H, m), 7.17-7.21 (1H, m), 7.31-7.33 (1H, m), 7.85 (1H, br s), 8.46 (1H, br s). LCMS (mobile phase: 5-95% Acetonitrile-Water-0.02% NH₄Ac): purity is >95%, Rt=3.372 min, [M+H] Calc'd for $C_{15}H_{11}ClN_2O_3$, 303; Found: 303.

Example 95: 2-[(2-fluorophenoxy)methyl]-1H-pyrrolo[3,2-b]pyridine-7-carboxylic Acid

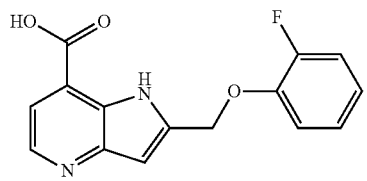 [SMILES: O=C(O)c1ccnc2cc(COc3ccccc3F)[nH]c12]

The title compound was prepared in <1% yield using 2-fluoro-(prop-2-yn-1-yloxy)-benzene according to the procedure for the preparation of Examples 9 and 5. ¹H NMR (400 MHz, DMSO-d₆): δ ppm 5.40 (2H, s), 6.78 (1H, s), 6.94-6.99 (1H, m), 7.14-7.21 (1H, m), 7.24-7.31 (1H, m), 7.33-7.35 (1H, m), 7.58-7.59 (1H, m), 8.47-8.49 (1H, m), 11.61 (1H, br), 13.61 (1H, br). LCMS (mobile phase: 5-95% Acetonitrile-Water-0.02% NH₄Ac): purity is >95%, Rt=3.300 min. [M+H] Calc'd for $C_{15}H_{11}FN_2O_3$, 287; Found, 287.

Example 96: 2-[(2-chloro-4-fluorophenoxy)methyl]-1H-pyrrolo[3,2-b]-pyridine-7-carboxylic Acid

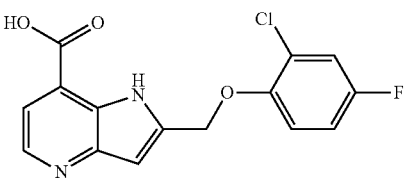

The title compound was prepared in <1% yield using 2-chloro-4-fluoro-(prop-2-yn-1-yl-oxy)benzene according to the procedure for the preparation of Examples 9 and 5. ¹H NMR (400 MHz, DMSO-d₆): δ ppm 5.39 (2H, s), 6.83 (1H, s), 6.94-6.99 (1H, m), 7.11-7.19 (2H, m), 7.84-7.86 (1H, m), 8.46 (1H, br). LCMS (mobile phase: 5-95% Acetonitrile-Water-0.02% NH₄Ac): purity is >95%, Rt=2.633 min. [M+H] Calc'd for $C_{15}H_{10}ClFN_2O_3$, 321; Found, 321.

Example 97: 2-{[4-(acetylamino)phenoxy]methyl}-1H-pyrrolo[3,2-b]pyridine-7-carboxylic Acid

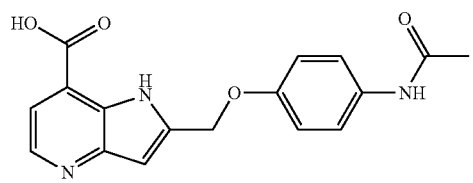 [SMILES: CC(=O)Nc1ccc(OCc2cc3nccc(C(=O)O)c3[nH]2)cc1]

The title compound was prepared in <1% yield using N-[4-(prop-2-yn-1-yl)phenyl]-acetamide according to the procedure for the preparation of Examples 9 and 5. ¹H NMR (400 MHz, DMSO-d₆): δ ppm 1.76 (3H, s), 5.32 (2H, s), 6.81 (1H, bs), 6.79 (1H, s), 6.82-6.85 (3H, m), 7.14 (1H, s), 7.28 (1H, d, J=10.0 Hz), 7.73-7.77 (2H, m), 7.81 (1H, br), 9.83 (1H, s), 11.96 (1H, br). LCMS (mobile phase: 5%-95% Acetonitrile-Water-0.02% NH₄Ac): purity is >95%, Rt=2.758 min. [M+H] Calc'd for $C_{17}H_{15}N_3O_4$, 326; Found, 326.

Example 98: 2-[(4-cyanophenoxy)methyl]-1H-pyrrolo[3,2-b]pyridine-7-carboxylic Acid

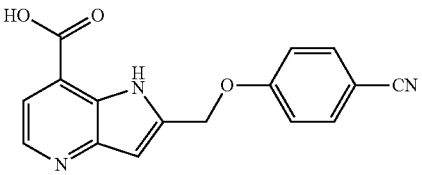 [SMILES: N#Cc1ccc(OCc2cc3nccc(C(=O)O)c3[nH]2)cc1]

The title compound was prepared in <1% yield using 4-(prop-2-yn-1-yl)benzo-nitrile according to the procedure for the preparation of Examples 9 and 5. $^1$H NMR (400 MHz, DMSO-d$_6$): δ ppm 5.42 (2H, s), 6.79 (1H, s), 7.24 (2H, d, J=9.2 Hz), 7.57-7.59 (1H, m), 7.83 (2H, d, J=6.8 Hz), 8.48 (1H, d, J=5.2 Hz), 11.62 (1H, s), 13.79 (1H, br). LCMS (mobile phase: 5%-95% Acetonitrile-Water-0.02% NH$_4$Ac): purity is >95%, Rt=2.432 min. [M+H] Calc'd for C$_{16}$H$_{11}$N$_3$O$_3$, 294; Found, 294.

Example 99: 2-(pyrrolidin-1-ylcarbonyl)-1H-pyrrolo[3,2-b]pyridine-7-carboxylic Acid

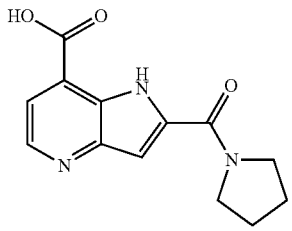

To a round-bottom flask charged with pyruvic acid (693 μL, 10 mmol), DMF (2 drops) in DCM (10 mL) was added SOCl$_2$ (730 μL, 20 mmol) dropwise at 0° C. The reaction was stirred at ambient temp for 30 min. Pyrrollidine (2.5 mL, 30 mmol) was added dropwise at 0° C. The reaction was allowed to stir for 1 hr at ambient temp. The reaction was taken up in DCM and the organic layers were successively washed with water, brine, dried with Na$_2$SO$_4$, and concentrated in vacuo. The residue was purified by column chromatography (0-30% gradient of EtOAc in Hexanes) to afford 1-(pyrrolidin-1-yl)propane-1,2-dione (335 mg, 24%).

The title compound was prepared in 34% yield using 1-(pyrrolidin-1-yl)propane-1,2-dione according to the procedure for the preparation of Example 91, except the product was purified by prep-HPLC (10-95% ACN/water, 0.1% HCO$_2$H). $^1$H NMR (400 MHz, DMSO-d$_6$): δ ppm 1.72-2.16 (m, 5H), 3.58 (t, J=6.82 Hz, 2H), 3.85 (t, J=6.69 Hz, 2H), 7.11-7.38 (m, 1H), 7.69 (d, J=4.80 Hz, 1H), 8.61 (d, J=4.80 Hz, 1H), 10.30-10.54 (m, 1H), 13.90-14.19 (m, 1H). [M+H] Calc'd for C$_{13}$H$_{13}$N$_3$O$_3$, 260; Found, 260.

Example 100: methyl 2-[(4-fluorophenyl)methyl]pyrrolo[3,2-b]pyridine-7-carboxylate

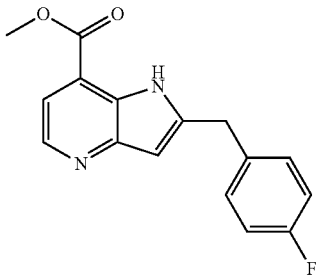 [SMILES: COC(=O)c1ccnc2cc(Cc3ccc(F)cc3)[nH]c12]

The title compound was prepared in <1% yield starting with 4-fluorobenzaldehyde according to the procedure for the preparation of Example 55 and 9. $^1$H NMR (400 MHz, CDCl$_3$): δ ppm 3.99 (3H, s), 4.17 (2H, s), 6.58 (1H, s), 7.03 (2H, t, J=8.4 Hz), 7.22-7.25 (2H, m), 7.56 (1H, d, J=4.0 Hz), 8.51-8.53 (1H, m), 9.24 (1H, bs). LCMS (mobile phase: 10%-95% Acetonitrile-Water-0.02% NH$_4$Ac): purity is >95%, Rt=3.573 min. [M+H] Calc'd for C$_{16}$H$_{13}$FN$_2$O$_2$, 285; Found, 285.

Example 101: 2-[(4-fluorophenyl)methyl]pyrrolo[3,2-b]pyridine-7-carboxylic Acid

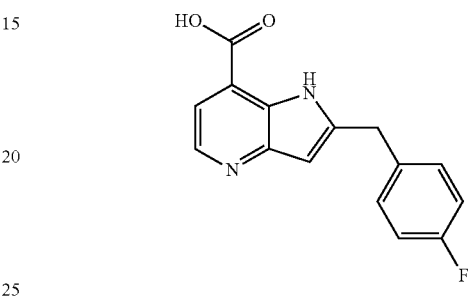

The title compound was prepared in 61% yield using methyl 2-[(4-fluorophenyl)-methyl]pyrrolo[3,2-b]pyridine-7-carboxylate according to the procedure for the preparation in Example 5. $^1$H NMR (400 MHz, DMSO-d$_6$): δ ppm 4.05 (2H, s), 6.36 (1H, s), 7.12-7.18 (2H, m), 7.36-7.51 (2H, m), 8.38 (1H, m), 11.33 (1H, s), 13.69 (1H, bs). LCMS (mobile phase: 5-95% Acetonitrile-Water-0.02% NH$_4$Ac): purity is >95%, Rt=3.250 min. [M+H] Calc'd for C$_{15}$H$_{11}$FN$_2$O$_2$, 271; Found, 271.

Example 102: methyl 2-[1-(4-fluorophenyl)-1-hydroxyethyl]-1H-pyrrolo[3,2-b]-pyridine-7-carboxylate

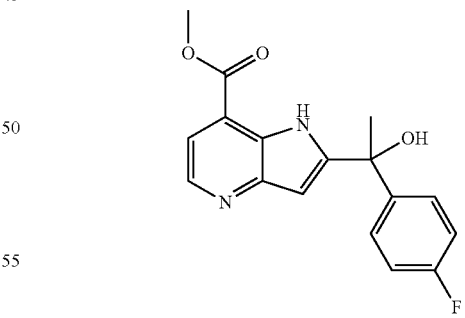

The title compound was prepared in 15% yield using 2-(4-fluorophenyl)-3-butyn-2-ol according to the procedure for the preparation of Example 4. $^1$H NMR (400 MHz, CDCl$_3$-d): δ ppm 2.08 (s, 3H), 4.02 (s, 3H), 6.81 (br. s., 1H), 7.03 (t, J=8.72 Hz, 2H), 7.46 (dd, J=8.72, 5.18 Hz, 2H), 7.68 (br. s., 1H), 8.52 (d, J=4.80 Hz, 1H), 9.73 (br. s., 1H). [M+H] Calc'd for C$_{17}$H$_{15}$FN$_2$O$_3$, 315; Found, 315.

Example 103: 2-[1-(4-fluorophenyl)-1-hydroxy-ethyl]-1H-pyrrolo[3,2-b]-pyridine-7-carboxylic Acid

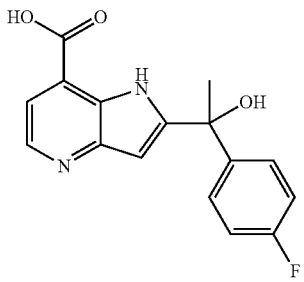

The title compound was prepared in 86% yield using methyl 2-[1-(4-fluorophenyl)-1-hydroxyethyl]-1H-pyrrolo[3,2-b]pyridine-7-carboxylate according to the procedure for the preparation in Example 5. $^1$H NMR (400 MHz, DMSO-d$_6$): δ ppm 1.89 (s, 3H), 6.41 (s, 1H), 6.67 (s, 1H), 7.14 (t, J=8.84 Hz, 2H), 7.45 (dd, J=8.84, 5.56 Hz, 2H), 7.51 (d, J=5.05 Hz, 1H), 8.45 (d, J=4.80 Hz, 1H), 10.29 (br. s., 1H), 13.81 (br. s., 1H). [M+H] Calc'd for $C_{16}H_{13}FN_2O_3$: 301; Found: 301.

Example 104: methyl 2-(1,2,3,4-tetrahydroquinolyl-carbonyl)pyrrolo[3,2-b]-pyridine-7-carboxylate

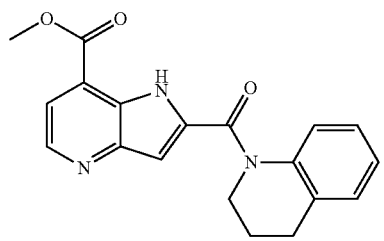 [SMILES: COC(=O)c1ccnc2cc(C(=O)N3CCCc4ccccc43)[nH]c12]

To a round-bottom flask charged with pyruvic acid (1.39 mL, 20 mmol), DMF (2 drops) in DCM (40 mL) was added SOCl$_2$ (1.46 mL, 20 mmol) dropwise at 0° C. The reaction was stirred at ambient temp for 30 min. DIEA (7.2 mL, 40 mmol) was added slowly at 0° C. followed by dropwise addition of 1,2,3,4-tetrahydroquinoline (2.66 g, 20 mmol). The reaction was allowed to stir for 1 hr at ambient temp. The reaction was taken up in DCM and the organic layers were successively washed with water, brine, dried with Na$_2$SO$_4$, and concentrated in vacuo. The residue was purified by column chromatography (0%-30% gradient of EtOAc in Hexanes) to afford 1-(3.4-dihydroquinolin-1-(2H)-yl)propane-1,2-dinone (480 mg, 30%).

The title compound was prepared in 10% yield using 1-(3.4-dihydroquinolin-1-(2H)-yl)-propane-1,2-dinone according to the procedure for the preparation of Example 91, except the product was purified by prep-HPLC (20-80% ACN/water, 0.1% NH$_4$Ac). $^1$H NMR (400 MHz, CDCl$_3$): δ ppm 2.06-2.13 (2H, m), 2.83-2.86 (2H, m), 4.01-4.05 (2H, m), 4.07 (3H, s), 6.44 (1H, s), 7.02-7.26 (3H, m), 7.26-7.27 (1H, m), 7.78 (1H, d, J=4.4 Hz), 8.59 (1H, d, J=4.8 Hz), 10.02 (1H, bs). LCMS (mobile phase: 20%-95% Acetonitrile-Water-0.02% NH$_4$Ac): purity is >95%, Rt=3.363 min. [M+H] Calc'd for $C_{19}H_{17}N_3O_3$, 336; Found, 336.

Example 105: 2-(1,2,3,4-tetrahydroquinolylcarbonyl)pyrrolo[3,2-b]-pyridine-7-carboxylic Acid

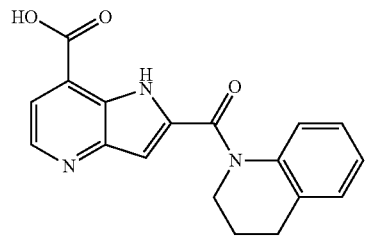 [SMILES: O=C(O)c1ccnc2cc(C(=O)N3CCCc4ccccc43)[nH]c12]

The title compound was prepared in 65% yield methyl 2-(1,2,3,4-tetrahydroquinolyl-carbonyl)pyrrolo[3,2-b]pyridine-7-carboxylate according to the procedure for the preparation in Example 5. $^1$H NMR (400 MHz, DMSO-d$_6$): δ ppm 1.95-2.01 (2H, m), 2.81-2.85 (2H, m), 3.84-3.88 (2H, m), 6.52 (1H, s), 6.97-7.10 (2H, m), 7.19-7.28 (2H, m), 7.63 (1H, d, J=4.4 Hz), 8.52 (1H, d, J=4.8 Hz), 11.11 (1H, bs), 13.93 (1H, bs). LCMS (mobile phase: 20%-95% Acetonitrile-Water-0.02% NH4Ac): purity is >95%, Rt=3.148 min. [M+H] Calc'd for $C_{18}H_{15}N_3O_3$, 322; Found, 322.

Example 106: methyl 2-(indolinylcarbonyl)pyrrolo[3,2-b]pyridine-7-carboxylate

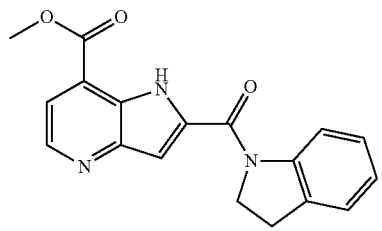 [SMILES: COC(=O)c1ccnc2cc(C(=O)N3CCc4ccccc43)[nH]c12]

The title compound was prepared in 2% yield starting with indoline according to the procedure for the preparation of Example 104. $^1$H NMR (400 MHz, DMSO-d$_6$): δ ppm 3.21-3.25 (2H, m), 4.01 (3H, s), 4.42-4.46 (2H, m), 7.09-7.13 (1H, m), 7.23-7.35 (2H, m), 7.74 (1H, d, J=4.4 Hz), 8.21-8.23 (1H, m), 8.64 (1H, d, J=4.8 Hz), 11.11 (1H, s). LCMS (mobile phase: 10%-95% Acetonitrile-Water-0.02% NH$_4$Ac): purity is >95%, Rt=2.741 min. [M+H] Calc'd for $C_{18}H_{15}N_3O_3$, 322; Found, 322.

Example 107: 2-(indolinylcarbonyl)pyrrolo[3,2-b]pyridine-7-carboxylic Acid

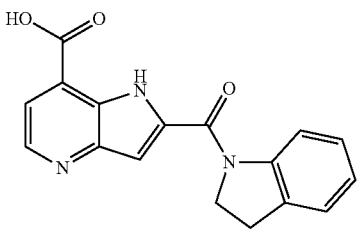 [SMILES: O=C(O)c1ccnc2cc(C(=O)N3CCc4ccccc43)[nH]c12]

The title compound was prepared in 40% yield methyl 2-(indolinylcarbonyl)pyrrolo[3,2-b]pyridine-7-carboxylate according to the procedure for the preparation in Example 5. ¹H NMR (400 MHz, DMSO-d₆): δ ppm 3.21-3.27 (2H, m), 4.48-4.51 (2H, m), 7.09-7.14 (1H, m), 7.25-7.29 (3H, m), 7.71 (1H, d, J=4.4 Hz), 8.16-8.23 (1H, m), 8.64 (1H, d, J=4.8 Hz), 10.80 (1H, s). LCMS (mobile phase: 5%-95% Acetonitrile-Water-0.02% NH₄Ac): purity is >95%, Rt=2.365 min. [M+H] Calc'd for $C_{17}H_{13}N_3O_3$, 308; Found, 308.

Example 108: methyl 2-(piperidylcarbonyl)pyrrolo[3,2-b]pyridine-7-carboxylate

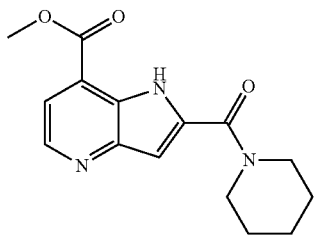 [SMILES: COC(=O)c1ccnc2cc(C(=O)N3CCCCC3)[nH]c12]

The title compound was prepared in 4% yield starting with piperidine according to the procedure for the preparation of Example 104. ¹H NMR (400 MHz, DMSO-d₆): δ ppm 1.57-1.65 (6H, m), 3.53-3.64 (4H, m), 3.99 (3H, s), 6.89 (1H, s), 7.66 (1H, d, J=4.8 Hz), 8.57 (1H, d, J=4.8 Hz), 11.47 (1H, s). LCMS (mobile phase: 5%-95% Acetonitrile-Water-0.02% NH₄Ac): purity is >95%, Rt=3.050 min. [M+H] Calc'd for $C_{15}H_{17}N_3O_3$, 288; Found, 288.

Example 109: 2-(piperidylcarbonyl)pyrrolo[3,2-b]pyridine-7-carboxylic Acid

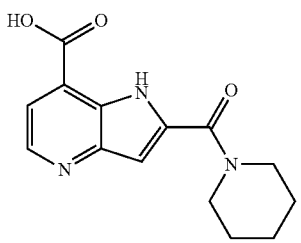 [SMILES: O=C(O)c1ccnc2cc(C(=O)N3CCCCC3)[nH]c12]

The title compound was prepared in 25% yield methyl 2-(piperidylcarbonyl)pyrrolo-[3,2-b]pyridine-7-carboxylate according to the procedure for the preparation in Example 5. ¹H NMR (400 MHz, DMSO-d₆): δ ppm 1.54-1.64 (6H, m), 3.46-3.63 (4H, m), 6.99 (1H, s), 7.80 (1H, d, J=5.2 Hz), 8.66 (1H, d, J=4.4 Hz), 11.85 (1H, s). LCMS (mobile phase: 5%-95% Acetonitrile-Water-0.02% NH₄Ac): purity is >95%, Rt=2.208 min. [M+H] Calc'd for $C_{14}H_{15}N_3O_3$, 274; Found, 274.

Example 110: 2-[1-(4-fluorophenyl)ethyl]-1H-pyrrolo[3,2-b]pyridine-7-carboxylic Acid

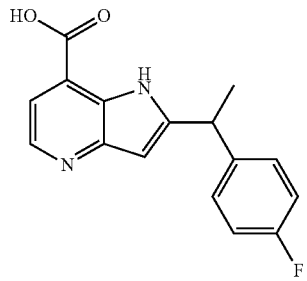

To a vial containing methyl 2-[1-(4-fluorophenyl)-1-hydroxyethyl]-1H-pyrrolo[3,2-b]-pyridine-7-carboxylate (31.4 mg, 0.1 mmol), and Et₃SiH (79 μL, 0.5 mmol) was added TFA (76 μL, 1 mmol). The reaction was stirred at ambient temp for 16 hr and concentrated in vacuo. The residue was taken up in MeOH (5 mL) followed by addition of Pd—C (50 mg, 10%), and kept under 1 ATM of H₂ at ambient temperature for 2 hrs. The suspension was filtered through a pad of celite and concentrated in vacuo. The residue was converted to title compound in 46% yield according to the procedure for the preparation in Example 5. ¹H NMR (400 MHz, DMSO-d₆): δ ppm 1.64 (d, J=7.07 Hz, 3H), 4.49-4.62 (m, 1H), 6.55 (s, 1H), 7.12 (t, J=8.72 Hz, 2H), 7.36 (dd, J=8.59, 5.56 Hz, 2H), 7.46 (d, J=5.56 Hz, 1H), 8.38 (d, J=4.80 Hz, 1H), 11.03-11.15 (m, 1H). [M+H] Calc'd for $C_{16}H_{13}FN_2O_2$, 275; Found, 275.

Example 111: methyl-2-(3-chloro-4-fluorobenzyl)-1H-pyrrolo[3,2-b]pyridine-7-carboxylate

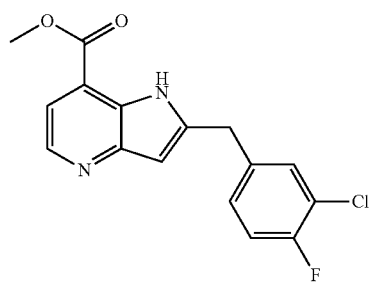

The title compound was prepared in 4% yield starting with 3-chloro-4-fluorobenzaldehyde according to the procedure for the preparation of Example 55. ¹H NMR (400 MHz, CDCl₃): δ ppm 4.00 (s, 3H), 4.18 (s, 2H), 6.56-6.63 (m, 1H), 7.11-7.31 (m, 2H), 7.29-7.31 (m, 2H), 7.61 (d, J=4.70 Hz, 1H), 8.53 (s, 1H), 9.35 (br. s., 1H). [M+H] Calc'd for $C_{16}H_{12}ClFN_2O_2$, 319; Found, 319.

Example 112: 2-(3-chloro-4-fluorobenzyl)-1H-pyrrolo[3,2-b]pyridine-7-carboxylic Acid

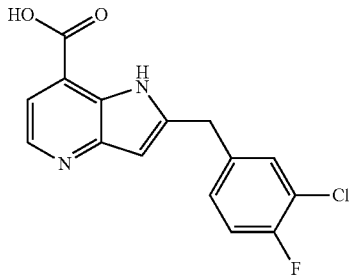 [SMILES: O=C(O)c1ccnc2cc(Cc3ccc(F)c(Cl)c3)[nH]c12]

The title compound was prepared in 78% yield using methyl-2-(3-chloro-4-fluorobenzyl)-1H-pyrrolo[3,2-b]pyridine-7-carboxylate according to the procedure for the preparation in Example 5. $^1$H NMR (400 MHz, DMSO-d$_6$): δ ppm 3.26-3.36 (m, 3H), 4.19-4.26 (m, 2H), 6.42 (s, 1H), 7.32-7.41 (m, 2H), 7.47 (d, J=4.80 Hz, 1H), 7.59 (d, J=7.83 Hz, 1H), 8.38 (d, J=5.05 Hz, 1H), 11.35 (br. s., 1H), 13.67 (br. s., 1H). [M+H] Calc'd for C$_{15}$H$_{10}$ClFN$_2$O$_2$, 305; Found, 305.

Example 113: methyl 2-(4-chloro-3-fluorobenzyl)-1H-pyrrolo[3,2-b]pyridine-7-carboxylate

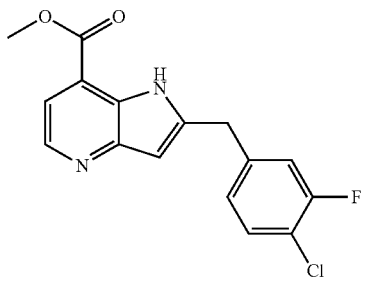

The title compound was prepared in 11% yield starting with 4-chloro-3-fluorobenzaldehyde according to the procedure for the preparation of Example 55. $^1$H NMR (400 MHz, CDCl$_3$): δ ppm 4.00 (s, 3H), 4.19 (s, 2H), 6.56-6.63 (m, 1H), 6.92-7.11 (m, 2H), 7.36 (t, J=7.83 Hz, 1H), 7.58 (d, J=4.80 Hz, 1H), 8.53 (d, J=5.05 Hz, 1H), 9.30 (br. s., 1H). [M+H] Calc'd for C$_{16}$H$_{12}$ClFN$_2$O$_2$, 319; Found, 319.

Example 114: 2-(4-chloro-3-fluorobenzyl)-1H-pyrrolo[3,2-b]pyridine-7-carboxylic Acid

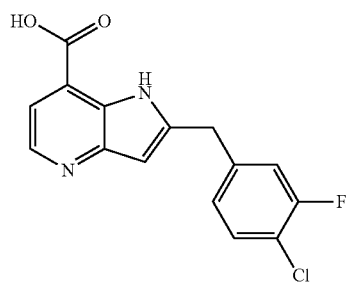

The title compound was prepared in 72% yield using methyl 2-(4-chloro-3-fluorobenzyl)-1H-pyrrolo[3,2-b]pyridine-7-carboxylate according to the procedure for the preparation in Example 5. $^1$H NMR (400 MHz, DMSO-d$_6$): δ ppm 4.24 (s, 2H), 6.43 (d, J=2.02 Hz, 1H), 7.19-7.27 (m, 1H), 7.42 (dd, J=10.48, 1.89 Hz, 1H), 7.47 (d, J=4.80 Hz, 1H), 7.52 (t, J=8.08 Hz, 1H), 8.39 (d, J=5.05 Hz, 1H), 11.35 (br. s., 1H), 13.67 (br. s., 1H). [M+H] Calc'd for C$_{15}$H$_{10}$ClFN$_2$O$_2$, 305; Found, 305.

Example 115: methyl 2-[(3-phenylpyrrolidinyl)carbonyl]pyrrolo[3,2-b]-pyridine-7-carboxylate

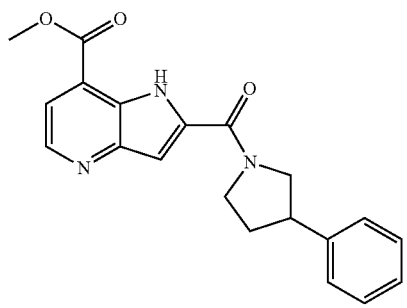 [SMILES: COC(=O)c1ccnc2cc(C(=O)N3CCC(c4ccccc4)C3)[nH]c12]

The title compound was prepared in 20% yield starting with 3-phenylpyrrolidine according to the procedure for the preparation of Example 104. $^1$H NMR (400 MHz, CDCl$_3$): δ ppm 2.15-2.27 (1H, m), 2.41-2.56 (1H, m), 3.49-3.61 (1H, m), 3.74-3.89 (2H, m), 4.01-4.07 (4H, m), 4.17-4.44 (1H, m), 7.16 (1H, d, J=16.8 Hz), 7.28-7.35 (3H, m), 7.36-7.39 (2H, m), 7.77-7.80 (1H, m), 8.64-8.67 (1H, m), 10.56 (1H, s). LCMS (mobile phase: 10%-95% Acetonitrile-Water-0.02% NH$_4$Ac): purity is >95%, Rt=3.782 min. [M+H] Calc'd for C$_{20}$H$_{19}$N$_3$O$_3$, 350; Found, 350.

Example 116: 2-[(3-phenylpyrrolidinyl)carbonyl]pyrrolo[3,2-b]pyridine-7-carboxylic Acid

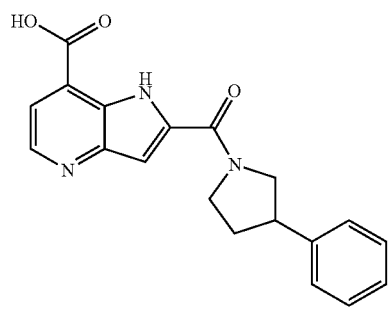 [SMILES: O=C(O)c1ccnc2cc(C(=O)N3CCC(c4ccccc4)C3)[nH]c12]

The title compound was prepared in 82% yield methyl 2-[(3-phenylpyrrolidinyl)-carbonyl]pyrrolo[3,2-b]pyridine-7-carboxylate according to the procedure for the preparation in Example 5. $^1$H NMR (400 MHz, DMSO-d$_6$): δ ppm 2.05-2.17 (1H, m), 2.31-2.47 (1H, m), 3.46-3.57 (1.5H, m), 3.63-3.66 (0.5H, m), 3.83-3.88 (1H, m), 3.95-4.02 (0.5H, m), 4.07-4.12 (1H, m), 4.31-4.36 (0.5H, m), 7.24-7.40 (6H, m), 7.68-7.71 (1H, m), 8.60-8.64 (1H, m), 10.45-10.49 (1H, m), 14.12 (1H, br). LCMS (mobile phase: 5%-95% Acetonitrile-Water-0.02% NH$_4$Ac): purity is >95%, Rt=2.671 min. [M+H] Calc'd for C$_{18}$H$_{17}$N$_3$O$_3$, 336; Found, 336.

Example 117: methyl 2-[(4,4-dimethylpiperidyl)carbonyl]pyrrolo[3,2-b]-pyridine-7-carboxylate

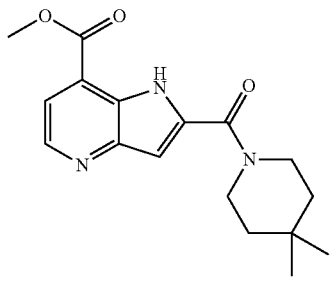

The title compound was prepared in 21% yield starting with 4,4-dimethylpiperidine according to the procedure for the preparation of Example 104. $^1$H NMR (300 MHz, CDCl$_3$): δ ppm 1.07 (6H, s), 1.47-1.51 (4H, m), 3.78-3.93 (4H, m), 4.06 (3H, s), 7.01 (1H, s), 7.77 (1H, d, J=4.8 Hz), 8.65 (1H, d, J=4.8 Hz), 10.03 (1H, bs). LCMS (mobile phase: 10%-95% Acetonitrile-Water-0.02% NH$_4$Ac): purity is >95%, Rt=3.407 min. [M+H] Calc'd for C$_{17}$H$_{21}$N$_3$O$_3$, 316; Found, 316.

Example 118: 2-[(4,4-dimethylpiperidyl)carbonyl]pyrrolo[3,2-b]pyridine-7-carboxylic Acid

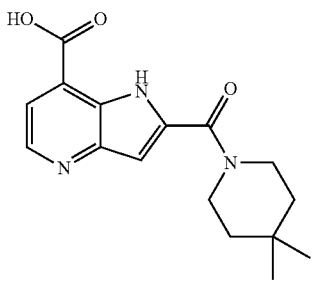 [SMILES: CC1(C)CCN(C(=O)c2cc3nccc(C(=O)O)c3[nH]2)CC1]

The title compound was prepared in 70% yield methyl 2-[(4,4-dimethylpiperidyl)-carbonyl]pyrrolo[3,2-b]pyridine-7-carboxylate according to the procedure for the preparation in Example 5. $^1$H NMR (400 MHz, DMSO-d$_6$): δ ppm 1.54-1.64 (6H, m), 3.46-3.63 (4H, m), 6.99 (1H, s), 7.80 (1H, d, J=5.2 Hz), 8.66 (1H, d, J=4.4 Hz), 11.85 (1H, s). LCMS (mobile phase: 5%-95% Acetonitrile-Water-0.02% NH$_4$Ac): purity is >95%, Rt=2.208 min. [M+H] Calc'd for C$_{14}$H$_{15}$N$_3$O$_3$, 274; Found, 274.

Example 119: methyl 2-[(3-phenylpiperidyl)carbonyl]pyrrolo[3,2-b]pyridine-7-carboxylate

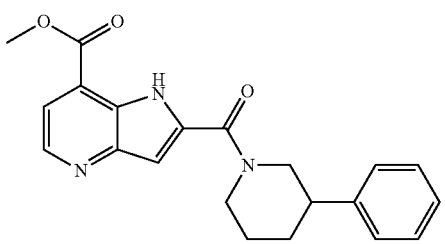 [SMILES: COC(=O)c1ccnc2cc(C(=O)N3CCCC(c4ccccc4)C3)[nH]c12]

The title compound was prepared in 12% yield starting with 3-phenylpiperidine according to the procedure for the preparation of Example 104. $^1$H NMR (400 MHz, CDCl$_3$): δ ppm 1.69-1.83 (3H, m), 1.86-1.99 (1H, m), 2.81-2.85 (2H, m), 2.89-2.94 (1H, m), 3.96-3.99 (4H, m), 4.57-4.60 (1H, m), 6.95 (1H, s), 7.17-7.35 (5H, m), 7.66-7.67 (1H, m), 7.78 (1H, d, J=4.4 Hz), 8.57 (1H, br), 11.58 (1H, bs). LCMS (mobile phase: 20%-95% Acetonitrile-Water-0.02% NH$_4$Ac): purity is >95%, Rt=3.323 min. [M+H] Calc'd for C$_{21}$H$_{21}$N$_3$O$_3$, 364; Found, 364.

Example 120: 2-[(3-phenylpiperidyl)carbonyl]pyrrolo[3,2-b]pyridine-7-carboxylic Acid

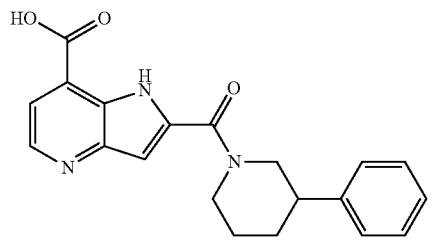 [SMILES: O=C(O)c1ccnc2cc(C(=O)N3CCCC(c4ccccc4)C3)[nH]c12]

The title compound was prepared in 50% yield methyl 2-[(3-phenylpiperidyl)carbonyl]-pyrrolo[3,2-b]pyridine-7-carboxylate according to the procedure for the preparation in Example 5. $^1$H NMR (400 MHz, DMSO-d$_6$): δ ppm 1.55-2.05 (5H, m), 2.75-3.02 (2H, m), 3.32-3.38 (2H, m), 6.91 (1H, bs), 7.18-7.45 (5H, m), 7.68-7.72 (1H, m), 8.65 (1H, br), 11.88 (1H, bs). LCMS (mobile phase: 5%-95% Acetonitrile-Water-0.02% NH$_4$Ac): purity is >95%, Rt=2.619 min. [M+H] Calc'd for C$_{20}$H$_{19}$N$_3$O$_3$, 350; Found, 350.

Example 121: methyl 2-(2-1,2,3,4-tetrahydroisoquinolylcarbonyl)pyrrolo[3,2-b]-pyridine-7-carboxylate

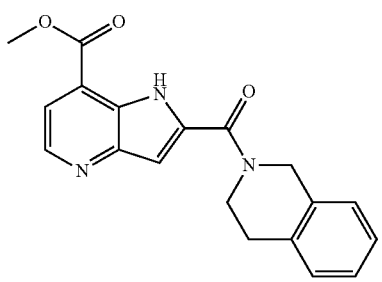 [SMILES: COC(=O)c1ccnc2cc(C(=O)N3CCc4ccccc4C3)[nH]c12]

The title compound was prepared in 35% yield starting with 1,2,3,4-tetrahydroisoquinoline according to the procedure for the preparation of Example 104. $^1$H NMR (400 MHz, CD$_3$OD): δ ppm 2.88-2.91 (2H, m), 3.86-3.89 (2H, m), 3.94 (3H, s), 4.88 (2H, br), 6.96-7.09 (5H, m), 7.70 (1H, d, J=4.8 Hz), 8.46 (1H, d, J=4.4 Hz). LCMS (mobile phase: 10%-95% Acetonitrile-Water-0.02% NH$_4$Ac): purity is >95%, Rt=2.468 min. [M+H] Calc'd for C$_{19}$H$_{17}$N$_3$O$_3$, 336; Found, 336.

Example 122: 2-(2-1,2,3,4-tetrahydroisoquinolylcarbonyl)pyrrolo[3,2-b]-pyridine-7-carboxylic Acid

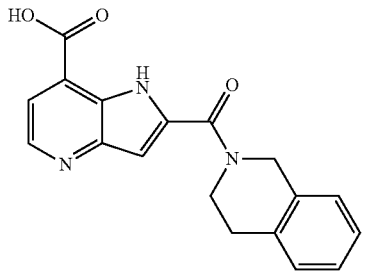 [SMILES: O=C(O)c1ccnc2cc(C(=O)N3CCc4ccccc4C3)[nH]c12]

The title compound was prepared in 65% yield methyl methyl 2-(2-1,2,3,4-tetrahydro-isoquinolylcarbonyl)pyrrolo[3,2-b]pyridine-7-carboxylate according to the procedure for the preparation in Example 5. ¹H NMR (400 MHz, DMSO-d₆): δ 2.93-2.95 (2H, m), 3.85-3.88 (2H, m), 4.82-4.89 (2H, m), 7.09-7.30 (5H, m), 7.70 (1H, d, J=4.8 Hz), 8.61 (1H, d, J=4.8 Hz), 11.26-11.28 (1H, br). LCMS (mobile phase: 5%-95% Acetonitrile-Water-0.02% NH₄Ac): purity is >95%, Rt=2.468 min. [M+H] Calc'd for $C_{18}H_{15}N_3O_3$, 322; Found, 322.

Example 123: methyl 2-[(2,2-dimethylpyrrolidinyl)carbonyl]pyrrolo[3,2-b]-pyridine-7-carboxylate

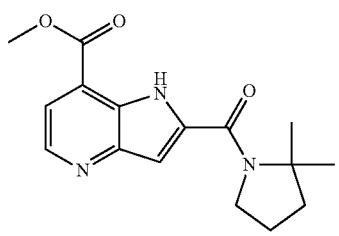

The title compound was prepared in 35% yield starting with 2,2-dimethylpyrrolidine according to the procedure for the preparation of Example 104. ¹H NMR (300 MHz, CDCl₃): δ ppm 1.62 (6H, s), 1.80-1.95 (2H, m), 1.99-2.06 (2H, m), 3.98-4.02 (2H, m), 4.06 (3H, s), 7.09 (1H, d, J=2.4 Hz), 7.78 (1H, d, J=4.8 Hz), 8.64 (1H, d, J=4.8 Hz), 10.22 (1H, bs). LCMS (mobile phase: 10%-95% Acetonitrile-Water-0.02% NH₄Ac): purity is >95%, Rt=3.404 min. [M+H] Calc'd for $C_{16}H_{19}N_3O_3$, 302; Found, 302.

Example 124: 2-[(2,2-dimethylpyrrolidinyl)carbonyl]pyrrolo[3,2-b]-pyridine-7-carboxylic Acid

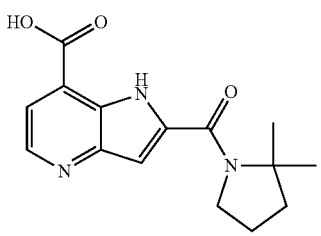 [SMILES: CC1(C)CCCN1C(=O)c1cc2nccc(C(=O)O)c2[nH]1]

The title compound was prepared in 50% yield methyl 2-[(2,2-dimethylpyrrolidinyl)-carbonyl]pyrrolo[3,2-b]pyridine-7-carboxylate according to the procedure for the preparation in Example 5. ¹H NMR (300 MHz, DMSO-d₆): δ ppm 1.52 (6H, s), 1.83-1.92 (4H, m), 3.83-3.86 (2H, m), 7.15 (1H, s), 7.72 (1H, d, J=4.8 Hz), 8.62 (1H, d, J=4.8 Hz), 10.73 (1H, bs). LCMS (mobile phase: 5%-95% Acetonitrile-Water-0.02% NH₄Ac): purity is >95%, Rt=2.296 min. [M+H] Calc'd for $C_{15}H_{17}N_3O_3$, 288; Found, 288.

Example 125: methyl 2-(3,4-difluorobenzyl)-1H-pyrrolo[3,2-b]pyridine-7-carboxylate

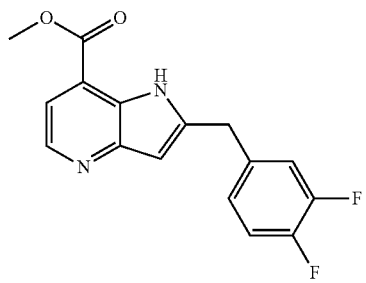

The title compound was prepared in 17% yield starting with 3,4-difluorobenzaldehyde according to the procedure for the preparation of Example 55. ¹H NMR (400 MHz, CDCl₃): δ ppm 4.00 (s, 3H), 4.18 (s, 2H), 6.55-6.65 (m, 1H), 6.94-7.18 (m, 3H), 7.58 (d, J=5.05 Hz, 1H), 8.53 (d, J=5.05 Hz, 1H), 9.31 (br. s., 1H). [M+H] Calc'd for $C_{16}H_{12}F_2N_2O_2$, 303; Found, 303.

Example 126: 2-(3,4-difluorobenzyl)-1H-pyrrolo[3,2-b]pyridine-7-carboxylic Acid

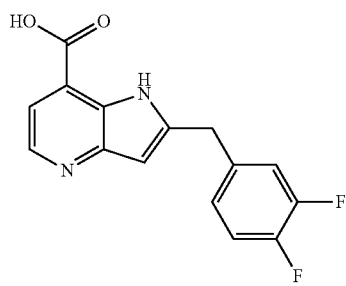 [SMILES: O=C(O)c1ccnc2cc(Cc3ccc(F)c(F)c3)[nH]c12]

The title compound was prepared in 87% yield using methyl 2-(3,4-difluorobenzyl)-1H-pyrrolo[3,2-b]pyridine-7-carboxylate according to the procedure for the preparation in Example 5. ¹H NMR (400 MHz, DMSO-d₆): δ ppm 4.22 (s, 2H), 6.33-6.46 (m, 1H), 7.20 (br. s., 1H), 7.31-7.45 (m, 2H), 7.47 (d, J=4.80 Hz, 1H), 8.38 (d, J=5.05 Hz, 1H), 11.34 (br. s., 1H), 13.67 (br. s., 1H). [M+H] Calc'd for $C_{15}H_{10}F_2N_2O_2$, 289; Found, 289.

Example 127: methyl 2-(4-chloro-3-methoxybenzyl)-1H-pyrrolo[3,2-b]-pyridine-7-carboxylate

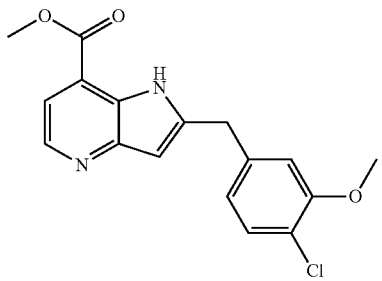

The title compound was prepared in <1% yield starting with 3-methoxy-4-chloro-benzaldehyde according to the procedure for the preparation of Example 59. $^1$H NMR (400 MHz, CDCl$_3$): δ ppm 3.87 (s, 3H), 4.04 (s, 3H), 4.23 (s, 2H), 6.76-6.90 (m, 2H), 7.35 (d, J=8.08 Hz, 2H), 7.64-7.78 (m, 1H), 8.51 (d, J=5.56 Hz, 1H), 9.45-9.62 (m, 1H). [M+H] Calc'd for C$_{17}$H$_{15}$ClN$_2$O$_3$: 331; Found: 331.

Example 128: 2-(4-chloro-3-methoxybenzyl)-1H-pyrrolo[3,2-b]-pyridine-7-carboxylic Acid

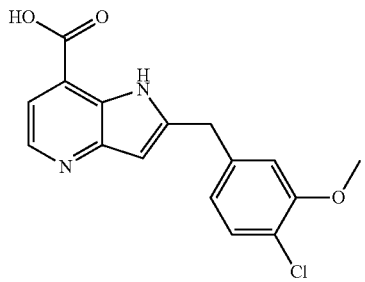 [SMILES: COc1cc(Cc2cc3nccc(C(=O)O)c3[nH]2)ccc1Cl]

The title compound was prepared in 12% yield using methyl 2-(4-chloro-3-methoxy-benzyl)-1H-pyrrolo[3,2-b]pyridine-7-carboxylate according to the procedure in Example 5. $^1$H NMR (400 MHz, CD$_3$OD): δ ppm 3.80-3.92 (m, 3H), 4.31 (s, 2H), 6.43-6.50 (m, 1H), 6.82-6.95 (m, 1H), 7.03-7.14 (m, 1H), 7.25-7.39 (m, 1H), 7.73-7.82 (m, 1H), 8.34-8.46 (m, 1H). [M+H] Calc'd for C$_{16}$H$_{13}$ClN$_2$O$_3$, 317; Found, 317.

Example 129: methyl 2-(3,4-dichlorobenzyl)-1H-pyrrolo[3,2-b]pyridine-7-carboxylate

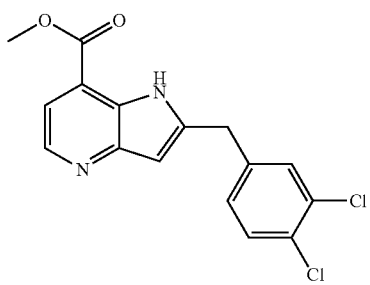 [SMILES: COC(=O)c1ccnc2cc(Cc3ccc(Cl)c(Cl)c3)[nH]c12]

The title compound was prepared in <5% yield starting with 3,4-dichlorobenzaldehyde according to the procedure for the preparation of Example 55. $^1$H NMR (400 MHz, CDCl$_3$): δ ppm 4.02 (s, 3H), 4.19 (s, 2H), 6.62-6.79 (m, 1H), 7.11 (d, J=10.11 Hz, 1H), 7.36 (m, 1H), 7.42 (d, J=8.08 Hz, 1H), 7.60-7.68 (m, 1H), 8.48-8.59 (m, 1H), 9.31-9.46 (m, 1H). [M+H] Calc'd for C$_{16}$H$_{12}$Cl$_2$N$_2$O$_2$, 335; Found, 335.

Example 130: 2-(3,4-dichlorobenzyl)-1H-pyrrolo[3,2-b]pyridine-7-carboxylic Acid

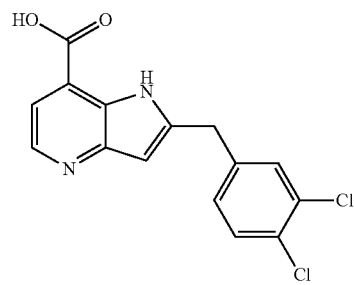 [SMILES: O=C(O)c1ccnc2cc(Cc3ccc(Cl)c(Cl)c3)[nH]c12]

The title compound was prepared in 70% yield using methyl 2-(3,4-dichlorobenzyl)-1H-pyrrolo[3,2-b]pyridine-7-carboxylate according to the procedure for the preparation in Example 5. $^1$H NMR (400 MHz, DMSO-d$_6$): δ ppm 4.23 (s, 2H), 6.45 (d, J=2.02 Hz, 1H), 7.32-7.38 (m, 1H), 7.48 (d, J=4.80 Hz, 1H), 7.57 (d, J=8.34 Hz, 1H), 7.63-7.68 (m, 1H), 8.39 (d, J=4.80 Hz, 1H), 11.32-11.46 (m, 1H), 13.68 (br. s., 1H). [M+H] Calc'd for C$_{15}$H$_{10}$Cl$_2$N$_2$O$_2$, 321; Found, 321.

Example 131: methyl 2-(3,4-dichloro-5-fluorobenzyl)-1H-pyrrolo[3,2-b]-pyridine-7-carboxylate

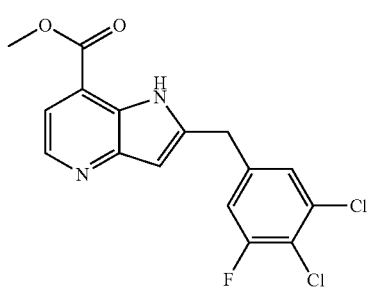

The title compound was prepared in 13% yield starting with 3,4-dichloro-5-fluoro-benzaldehyde according to the procedure for the preparation of Example 55. $^1$H NMR (400 MHz, CDCl$_3$): δ ppm 4.02 (s, 3H), 4.19 (s, 2H), 6.65-6.74 (m, 1H), 6.98 (d, J=7.33 Hz, 1H), 7.19 (s, 1H), 7.64 (d, J=5.05 Hz, 1H), 8.55 (d, J=5.30 Hz, 1H), 9.40 (br. s., 1H). [M+H] Calc'd for C$_{16}$H$_{11}$FCl$_2$N$_2$O$_2$, 353; Found, 353.

Example 132: 2-(3,4-dichloro-5-fluorobenzyl)-1H-pyrrolo[3,2-b]pyridine-7-carboxylic Acid

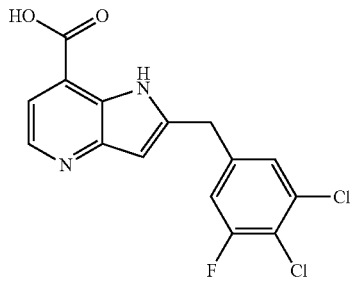 [SMILES: O=C(O)c1ccnc2cc(Cc3cc(F)c(Cl)c(Cl)c3)[nH]c12]

The title compound was prepared in 80% yield using methyl 2-(3,4-dichloro-5-fluorobenzyl)-1H-pyrrolo[3,2-b]pyridine-7-carboxylate according to the procedure for the preparation in Example 5. $^1$H NMR (400 MHz, DMSO-d$_6$): δ ppm 4.24 (s, 2H), 6.47-6.51 (m, 1H), 7.44-7.46 (m, 1H), 7.47-7.49 (m, 1H), 7.54-7.58 (m, 1H), 8.39 (d, J=4.80 Hz, 1H), 11.33-11.42 (m, 1H), 13.63-13.73 (m, 1H). [M+H] Calc'd for $C_{15}H_9FCl_2N_2O_2$, 339; Found, 339.

Example 133: methyl-2-(4-chloro-3-methylbenzyl)-1H-pyrrolo[3,2-b]-pyridine-7-carboxylate

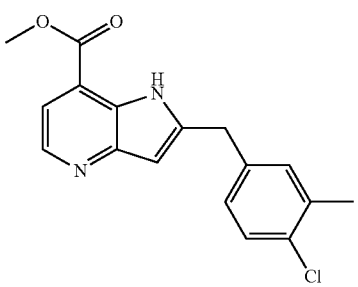

The title compound was prepared in 6% yield starting with 3-methyl-4-chlorobenzaldehyde according to the procedure for the preparation of Example 55. $^1$H NMR (400 MHz, CD$_3$OD): δ 2.37 (3H, s), 4.05 (3H, s), 4.23 (2H, s), 6.37 (1H, s), 7.13-7.16 (1H, m), 7.27 (1H, d, J=2.0 Hz), 7.32 (1H, d, J=8.0 Hz), 7.65 (1H, d, J=5.2 Hz), 8.38 (1H, d, J=5.2 Hz). [M+H] Calc'd for $C_{17}H_{15}ClN_2O_2$, 315; Found, 315.

Example 134: 2-(4-chloro-3-methylbenzyl)-1H-pyrrolo[3,2-b]pyridine-7-carboxylic Acid

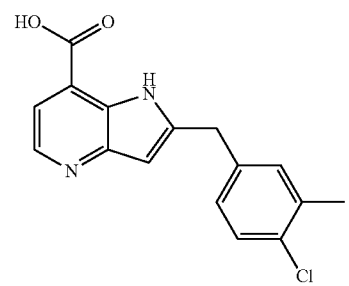 [SMILES: Cc1cc(Cc2cc3nccc(C(=O)O)c3[nH]2)ccc1Cl]

The title compound was prepared in 80% yield using methyl-2-(4-chloro-3-methyl-benzyl)-1H-pyrrolo[3,2-b]pyridine-7-carboxylate according to the procedure for the preparation in Example 5. $^1$H NMR (400 MHz, DMSO-d$_6$): δ ppm 2.30 (3H, s), 4.23 (2H, s), 6.48 (1H, s), 7.19-7.21 (1H, m), 7.34-7.36 (2H, m), 7.62 (1H, d, J=5.6 Hz), 8.48 (1H, d, J=5.2 Hz), 11.76 (1H, s). [M+H] Calc'd for $C_{16}H_{13}ClN_2O_2$, 301; Found, 301.

Example 135: methyl 2-[4-chloro-3-(trifluoromethyl)benzyl]-1H-pyrrolo[3,2-b]-pyridine-7-carboxylate

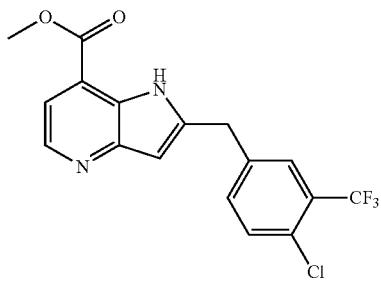 [SMILES: COC(=O)c1ccnc2cc(Cc3ccc(Cl)c(C(F)(F)F)c3)[nH]c12]

The title compound was prepared in <5% yield starting with 3-trifluoromethyl-4-chlorobenzaldehyde according to the procedure for the preparation of Example 55. $^1$H NMR (400 MHz, DMSO-d$_6$): δ 3.98 (3H, s), 4.33 (2H, s), 6.47 (1H, s), 7.51 (1H, d, J=4.8 Hz), 7.66-7.69 (2H, m), 7.91 (1H, s), 8.42 (1H, d, J=5.2 Hz), 11.46 (1H, s). [M+H] Calc'd for $C_{17}H_{12}ClF_3N_2O_2$, 369; Found, 369.

Example 136: 2-[4-chloro-3-(trifluoromethyl)benzyl]-1H-pyrrolo[3,2-b]-pyridine-7-carboxylic Acid

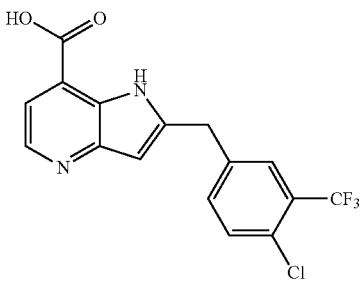

The title compound was prepared in 65% yield using methyl-2-(4-chloro-3-trifluoromethylbenzyl)-1H-pyrrolo[3,2-b]pyridine-7-carboxylate according to the procedure for the preparation in Example 5. $^1$H NMR (400 MHz, DMSO-d$_6$): δ ppm 4.32 (2H, s), 6.48 (1H, s), 7.49 (1H, d, J=5.2 Hz), 7.66-7.69 (2H, m), 7.90 (1H, s), 8.40 (1H, d, J=4.4 Hz), 11.45 (1H, s). [M+H] Calc'd for $C_{16}H_{10}ClF_3N_2O_2$, 355; Found, 355.

Example 137: Methyl 2-[4-chloro-3-(cyclopropyl-methoxy)benzyl]-1H-pyrrolo[3,2-b]-pyridine-7-carboxylate

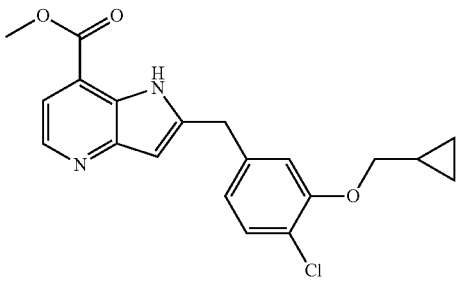 [SMILES: COC(=O)c1ccnc2cc(Cc3ccc(Cl)c(OCC4CC4)c3)[nH]c12]

The title compound was prepared in <5% yield starting with 3-(cyclopropylmethoxy)-4-chlorobenzaldehyde according to the procedure for the preparation of Example 55. 1H NMR (400 MHz, CD$_3$OD): δ 0.33-0.36 (2H, m), 0.55-0.60 (2H, m), 1.24-1.27 (1H, m), 3.87 (2H, d, J=6.4 Hz), 4.03 (3H, s), 4.21 (2H, s), 6.36 (1H, s), 6.84-6.86 (1H, m), 7.01 (1H, d, J=1.6 Hz), 7.28 (1H, d, J=8.0 Hz), 7.61 (1H, d, J=5.2 Hz), 8.34 (1H, d, J=5.2 Hz). [M+H] Calc'd for C$_{20}$H$_{19}$ClN$_2$O$_3$, 371; Found, 371.

Example 138: 2-[4-chloro-3-(cyclopropylmethoxy)benzyl]-1H-pyrrolo[3,2-b]-pyridine-7-carboxylic Acid

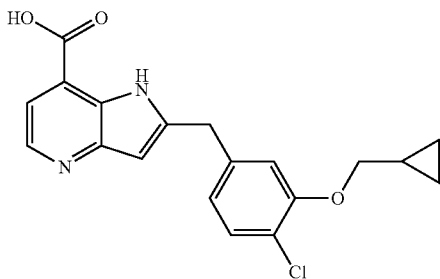 [SMILES: O=C(O)c1ccnc2cc(Cc3ccc(Cl)c(OCC4CC4)c3)[nH]c12]

The title compound was prepared in 65% yield using methyl-2-(4-chloro-3-trifluoromethyl-benzyl)-1H-pyrrolo[3,2-b]pyridine-7-carboxylate according to the procedure for the preparation in Example 5. $^1$H NMR (400 MHz, DMSO-d$_6$): δ ppm 0.33-0.36 (2H, m), 0.55-0.60 (2H, m), 1.22-1.26 (1H, m), 3.87 (2H, d, J=6.4 Hz), 4.21 (2H, s), 6.48 (1H, s), 6.90-6.92 (1H, m), 7.21 (1H, d, J=2.0 Hz), 7.34 (1H, d, J=8.0 Hz), 7.61 (1H, d, J=5.2 Hz), 8.47 (1H, d, J=5.2 Hz), 11.39 (1H, s). [M+H] Calc'd for C$_{19}$H$_{17}$ClN$_2$O$_3$, 357; Found, 357.

Example 139: methyl-2-[4-chloro-3-(2,2,2-trifluoroethoxy)benzyl]-1H-pyrrolo[3,2-b]-pyridine-7-carboxylate

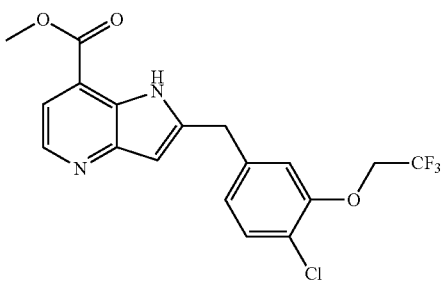 [SMILES: COC(=O)c1ccnc2cc(Cc3ccc(Cl)c(OCC(F)(F)F)c3)[nH]c12]

The title compound was prepared in <5% yield starting with 3-(2,2,2-trifluoroethoxy)-4-chlorobenzaldehyde according to the procedure for the preparation of Example 55. $^1$H NMR (400 MHz, CD$_3$OD): δ 4.06 (3H, s), 4.28 (2H, s), 4.58-4.64 (2H, m), 6.41 (1H, s), 7.01-7.04 (1H, m), 7.18 (1H, d, J=2.0 Hz), 7.40 (1H, d, J=8.4 Hz), 7.65 (1H, d, J=4.8 Hz), 8.38 (1H, d, J=5.2 Hz). [M+H] Calc'd for C$_{18}$H$_{14}$F$_3$ClN$_2$O$_3$, 399; Found, 399.

Example 140: 2-[4-chloro-3-(2,2,2-trifluoroethoxy)benzyl]-1H-pyrrolo[3,2-b]-pyridine-7-carboxylic Acid

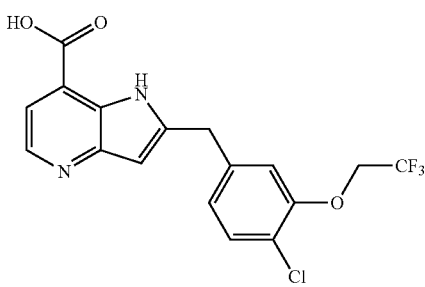 [SMILES: O=C(O)c1ccnc2cc(Cc3ccc(Cl)c(OCC(F)(F)F)c3)[nH]c12]

The title compound was prepared in 80% yield using methyl-2-[4-chloro-3-(2,2,2-tri-fluoroethoxy)benzyl]-1H-pyrrolo[3,2-b]pyridine-7-carboxylate according to the procedure for the preparation in Example 5. $^1$H NMR (400 MHz, DMSO-d$_6$): δ ppm 4.23 (2H, s), 4.81-4.88 (2H, m), 6.41 (1H, s), 7.02-7.05 (1H, m), 7.35 (1H, d, J=1.2 Hz), 7.41 (1H, d, J=8.0 Hz), 7.52 (1H, d, J=5.2 Hz), 8.41 (1H, d, J=4.8 Hz), 11.45 (1H, s). [M+H] Calc'd for C$_{17}$H$_{12}$F$_3$ClN$_2$O$_3$, 385; Found, 385.

Example 141: methyl-2-[4-chloro-3-(trifluoromethoxy)benzyl]-1H-pyrrolo[3,2-b]-pyridine-7-carboxylate

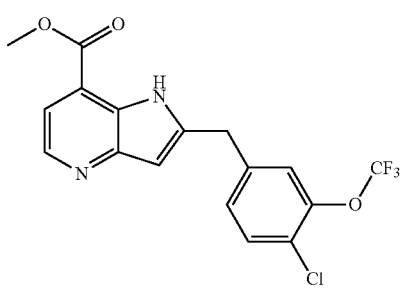 [SMILES: COC(=O)c1ccnc2cc(Cc3ccc(Cl)c(OC(F)(F)F)c3)[nH]c12]

The title compound was prepared in 8% yield starting with 3-(trifluoromethoxy)-4-chloro-benzaldehyde according to the procedure for the preparation of Example 59. $^1$H NMR (400 MHz, CDCl$_3$): δ ppm 4.03 (s, 3H), 4.24 (s, 2H), 6.64-6.82 (m, 1H), 7.15 (d, J=10.11 Hz, 1H), 7.46 (d, J=8.08 Hz, 2H), 7.63-7.77 (m, 1H), 8.53 (d, J=5.31 Hz, 1H), 9.40-9.57 (m, 1H). [M+H] Calc'd for C$_{17}$H$_{12}$F$_3$ClN$_2$O$_3$, 385; Found, 385.

Example 142: 2-[4-chloro-3-(trifluoromethoxy)benzyl]-1H-pyrrolo[3,2-b]-pyridine-7-carboxylic Acid

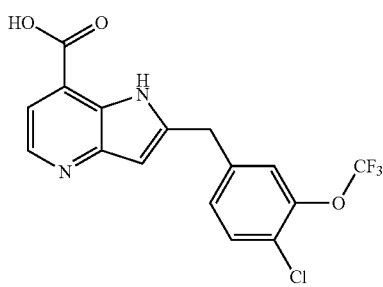 [SMILES: O=C(O)c1ccnc2cc(Cc3ccc(Cl)c(OC(F)(F)F)c3)[nH]c12]

The title compound was prepared in 92% yield using methyl-2-[4-chloro-3-(trifluoro-methoxy)benzyl]-1H-pyrrolo[3,2-b]pyridine-7-carboxylate according to the procedure for the preparation in Example 5. $^1$H NMR (400 MHz, DMSO-$d_6$): δ ppm 4.28 (s, 3H), 6.40-6.46 (m, 1H), 7.37-7.43 (m, 1H), 7.48 (d, J=4.80 Hz, 1H), 7.58-7.65 (m, 3H), 8.39 (d, J=4.80 Hz, 1H), 11.38 (br. s., 1H), 13.67 (s, 1H). [M+H] Calc'd for $C_{17}H_{12}ClN_2O_3$, 371; Found, 371.

Example 143: 2-[4-chloro-benzyl]-N-methyl-1H-pyrrolo[3,2-b]pyridine-7-carboxamide

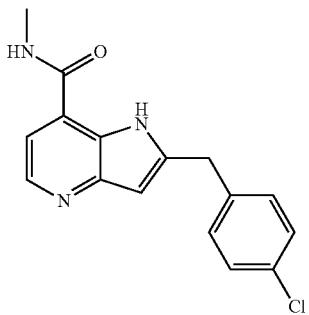 [SMILES: CNC(=O)c1ccnc2cc(Cc3ccc(Cl)cc3)[nH]c12]

To a vial charged with 2-(4-chlorobenzyl)-1H-pyrrolo[3,2-b]pyridine-7-carboxylic acid (75 mg, 0.262 mmol) in DMF (2 mL) was added HATU (150 mg, 0.393 mmol), DIEA (191 µL, 1 mmol) and MeNH$_2$—HCl (26 mg, 0.393 mmol). The reaction was allowed to stir for 16 hr at ambient temp. The crude mixture was purified by prep-HPLC (5-95% gradient of ACN in water with 0.1% HCO$_2$H) to afford the title compound as orange solid. $^1$H NMR (400 MHz, DMSO-$d_6$): δ ppm 2.81-2.92 (m, 3H), 4.12-4.27 (m, 2H), 6.28-6.37 (m, 1H), 7.36 (m, 5H), 8.32 (d, J=5.05 Hz, 1H), 8.70-8.83 (m, 1H), 11.30 (br. s., 1H). [M+H] Calc'd for $C_{16}H_{14}ClN_3O$, 300; Found, 300.

Example 144: 2-[4-chloro-3-(trifluoromethoxy)benzyl]-N-methyl-1H-pyrrolo[3,2-b]-pyridine-7-carboxamide

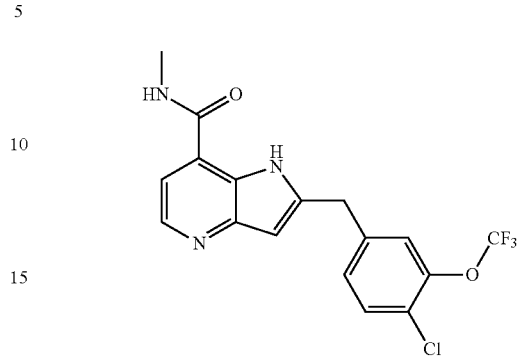

The title compound was prepared in 49% yield using 2-[4-chloro-3-(trifluoromethoxy)-benzyl]-1H-pyrrolo[3,2-b]pyridine-7-carboxylic acid according to the procedure for the preparation in Example 143. $^1$H NMR (400 MHz, CDCl$_3$): δ ppm 2.89-3.20 (m, 3H), 4.05-4.14 (m, 1H), 4.24 (s, 2H), 6.60-6.80 (m, 1H), 7.05-7.18 (m, 1H), 7.41-7.58 (m, 2H), 7.93-8.12 (m, 1H), 8.36 (br. s., 1H), 10.24 (s, 1H). [M+H] Calc'd for $C_{17}H_{13}F_3ClN_3O_2$, 384; Found, 384.

II. Biological Evaluation

Example 1: In Vitro Enzyme Inhibition Assay

This assay determines the ability of a test compound to inhibit Jarid1A, Jarid1B, JMJD2C, and JMJD2A demethylase activity. Baculovirus expressed Jarid1A (GenBank Accession #NM_001042603, AA1-1090) was purchased from BPS Bioscience (Cat#50110). Baculovirus expressed Jarid1B (GenBank Accession #NM_006618, AA 2-751) was purchased from BPS Bioscience (Cat #50121) or custom made by MolecularThroughput. Baculovirus expressed JMJD2C (GenBank Accession #BC143571, AA 2-372) was purchased from BPS Bioscience (Cat#50105). Baculovirus expressed JMJD2A (GenBank Accession #NM_014663, AA 1-350) was purchased from BPS Bioscience (Cat#50123).

Jarid1A Assay

The enzymatic assay of Jarid1A activity is based upon Time Resolved-Fluorescence Resonance Energy Transfer (TR-FRET) detection. The ability of test compounds to inhibit the activity of Jarid1A was determined in 384-well plate format under the following reaction conditions: 1 nM Jarid1A, 300 nM H3K4me3-biotin labeled peptide (Anaspec cat #64357), 2 µM α-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of plate, followed by the addition of 2 µl of 3 nM Jarid1A to initiate the reaction. The reaction mixture was incubated at room temp for 30 min, and terminated by the addition of 6 μl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hr incubation at room temp. A ratio was calculated (665/615) for each well and fitted to determine inhibition constant ($IC_{50}$).

Jarid1B Assay

The ability of test compounds to inhibit the activity of Jarid1B was determined in 384-well plate format under the following reaction conditions: 0.8 nM Jarid1B, 300 nM H3K4me3-biotin labeled peptide (Anaspec cat #64357), 2 μM α-ketoglutaric acid in assay buffer of 50 mM HEPES, pH 7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 μl of the mixture of 900 nM H3K4me3-biotin labeled peptide and 6 μM α-ketoglutaric acid with 2 μl of 11-point serial diluted inhibitor in 3% DMSO was added to each well of the plate, followed by the addition of 2 μl of 2.4 nM Jarid1B to initiate the reaction. The reaction mixture was incubated at room temp for 30 min, and terminated by the addition of 6 μl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hr incubation at room temp. A ratio was calculated (665/615) for each well and fitted to determine inhibition constant ($IC_{50}$).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 μM α-ketoglutaric acid in assay buffer of 50 mM HEPES, pH 7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM α-ketoglutaric acid with 2 μl of 11-point serial diluted inhibitor in 3% DMSO were added to each well of the plate, followed by the addition of 2 μl of 0.9 nM JMJD2C to initiate the reaction. The reaction mixture was incubated at room temp for 30 min, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hr incubation at room temp. A ratio was calculated (665/615) for each well and fitted to determine inhibition constant ($IC_{50}$).

JMJD2A Assay

The ability of test compounds to inhibit the activity of JMJD2A was determined in 384-well plate format under the following reaction conditions: 2 nM JMJD2A, 300 nM H3K9me3-biotin labeled peptide (Anaspec cat #64360), 2 μM α-ketoglutaric acid in assay buffer of 50 mM HEPES, pH 7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM α-ketoglutaric acid with 2 μl of 11-point serial diluted inhibitor in 3% DMSO were added to each well of plate, followed by the addition of 2 μl of 6 nM JMJD2A to initiate the reaction. The reaction mixture was incubated at room temperature for 30 minutes, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hr incubation at room temp. A ratio was calculated (665/615) for each well and fitted to determine inhibition constant ($IC_{50}$).

The ability of the compounds disclosed herein to inhibit demethylase activity was quantified and the respective $IC_{50}$ value was determined. Table 3 provides the $IC_{50}$ values of various compounds disclosed herein.

TABLE 3

| Chemical Synthesis Example | NAME | $IC_{50}$ Jarid1A (μM) | $IC_{50}$ Jarid1B (μM) | $IC_{50}$ JMJD2C (μM) | $IC_{50}$ JMJD2A (μM) |
|---|---|---|---|---|---|
| 1 | 3-chloro-1H-pyrrolo[3,2-b]-pyridine-7-carboxylic acid | C | D | C | |
| 2 | 2-phenyl-1H-pyrrolo[3,2-b]-pyridine-7-carboxylic acid | B | B | B | B |
| 3 | 2-(2-methylphenyl)-1H-pyrrolo-[3,2-b]pyridine-7-carboxylic acid | B | B | B | A |
| 6 | methyl 2-benzyl-1H-pyrrolo-[3,2-b]pyridine-7-carboxylate | D | D | D | |
| 7 | 2-benzyl-1H-pyrrolo-[3,2-b]-pyridine-7-carboxylic acid | B | B | B | B |

TABLE 3-continued

| Chemical Synthesis Example | NAME | IC$_{50}$ Jarid1A (µM) | IC$_{50}$ Jarid1B (µM) | IC$_{50}$ JMJD2C (µM) | IC$_{50}$ JMJD2A (µM) |
|---|---|---|---|---|---|
| 8 | 2-propyl-1H-pyrrolo[3,2-b]-pyridine-7-carboxylic acid | C | C | A | |
| 10 | 2-(hydroxymethyl)-1H-pyrrolo-[3,2-b]pyridine-7-carboxylic acid | B | B | B | |
| 11 | methyl 2-cyclopropyl-1H-pyrrolo-[3,2-b]pyridine-7-carboxylate | D | D | D | |
| 12 | 2-cyclopropyl-1H-pyrrolo[3,2-b]pyridine-7-carboxylic acid | C | C | A | |
| 5 | 2-(2-hydroxypropan-2-yl)-1H-pyrrolo[3,2-b]pyridine-7-carboxylic acid | B | B | A | |
| 4 | methyl 2-(2-hydroxypropan-2-yl)-1H-pyrrolo[3,2-b]-pyridine-7-carboxylate | D | D | D | |
| 13 | methyl 2-(1-hydroxycyclo-hexyl)-1H-pyrrolo[3,2-b]-pyridine-7-carboxylate | D | D | D | |
| 14 | 2-(1-hydroxycyclohexyl)-1H-pyrrolo[3,2-b]pyridine-7-carboxylic acid | B | B | B | |
| 15 | methyl 2-(4-methoxy-2-methylphenyl)-1H-pyrrolo-[3,2-b]pyridine-7-carboxylate | D | D | D | |
| 17 | methyl 2-(1-hydroxyethyl)-1H-pyrrolo[3,2-b]pyridine-7-carboxylate | D | D | D | |
| 18 | 2-(1-hydroxyethyl)-1H-pyrrolo-[3,2-b]pyridine-7-carboxylic acid | B | B | A | |
| 16 | 2-(4-methoxy-2-methyl-phenyl)-1H-pyrrolo[3,2-b]-pyridine-7-carboxylic acid | B | B | B | |
| 20 | 2-[hydroxy(phenyl)methyl]-1H-pyrrolo[3,2-b]pyridine-7-carboxylic acid | A | A | A | |
| 22 | 2-[hydroxy-(3-methylphenyl)-methyl]-1H-pyrrolo[3,2-b]-pyridine-7-carboxylic acid | A | A | A | |
| 24 | 2-[hydroxy-(3-methoxy-phenyl)methyl]-1H-pyrrolo[3,2-b]pyridine7-carboxylic acid | A | A | B | B |
| 21 | methyl 2-[hydroxy-(3-methyl-phenyl)methyl]-1H-pyrrolo-[3,2-b]-pyridine-7-carboxylate | C | D | D | |
| 20 | methyl 2-[hydroxy(phenyl)-methyl]-1H-pyrrolo[3,2-b]-pyridine-7-carboxylate | C | D | D | |
| 9 | methyl 2-(hydroxymethyl)-1H-pyrrolo[3,2-b]pyridine-7-carboxylate | D | D | D | |
| 23 | methyl 2-[hydroxy-(3-methoxy-phenyl)methyl]-1H-pyrrolo[3,2-b]-pyridine-7-carboxylate | | | | |
| 25 | methyl 2-(1-hydroxypropyl)-1H-pyrrolo[3,2-b]pyridine-7-carboxylate | D | D | D | |
| 27 | 2-(1-hydroxycyclopentyl)-1H-pyrrolo[3,2-b]pyridine-7-carboxylic acid | A | A | A | |
| 29 | 2-cyclopentyl-1H-pyrrolo[3,2-b]-pyridine-7-carboxylic acid | B | B | A | |
| 28 | methyl 2-cyclopentyl-1H-pyrrolo-[3,2-b]pyridine-7-carboxylate | D | D | D | |
| 26 | 2-(1-hydroxypropyl)-1H-pyrrolo-[3,2-b]pyridine-7-carboxylic acid | A | B | A | |
| 30 | 2-(1-hydroxy-2-methylpropyl)-1H-pyrrolo[3,2-b]pyridine-7-carboxylic acid | B | A | A | |
| 31 | methyl 2-(1-hydroxy-2-methyl-propyl)-1H-pyrrolo[3,2-b]-pyridine-7-carboxylate | | | | |
| 33 | 2-[cyclopropyl(hydroxy)-methyl]-1H-pyrrolo[3,2-b]pyridine-7-carboxylic acid | A | A | A | |

TABLE 3-continued

| Chemical Synthesis Example | NAME | IC$_{50}$ Jarid1A (μM) | IC$_{50}$ Jarid1B (μM) | IC$_{50}$ JMJD2C (μM) | IC$_{50}$ JMJD2A (μM) |
|---|---|---|---|---|---|
| 32 | methyl 2-[cyclopropyl-(hydroxy)methyl]-1H-pyrrolo-[3,2-b]pyridine-7-carboxylate | | | | |
| 34 | 2-[(3-methoxyphenyl)methyl]-1H-pyrrolo[3,2-b]pyridine-7-carboxylic acid | A | B | B | |
| 35 | methyl 2-[(3-methylphenyl)-methyl]-1H-pyrrolo[3,2-b]-pyridine-7-carboxylate | | | | |
| 37 | methyl 2-(2-cyclopropyl-1-hydroxyethyl)-1H-pyrrolo[3,2-b]-pyridine-7-carboxylate | | | | |
| 36 | 2-[(3-methylphenyl)methyl]-1H-pyrrolo[3,2-b]pyridine-7-carboxylic acid | A | B | A | |
| 38 | 2-(2-cyclopropyl-1-hydroxyethyl)-1H-pyrrolo[3,2-b]pyridine-7-carboxylic acid | A | A | A | |
| 39 | 2-(phenoxymethyl)-1H-pyrrolo[3,2-b]pyridine-7-carboxylic acid | A | A | A | B |
| 41 | 2-(methoxymethyl)-1H-pyrrolo[3,2-b]pyridine-7-carboxylic acid | B | B | A | |
| 40 | methyl 2-(methoxymethyl)-1H-pyrrolo[3,2-b]pyridine-7-carboxylate | | | | |
| 43 | 2-[hydroxy(oxan-4-yl)methyl]-1H-pyrrolo[3,2-b]pyridine-7-carboxylic acid | A | A | B | B |
| 42 | methyl 2-[hydroxy(oxan-4-yl)-methyl]-1H-pyrrolo[3,2-b]-pyridine-7-carboxylate | | | | |
| 44 | 2-[(4-chlorophenyl)methyl]-1H-pyrrolo[3,2-b]pyridine-7-carboxylic acid | A | A | B | |
| 46 | 2-(1-hydroxy-1-phenylethyl)-1H-pyrrolo[3,2-b]pyridine-7-carboxylic acid | A | B | B | |
| 45 | methyl 2-(1-hydroxy-1-phenylethyl)-1H-pyrrolo[3,2-b]-pyridine-7-carboxylate | | | | |
| 47 | methyl 2-[hydroxy-(2-methyl-pyrazol-3-yl)methyl]-1H-pyrrolo-[3,2-b]pyridine-7-carboxylate | | | | |
| 49 | methyl 2-[hydroxy-(1-methyl-pyrazol-4-yl)methyl]-1H-pyrrolo-[3,2-b]pyridine-7-carboxylate | | | | |
| 51 | methyl 2-(cyclopentylmethyl)-1H-pyrrolo[3,2-b]pyridine-7-carboxylate | | | | |
| 48 | 2-[hydroxy-(2-methylpyrazol-3-yl)-methyl]-1H-pyrrolo[3,2-b]-pyridine-7-carboxylic acid | A | A | A | |
| 52 | 2-(cyclopentylmethyl)-1H-pyrrolo[3,2-b]pyridine-7-carboxylic acid | A | B | A | |
| 53 | methyl 2-(cyclohexylmethyl)-1H-pyrrolo[3,2-b]pyridine-7-carboxylate | | | | |
| 54 | 2-(cyclohexylmethyl)-1H-pyrrolo[3,2-b]pyridine-7-carboxylic acid | B | B | A | |
| 50 | 2-[hydroxy-(1-methylpyrazol-4-yl)methyl]-1H-pyrrolo[3,2-b]-pyridine-7-carboxylic acid | A | B | B | |
| 55 | methyl 2-[[4-(trifluoromethyl)-phenyl]methyl]-1H-pyrrolo[3,2-b]-pyridine-7-carboxylate | | | | |
| 56 | 2-[[4-(trifluoromethyl)phenyl]-methyl]-1H-pyrrolo[3,2-b]-pyridine-7-carboxylic acid | B | B | B | |
| 57 | methyl 2-(2-cyanoethyl)-1H-pyrrolo[3,2-b]pyridine-7-carboxylate | | | | |

TABLE 3-continued

| Chemical Synthesis Example | NAME | IC$_{50}$ Jarid1A (μM) | IC$_{50}$ Jarid1B (μM) | IC$_{50}$ JMJD2C (μM) | IC$_{50}$ JMJD2A (μM) |
|---|---|---|---|---|---|
| 58 | 2-(2-cyanoethyl)-1H-pyrrolo[3,2-b]pyridine-7-carboxylic acid | B | B | A | |
| 59 | 2-[(4-methoxyphenyl)methyl]-1H-pyrrolo[3,2-b]pyridine-7-carboxylic acid | B | B | A | |
| 60 | 2-[(4-fluorophenoxy)methyl]-1H-pyrrolo[3,2-b]pyridine-7-carboxylic acid | A | A | B | |
| 61 | Methyl 2-[(4-methylphenoxy)-methyl]-1H-pyrrolo[3,2-b]-pyridine-7-carboxylate | | | | |
| 62 | 2-[(4-methylphenoxy)methyl]-1H-pyrrolo[3,2-b]pyridine-7-carboxylic acid | B | B | B | |
| 63 | Methyl 2-[(4-chlorophenoxy)-methyl]-1H-pyrrolo[3,2-b]-pyridine-7-carboxylate | | | | |
| 64 | 2-[(4-chlorophenoxy)methyl]-1H-pyrrolo[3,2-b]pyridine-7-carboxylic acid | A | A | A | |
| 66 | 2-[(2-methylphenoxy)methyl]-1H-pyrrolo[3,2-b]pyridine-7-carboxylic acid | A | A | B | |
| 65 | methyl 2-[(2-methylphenoxy)-methyl]-1H-pyrrolo[3,2-b]-pyridine-7-carboxylate | | | | |
| 68 | 2-[[4-(trifluoromethyl)-phenoxy]-methyl]-1H-pyrrolo[3,2-b]-pyridine-7-carboxylic acid | A | A | B | |
| 67 | methyl 2-[[4-(trifluoromethyl)-phenoxy]methyl]-1H-pyrrolo-[3,2-b]-pyridine-7-carboxylate | | | | |
| 70 | 2-(2-phenylethyl)-1H-pyrrolo-[3,2-b]pyridine-7-carboxylic acid | B | B | A | |
| 69 | methyl 2-(2-phenylethyl)-1H-pyrrolo[3,2-b]pyridine-7-carboxylate | | | | |
| 72 | 2-[(2-chlorophenyl)-hydroxymethyl]-1H-pyrrolo-[3,2-b]pyridine-7-carboxylic acid | A | A | B | |
| 71 | methyl 2-[(2-chlorophenyl)-hydroxymethyl]-1H-pyrrolo-[3,2-b]pyridine-7-carboxylate | | | | |
| 73 | methyl 2-[(3-methylphenoxy)-methyl]-1H-pyrrolo[3,2-b]-pyridine-7-carboxylate | | | | |
| 74 | 2-[(3-methylphenoxy)methyl]-1H-pyrrolo[3,2-b]pyridine-7-carboxylic acid | A | A | A | |
| 75 | methyl 2-(2,3-dihydro-1-benzo-furan-5-yloxymethyl)-1H-pyrrolo-[3,2-b]pyridine-7-carboxylate | | | | |
| 76 | 2-(2,3-dihydro-1-benzofuran-5-yloxymethyl)-1H-pyrrolo-[3,2-b]pyridine-7-carboxylic acid | A | A | B | |
| 77 | methyl 2-[(2-chlorophenyl)-methyl]-1H-pyrrolo-[3,2-b]pyridine-7-carboxylate | | | | |
| 78 | 2-[(2-chlorophenyl)methyl]-1H-pyrrolo[3,2-b]pyridine-7-carboxylic acid | A | A | A | |
| 79 | 2-[(3-fluorophenoxy)methyl]-1H-pyrrolo[3,2-b]pyridine-7-carboxylic acid | A | A | A | |
| 80 | 2-[(3-chlorophenoxy)methyl]-1H-pyrrolo[3,2-b]pyridine-7-carboxylic acid | A | A | B | |
| 81 | 2-[(3,5-difluorophenoxy)-methyl]-1H-pyrrolo[3,2-b]pyridine-7-carboxylic acid | A | A | A | |
| 82 | 2-[(3,5-dimethylphenoxy)-methyl]-1H-pyrrolo[3,2-b]pyridine-7-carboxylic acid | A | A | B | |

TABLE 3-continued

| Chemical Synthesis Example | NAME | IC$_{50}$ Jarid1A (μM) | IC$_{50}$ Jarid1B (μM) | IC$_{50}$ JMJD2C (μM) | IC$_{50}$ JMJD2A (μM) |
|---|---|---|---|---|---|
| 83 | 2-[(3,5-dichlorophenoxy)-methyl]-1H-pyrrolo[3,2-b]pyridine-7-carboxylic acid | A | A | B | |
| 84 | 2-(1-phenoxyethyl)-1H-pyrrolo[3,2-b]pyridine-7-carboxylic acid | A | A | A | |
| 85 | 2-(1-phenoxybutyl)-1H-pyrrolo[3,2-b]pyridine-7-carboxylic acid | A | A | B | |
| 86 | 2-(3-methyl-1-phenoxybutyl)-1H-pyrrolo[3,2-b]pyridine-7-carboxylic acid | B | B | C | |
| 87 | methyl 2-[(2-chlorophenyl)-propoxymethyl]-1H-pyrrolo-[3,2-b]pyridine-7-carboxylate | | | | |
| 88 | 2-[(2-chlorophenyl)-propoxymethyl]-1H-pyrrolo-[3,2-b]pyridine-7-carboxylic acid | A | A | C | |
| 89 | methyl 2-[(2,4-dichlorophenyl)-methyl]-1H-pyrrolo[3,2-b]-pyridine-7-carboxylate | | | | |
| 90 | 2-[(2,4-dichlorophenyl)methyl]-1H-pyrrolo[3,2-b]pyridine-7-carboxylic acid | A | A | B | |
| 91 | methyl 2-(1-benzofuran-2-yl)-1H-pyrrolo[3,2-b]pyridine-7-carboxylate | | | | |
| 92 | 2-(1-benzofuran-2-yl)-1H-pyrrolo-[3,2-b]pyridine-7-carboxylic acid | B | B | B | |
| 93 | 2-[(4-methoxyphenoxy)methyl]-1H-pyrrolo[3,2-b]pyridine-7-carboxylic acid | B | A | B | |
| 94 | 2-[(2-chlorophenoxy)methyl]-1H-pyrrolo[3,2-b]pyridine-7-carboxylic acid | B | B | C | |
| 95 | 2-[(2-fluorophenoxy)methyl]-1H-pyrrolo[3,2-b]pyridine-7-carboxylic acid | B | B | B | |
| 96 | 2-[(2-chloro-4-fluorophenoxy)-methyl]-1H-pyrrolo[3,2-b]-pyridine-7-carboxylic acid | A | A | B | |
| 97 | 2-[(4-acetamidophenoxy)-methyl]-1H-pyrrolo-[3,2-b]pyridine-7-carboxylic acid | B | B | B | |
| 98 | 2-[(4-cyanophenoxy)methyl]-1H-pyrrolo[3,2-b]pyridine-7-carboxylic acid | A | B | B | |
| 99 | 2-(pyrrolidin-1-ylcarbonyl)-1H-pyrrolo[3,2-b]pyridine-7-carboxylic acid | A | A | A | A |
| 100 | methyl 2-[(4-fluorophenyl)-methyl]pyrrolo[3,2-b]pyridine-7-carboxylate | | | | |
| 101 | 2-[(4-fluorophenyl)methyl]-pyrrolo[3,2-b]pyridine-7-carboxylic acid | A | A | A | |
| 102 | methyl 2-[1-(4-fluorophenyl)-1-hydroxyethyl]-1H-pyrrolo-[3,2-b]pyridine-7-carboxylate | | | | |
| 103 | hydroxyethyl]-1H-pyrrolo-[3,2-Mpyridine-7-carboxylic acid | A | A | A | |
| 104 | methyl 2-(1,2,3,4-tetrahydro-quinolylcarbonyl)pyrrolo[3,2-b]-pyridine-7-carboxylate | | | | |
| 105 | 2-(1,2,3,4-tetrahydroquinolyl-carbonyl)pyrrolo[3,2-N-pyridine-7-carboxylic acid | B | C | C | |
| 106 | methyl 2-(indolinylcarbonyl)-pyrrolo[3,2-b]pyridine-7-carboxylate | | | | |
| 107 | 2-(indolinylcarbonyl)pyrrolo-[3,2-b]pyridine-7-carboxylic acid | A | A | B | |

TABLE 3-continued

| Chemical Synthesis Example | NAME | IC$_{50}$ Jarid1A (µM) | IC$_{50}$ Jarid1B (µM) | IC$_{50}$ JMJD2C (µM) | IC$_{50}$ JMJD2A (µM) |
|---|---|---|---|---|---|
| 108 | methyl 2-(piperidylcarbonyl)-pyrrolo[3,2-b]pyridine-7-carboxylate | | | | |
| 109 | 2-(piperidylcarbonyl)pyrrolo-[3,2-b]pyridine-7-carboxylic acid | B | B | B | |
| 110 | 2-[1-(4-fluorophenyl)ethyl]-1H-pyrrolo[3,2-b]pyridine-7-carboxylic acid | B | B | B | |
| 111 | methyl-2-(3-chloro-4-fluoro-benzyl)-1H-pyrrolo[3,2-b]-pyridine-7-carboxylate | | | | |
| 112 | 2-(3-chloro-4-fluorobenzyl)-1H-pyrrolo[3,2-b]pyridine-7-carboxylic acid | A | A | A | |
| 113 | methyl 2-(4-chloro-3-fluorobenzyl)-1H-pyrrolo[3,2-b]-pyridine-7-carboxylate | | | | |
| 114 | 2-(4-chloro-3-fluorobenzyl)-1H-pyrrolo[3,2-b]pyridine-7-carboxylic acid | A | A | A | |
| 115 | methyl 2-[(3-phenyl-pyrrolidinyl)carbonyl]pyrrolo-[3,2-b]pyridine-7-carboxylate | | | | |
| 116 | 2-[(3-phenylpyrrolidinyl)-carbonyl]pyrrolo[3,2-b]pyridine-7-carboxylic acid | A | A | B | |
| 117 | methyl 2-[(4,4-dimethyl-piperidyl)-carbonyl]pyrrolo-[3,2-b]-pyridine-7-carboxylate | | | | |
| 118 | 2-[(4,4-dimethylpiperidyl)-carbonyl]pyrrolo[3,2-b]pyridine-7-carboxylic acid | A | A | A | |
| 119 | methyl 2-[(3-phenylpiperidyl)-carbonyl]pyrrolo[3,2-b]pyridine-7-carboxylate | | | | |
| 120 | 2-[(3-phenylpiperidyl)-carbonyl]pyrrolo[3,2-b]pyridine-7-carboxylic acid | B | B | B | |
| 121 | methyl 2-(2-1,2,3,4-tetrahydro-isoquinolylcarbonyl)pyrrolo-[3,2-b]pyridine-7-carboxylate | | | | |
| 122 | 2-(2-1,2,3,4-tetrahydroiso-quinolylcarbonyl)pyrrolo[3,2-b]-pyridine-7-carboxylic acid | A | A | B | |
| 123 | methyl 2-[(2,2-dimethyl-pyrrolidinyl)carbonyl]pyrrolo-[3,2-b]pyridine-7-carboxylate | | | | |
| 124 | 2-[(2,2-dimethylpyrrolidinyl)-carbonyl]pyrrolo[3,2-b]pyridine-7-carboxylic acid | B | A | B | |
| 126 | 2-(3,4-fluorobenzyl)-1H-pyrrolo[3,2-b]pyridine-7-carboxylic acid | C | C | A | A |
| 128 | 2-(4-chloro-3-methoxybenzyl)-1H-pyrrolo[3,2-b]pyridine-7-carboxylic acid | C | C | A | B |
| 130 | 2-(3,4-dichlorobenzyl)-1H-pyrrolo[3,2-b]pyridine-7-carboxylic acid | C | C | A | B |
| 132 | 2-(3,4-dichloro-5-fluorobenzyl)-1H-pyrrolo[3,2-b]pyridine-7-carboxylic acid | C | C | B | B |
| 134 | 2-(4-chloro-3-methylbenzyl)-1H-pyrrolo[3,2-b]pyridine-7-carboxylic acid | C | B | A | B |
| 136 | 2-[4-chloro-3-(trifluoromethyl)-benzyl]-1H-pyrrolo[3,2-b]-pyridine-7-carboxylic acid | C | C | A | B |
| 138 | 2-[4-chloro-3-(cyclopropyl-methoxy)benzyl]-1H-pyrrolo-[3,2-b]pyridine-7-carboxylic acid | B | A | A | C |

TABLE 3-continued

| Chemical Synthesis Example | NAME | IC$_{50}$ Jarid1A (μM) | IC$_{50}$ Jarid1B (μM) | IC$_{50}$ JMJD2C (μM) | IC$_{50}$ JMJD2A (μM) |
|---|---|---|---|---|---|
| 142 | 2-[4-chloro-3-(trifluoromethoxy)benzyl]-1H-pyrrolo[3,2-b]-pyridine-7-carboxylic acid | B | A | A | B |

Note:
Biochemical assay IC$_{50}$ data are designated within the following ranges:
A: ≤0.10 μM; B: >0.10 μM to ≤1.0 μM; C: >1.0 μM to ≤10 μM; D: >10 μM

Example 2a: In Vitro Cell-Based Assay-ZR-75-1 Cell Line

An assay to measure the degree of cellular inhibition of KDM5A and KDM5B was developed. This quantitative immuno-blotting assay measures the amount tri-methylated histone H3 at amino acid Lysine number 4, a specific substrate and product of the direct enzymatic activity of the histone demethylases KDM5A and KDM5B from extracts of the ZR-75-1 breast cancer cell line.

Assay Principle

This assay is a fluorometric immunoassay for the quantification of tri-methyl H3K4 extracted from cells treated with test compound and is used as a measure of the cellular inhibition of KDM5A/B.

Assay Method

ZR-75-1 (PTEN null, ER+) breast cancer cells numbering 50,000 (ATCC) were seeded into each well of a 96-well tissue culture treated plate and then exposed to an 11 point dilution of test compound with final concentration ranges of test compound ranging from 1250 μM to 10 nM. Cells were left in the presence of test compound for 72 hr. Extracts were prepared containing all of the cellular histone material using detergent based lysis and sonication methods. These lysates were subsequently normalized for total protein content using a colorimetric bicinchonic acid assay (MicroBCA Pierce/Thermo Scientific). Normalized cell extracts were then subjected to typical immuno-blotting procedures using NuPage reagents (Life Technologies). Electrophoretically separated histones were then transferred and immobilized using polyvinylidene difluoride membrane (Immobilon-FL Millipore). The amount of tri-methylated lysine 4 of histone H3 was detected using an antibody specific to the tri-methylated state (Cell Signaling Technologies) and quantified on an infrared imager using a densitometry software package (Odyssey CLx, Image Studio, Li-Cor). This background subtracted densitometry value was reported as a ration of the GAPDH amount for that sample and then calculated as a percent of the DMSO treated sample. The software package XL-fit (IDBS) was then used to calculate a relative IC$_{50}$ value for the dilution series of a given test compound according to the equation:

$$fit=(D+((V\max*(x\char`\^n))/((x\char`\^n)+(Km\char`\^n)))).$$

Example 2b: In Vitro Cell-Based Assay—KYSE-150 Cell Line

The primary cellular assay for JMJD2C inhibition is an assay which measures cellular proliferation via Bromodeoxyuridine (BrdU) incorporation after 168 hr of compound incubation. This is a quantitative ELISA assay measuring DNA incorporation of BrdU during S-phase as a direct readout of cellular proliferation. The KYSE-150 cell line is a JMJD2C gene amplified cell line.

Assay Principle

This is a colorimetric immunoassay for the quantification of cell proliferation. Cells treated for 168 hr with test compounds are assayed for their ability to go through S-phase as a measure of their proliferative potential.

Assay Method

The human KYSE-150 (SMAD4 mut, TP53 mut) esophageal carcinoma cell line was seeded at 2,000 cells/well on a 96-well tissue culture treated plate. After an overnight incubation, cells were treated with a test compound in an 11 point dilution series with final concentrations ranging from 100 μM to 2 nM. Cells were then incubated in the presence of compound for 168 hr. After compound incubation, the cells were assayed using a BrdU Cell Proliferation ELISA (Roche). The cells were first incubated with BrdU labeling reagent for 2 hr. After 2 hr, these BrdU incorporated cells were fixed and denatured, probed with an anti-BrdU-Peroxidase antibody for 1.5 hr and washed. Finally, a tetramethylbenzidine peroxidase substrate was added to each well for 15 min followed by H$_2$SO$_4$ stop solution. The plate is read at 450 nm, and the raw optical density data is transferred into XLFit (IDBS) for IC$_{50}$ calculation using the formula:

$$fit=(D+((V\max*(x\char`\^n))/((x\char`\^n)+(Km\char`\^n))))$$

Table 4 provides the cellular IC$_{50}$ values of various compounds disclosed herein.

TABLE 4

| Chemical Synthesis Example | Name | IC$_{50}$ ZR-75-1 cell-MOA (μM) | IC$_{50}$ KYSE-150 cell-BrdU (μM) |
|---|---|---|---|
| 6 | methyl 2-benzyl-1H-pyrrolo [3,2-b]-pyridine-7-carboxylate | D | |
| 7 | 2-benzyl-1H-pyrrolo[3,2-b]pyridine-7-carboxylic acid | D | |
| 34 | 2-[(3-methoxyphenyl)methyl]-1H-pyrrolo[3,2-b]pyridine-7-carboxylic acid | D | |
| 36 | 2-[(3-methylphenyl)methyl]-1H-pyrrolo[3,2-b]pyridine-7-carboxylic acid | D | |
| 42 | methyl 2-[hydroxy(oxan-4-yl)methyl]-1H-pyrrolo[3,2-b]pyridine-7-carboxylate | D | |
| 44 | 2-[(4-chlorophenyl)methyl]-1H-pyrrolo[3,2-b]pyridine-7-carboxylic acid | D | |
| 46 | 2-(1-hydroxy-1-phenylethyl)-1H-pyrrolo[3,2-b]pyridine-7-carboxylic acid | D | |
| 45 | methyl 2-(1-hydroxy-1-phenylethyl)-1H-pyrrolo[3,2-b]pyridine-7-carboxylate | D | |
| 47 | methyl 2-[hydroxy-(2-methylpyrazol-3-yl)methyl]-1H-pyrrolo[3,2-b]pyridine-7-carboxylate | D | |
| 48 | 2-[hydroxy-(2-methylpyrazol-3-yl)-methyl]-1H-pyrrolo[3,2-b]pyridine-7-carboxylic acid | D | |

TABLE 4-continued

| Chemical Synthesis Example | Name | $IC_{50}$ ZR-75-1 cell-MOA ($\mu$M) | $IC_{50}$ KYSE-150 cell-BrdU ($\mu$M) |
|---|---|---|---|
| 50 | 2-[hydroxy-(1-methylpyrazol-4-yl)-methyl]-1H-pyrrolo[3,2-b]pyridine-7-carboxylic acid | D | |
| 60 | 2-[(4-fluorophenoxy)methyl]-1H-pyrrolo[3,2-b]pyridine-7-carboxylic acid | C | |
| 64 | 2-[(4-chlorophenoxy)methyl]-1H-pyrrolo[3,2-b]pyridine-7-carboxylic acid | C | |
| 66 | 2-[(2-methylphenoxy)methyl]-1H-pyrrolo[3,2-b]pyridine-7-carboxylic acid | D | |
| 72 | 2-[(2-chlorophenyl)-hydroxymethyl]-1H-pyrrolo[3,2-b]pyridine-7-carboxylic acid | D | |
| 74 | 2-[(3-methylphenoxy)methyl]-1H-pyrrolo[3,2-b]pyridine-7-carboxylic acid | D | |
| 101 | 2-[(4-fluorophenyl)methyl]pyrrolo-[3,2-b]pyridine-7-carboxylic acid | D | |
| 125 | Methyl 2-(3,4-difluorobenzyl)-1H-pyrrolo[3,2-b]pyridine-7-carboxylate | | C |
| 127 | Methyl-2-(4-chloro-3-methoxybenzyl)-1H-pyrrolo[3,2-b]pyridine-7-carboxylate | | A |
| 129 | Methyl-2-(3,4-dichlorobenzyl)-1H-pyrrolo[3,2-b]pyridine-7-carboxylate | | A |
| 131 | Methyl-2-(3,4-dichloro-5-fluoro-benzyl)-1H-pyrrolo[3,2-b]pyridine-7-carboxylate | | A |
| 133 | Methyl-2-(4-chloro-3-methylbenzyl)-1H-pyrrolo[3,2-b]pyridine-7-carboxylate | | B |
| 135 | Methyl-2-[4-chloro-3-(trifluoro-methyl)benzyl]-1H-pyrrolo[3,2-b]-pyridine-7-carboxylate | | A |
| 137 | Methyl 2-[4-chloro-3-(cyclopropylmethoxy)benzyl]-1H-pyrrolo[3,2-b]pyridine-7-carboxylate | | A |
| 139 | methyl-2-[4-chloro-3-(2,2,2-trifluoroethoxy)benzyl]-1H-pyrrolo-[3,2-b]pyridine-7-carboxylate | | A |
| 141 | methyl-2-[4-chloro-3-(trifluoromethoxy)benzyl]-1H-pyrrolo[3,2-b]pyridine-7-carboxylate | | A |
| 143 | 2-[4-chloro-benzyl]-N-methyl-1H-pyrrolo[3,2-b]pyridine-7-carboxamide | | B |
| 144 | 2-[4-chloro-3-(trifluoromethoxy)-benzyl]-N-methyl-1H-pyrrolo[3,2-b]-pyridine-7-carboxamide | | A |

Note:
Cellular assay $IC_{50}$ data are designated within the following ranges:
A: ≤0.10 $\mu$M; B: >0.10 $\mu$M to ≤1.0 $\mu$M; C: >1.0 $\mu$M to ≤10 $\mu$M; D: >10 $\mu$M Example 3: In Vivo Xenograft Study Time release pellets containing 0.72 mg 17βEstradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1\times10^7$ cells/mL. MCF-7 cells are subcutaneously injected (100 $\mu$L/animal) on the right flank 2-3 days post-pellet implantation and tumor volume ½(length×width$^2$) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1: Oral Tablet

A tablet is prepared by mixing 48% by weight of a compound of Formula (I) or a pharmaceutically acceptable salt thereof, 45% by weight of microcrystalline cellulose, 5% by weight of low-substituted hydroxypropyl cellulose, and 2% by weight of magnesium stearate.

Tablets are prepared by direct compression. The total weight of the compressed tablets is maintained at 250 mg-500 mg.

We claim:

1. A method for inhibiting a histone demethylase enzyme comprising contacting the histone demethylase enzyme with a compound of Formula (II)

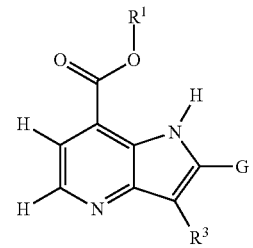

Formula (II)

wherein the compound of Formula (II) includes pharmaceutically acceptable salts thereof, and wherein, $R^1$ is hydrogen or alkyl;

G is X—$R^2$ or $X^1$-alkyl, wherein

X is a bond, alkyl, alkyl-O—, —C(O)—, —C(O)—NH—, —NH—, —NH—C(O)—, —O—, —S—, or —$SO_2$;

$R^2$ is selected from monocyclic or bicyclic carbocyclyl, heterocyclyl, aryl, or heteroaryl, optionally substituted with at least one alkyl, phenyl, halogen, hydroxyl, —$CF_3$, —CN, NH—C(O), —O-alkyl, —O-carbocyclyl, —O-alkyl-$CF_3$, or —O—$CF_3$;

$X^1$ is a bond, —C(O)—, —C(O)—NH—, —NH—, —NH—C(O), —O—, —S—, or —$SO_2$—; and $R^3$ is hydrogen, halogen, or alkyl.

2. The method of claim 1, wherein $R^1$ is hydrogen.

3. The method of claim 1, wherein $R^3$ is hydrogen.

4. The method of claim 1, wherein G is X—$R^2$.

5. The method of claim 4, wherein X is a bond and $R^2$ is optionally substituted monocyclic or bicyclic aryl.

6. The method of claim 4, wherein X is alkyl and $R^2$ is optionally substituted monocyclic or bicyclic aryl.

7. The method of claim 6, wherein $R^3$ is hydrogen.

8. The method of claim 7, wherein X is methyl.

9. The method of claim 8, wherein $R^2$ is di-substituted phenyl.

10. The method of claim 9, wherein $R^2$ is substituted with at least one halogen.

11. The method of claim 10, wherein $R^1$ is methyl.

12. The method of claim 3, wherein X is a bond and $R^2$ is optionally substituted monocyclic or bicyclic heteroaryl.

13. The method of claim 3, wherein X is alkyl and $R^2$ is optionally substituted monocyclic or bicyclic heteroaryl.

14. The method of claim 1, wherein the compound of Formula (II) is combined with at least one pharmaceutically acceptable excipient.

15. A method for inhibiting histone demethylase-dependent cellular proliferation comprising contacting the cell with a compound of Formula (II)

Formula (II)

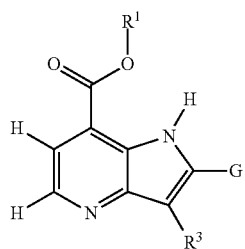

wherein the compound of Formula (II) includes pharmaceutically acceptable salts thereof, and wherein,
$R^1$ is hydrogen or alkyl;
G is $X-R^2$ or $X^1$-alkyl, wherein
  X is a bond, alkyl, alkyl-O—, —C(O)—, —C(O)—NH—, —NH—, —NH—C(O)—, —O—, —S—, or —SO$_2$;

$R^2$ is selected from monocyclic or bicyclic carbocyclyl, heterocyclyl, aryl, or heteroaryl, optionally substituted with at least one alkyl, phenyl, halogen, hydroxyl, —CF$_3$, —CN, NH—C(O), —O-alkyl, —O-carbocyclyl, —O-alkyl-CF$_3$, or —O—CF$_3$;

$X^1$ is a bond, —C(O)—, —C(O)—NH—, —NH—, —NH—C(O), —O—, —S—, or —SO$_2$—; and $R^3$ is hydrogen, halogen, or alkyl.

16. The method of claim 15, wherein $R^3$ is hydrogen.

17. The method of claim 16, wherein $R^1$ is methyl.

18. The method of claim 17, wherein G is $X-R^2$.

19. The method of claim 18, wherein X is alkyl and $R^2$ is optionally substituted monocyclic or bicyclic aryl.

20. The method of claim 19, wherein X is methyl and $R^2$ is di-substituted phenyl.

* * * * *